United States Patent
Zhong et al.

(10) Patent No.: US 10,023,565 B2
(45) Date of Patent: Jul. 17, 2018

(54) N,N' SUBSTITUTED PIPERIDINAMINE COMPOUNDS, AND PREPARATION METHOD AND USAGE THEREOF

(71) Applicant: Institute of Pharmacology and Toxicology Academy of Military Medical Sciences P.L.A. China, Beijing (CN)

(72) Inventors: Wu Zhong, Beijing (CN); Song Li, Beijing (CN); Yanqun Zeng, Beijing (CN); Junhai Xiao, Beijing (CN); Xinbo Zhou, Beijing (CN); Zhibing Zheng, Beijing (CN); Xingzhou Li, Beijing (CN); Xiaokui Wang, Beijing (CN); Lili Wang, Beijing (CN)

(73) Assignee: INSTITUTE OF PHARMACOLOGY AND TOXICOLOGY ACADEMY OF MILITARY MEDICAL SCIENCES P.L.A. CHINA, Beijing (CN)

( * ) Notice: Subject to any disclaimer, the term of this patent is extended or adjusted under 35 U.S.C. 154(b) by 0 days.

(21) Appl. No.: 15/105,702

(22) PCT Filed: Dec. 19, 2014

(86) PCT No.: PCT/CN2014/094338
§ 371 (c)(1),
(2) Date: Jul. 27, 2016

(87) PCT Pub. No.: WO2015/090226
PCT Pub. Date: Jun. 25, 2015

(65) Prior Publication Data
US 2016/0333002 A1 Nov. 17, 2016

(30) Foreign Application Priority Data
Dec. 20, 2013 (CN) .......................... 2013 1 0704759

(51) Int. Cl.
| | | |
|---|---|---|
| *A61K 31/454* | (2006.01) | |
| *A61K 31/506* | (2006.01) | |
| *C07D 401/04* | (2006.01) | |
| *C07D 417/06* | (2006.01) | |
| *A61K 45/06* | (2006.01) | |

(52) U.S. Cl.
CPC .......... *C07D 417/06* (2013.01); *A61K 31/454* (2013.01); *A61K 31/506* (2013.01); *A61K 45/06* (2013.01); *C07D 401/04* (2013.01)

(58) Field of Classification Search
CPC .. A61K 31/454; A61K 31/506; C07D 401/04; C07D 417/06
See application file for complete search history.

(56) References Cited

U.S. PATENT DOCUMENTS

| | | | |
|---|---|---|---|
| 4,514,398 A | 4/1985 | Regnier et al. | |
| 5,260,318 A * | 11/1993 | Lubisch ............... | C07D 211/58 514/318 |
| 5,972,947 A | 10/1999 | Tsaklakidis et al. | |
| 2004/0248904 A1 | 12/2004 | Dhanoa et al. | |

FOREIGN PATENT DOCUMENTS

| | | |
|---|---|---|
| CN | 1777612 A | 5/2006 |
| EP | 0 156 433 A2 | 10/1985 |
| WO | WO 2009/106561 A1 | 9/2009 |
| WO | WO 2012/166617 A2 | 12/2012 |

OTHER PUBLICATIONS

Invitation pursuant to Rule 63(1) EPC for EP Appl. No. 14 872 369, dated Jun. 23, 2017, European Patent Office, Munich, Germany.
Extended European search report including the supplementary European search report and the European search opinion, for EP Appl. No. 14872369.5, dated Sep. 18, 2017, European Patent Office, Munich, Germany.
Dhainaut, A et al., "New purines and purine analogs as modulators of multidrug resistance," J Med Chem. Sep. 27, 1996;39(20):4099-4108, Am. Chem. Soc., Washington, DC.
Database REAXYS [online], 1980, XP002773378, Database accession Nos. 6869503, 6871206 and 6875045, (from Moragues et al., Il Farmaco, Edizione, Scientifica 35(11) 951-964 (1980)), Reed Elsevier Properties SA , downloaded Jun. 19, 2017.

(Continued)

*Primary Examiner* — Kendra D Carter
(74) *Attorney, Agent, or Firm* — Sterne, Kessler, Goldstein & Fox P.L.L.C.

(57) ABSTRACT

The present invention relates to a compound of formula (I), a stereomeride, pharmaceutically acceptable salt, a solvate or an N-oxide thereof, a medicine composition comprising the compound, a method for preparing the compound, and a usage of the compound in treating diseases related to Hsp70. The diseases are preferably selected from tumors, neurodegenerative diseases, and allogeneic transplantation rejection and infection.

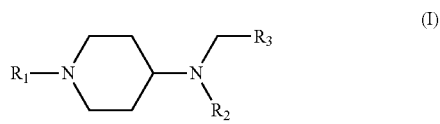

(I)

5 Claims, 5 Drawing Sheets

(56) References Cited

OTHER PUBLICATIONS

Powers, MV et al., "Targeting HSP70: the second potentially druggable heat shock protein and molecular chaperone?," Cell Cycle. Apr. 15, 2010;9(8):1542-50. Epub Apr. 15, 2010, Landes Bioscience, Georgetown, TX.

Zeng, Y et al., "Design and synthesis of piperidine derivatives as novel human heat shock protein 70 inhibitors for the treatment of drug-resistant tumors," Eur J Med Chem. Jun. 5, 2015;97:19-31. doi: 10.1016/j.ejmech.2015.04.043. Epub Apr. 21, 2015, Editions Scientifiques Elsevier, Paris, France.

International Search Report (ISR) for PCT/CN2014/094338; I.A. fd: Dec. 19 2014, dated Mar. 13, 2015, State Intellectual Property Office of the P.R. China, Beijing, China.

International Preliminary Report on Patentability (IPRP) including the Written Opinion of the International Searching Authority (PCT Rule 44bis) for PCT/CN2014/094338; I.A. fd: Dec. 19 2014, dated Jun. 21, 2016, by the International Bureau of WIPO, Geneva, Switzerland.

Jia, JM et al. "Identification, design and bio-evaluation of novel Hsp90 inhibitors by ligand-based virtual screening," PLoS One. 2013;8(4):e59315. doi: 10.1371/journal.pone.0059315. Epub Apr. 2, 2013, Public Library of Science, San Francisco, CA.

\* cited by examiner

Survival rate comparison chart of 12 types of cell after administration of the compound of Example 36

Survival rate comparison chart of 12 types of cells after administration of the compound of Example 37

Survival rate comparison chart of 12 types of cells after administration of the compound of Example 40

Survival rate comparison chart of 12 types of cells afte administration of the compound of Example 47

Survival rate comparison chart of 12 types of cells after administration of the compound of Example 49

N,N' SUBSTITUTED PIPERIDINAMINE COMPOUNDS, AND PREPARATION METHOD AND USAGE THEREOF

TECHNICAL FIELD

The present invention relates to N,N' substituted piperidinamine compounds of formula (I), a method for preparing the compounds and usage of the compounds as drug for treating diseases related to Hsp70 such as tumor.

BACKGROUND ART

Heat shock protein 70 (Hsp70) is widely present in nucleus, cytoplasm, endoplasmic reticulum, mitochondria and chloroplast cells, and is involved in intracellular protein de novo synthesis, orientation, protein maturation and degradation of misfolded proteins, thus affecting the growth and metabolism function of cells. In cells, Hsp70 binding to nascent polypeptides on ribosome can prevent misfolding of nascent polypeptides; Hsp70 is essential for remodeling clathrin in the process of pinocytosis of mammalian cells; and Hsp70 binding to non native conformation proteins can promote proper folding and assembly of proteins, and can maintain extended conformation of protein precursors and prevent their aggregation denaturation and degradation, allowing easy transport to organelles.

Studies have shown that, Hsp70 is related to many diseases, such as tumors, neurodegenerative diseases, allograft rejection or infections and the like. In cancer cells, Hsp70 affects apoptosis mainly through the following pathways: (1) mitochondrial pathway: in the early stage of mitochondria, Hsp70 blocks migration of Bax, and decreases permeability of mitochondrial outer membrane, thereby inhibiting the release of cytc and AIF from mitochondria; in the late stage of mitochondria, Hsp70 binds directly to Apaf1, blocks the aggregation of procaspase-9, so that apoptotic body cannot be formed, and caspase-3 downstream cannot be activated; (2) death receptor pathway: Hsp70, by inhibiting the activation of JNK, and binding to Akt and PKC, triggers dephosphorylation of kinase, and allows protein stabilization, cell survival; similarly, Hsp70 can also bind to DR4 and DR5, and inhibit TRAIL-induced DISC aggregation and activity; (3) DNA degradation pathway: the complex of Hsp70, Hsp40, ICAD can inhibit the activity and folding effect of DNase CAD, prevent late apoptotic chromosomal DNA from being degraded, so as to achieve anti-apoptosis effect.

Study on Hsp70 useful for tumor therapy has become a hot spot in recent years, but a highly active inhibitor has not found yet, and the mechanism of action is not clear. Whether or not Hsp70 inhibitor can be, and how it is, used for clinical tumor therapy needs further study. In tumor cells, Hsp70 and its related protein expression are abnormally high, resulting in decreased activity of drug. The compounds with new structure as synthesized by us suggest that after dosing stimulation tumor cells play a potential defense mechanism via protein Hsp70 to produce drug resistance, while Hsp70 inhibitor is expected to reverse the antitumor drug resistance of tumor cell strains. By using surface plasma technology (SPR) on a BIACORE T100 Biomolecular Interaction Analysis, we determined the affinity of small molecule compound Hsp70 inhibitor with target protein Hsp70, and found small molecule compound that has a high affinity with Hsp70.

We tested the inhibitory effects of example compounds against two kinds of lapatinib-sensitive human breast cancer cell strains (BT474, SK-BR3) and four kinds of lapatinib-resistant human breast cancer cell strains (BT/Lap$^R$1.0, MDA-MB-361, SK/Lap$^R$1.0, MDA-MB-453), illustrated the nature of interaction between example compounds and lapatinib, and evaluated the effect of this kind of compounds to reverse lapatinib resistance in vitro. It was found that the example compounds could inhibit the growth of tumor (e.g. human breast cancer) well, and could reverse lapatinib resistance.

We invented a new kind of highly active Hsp70 inhibitor, to overcome the problem of tumor drug resistance and improve tumor treatment effect, and thereby provided a new medical strategy for clinical tumor therapy.

The object of the present invention is to provide a kind of N,N' substituted piperidinamine compounds, which can be used as drug for the treatment of Hsp70-related diseases, especially tumor, and can reverse drug resistance to existing drugs.

Contents of the Invention

In one aspect, the present invention provides a compound of formula (I), a stereoisomer, a pharmaceutically acceptable salt, a solvate or an N-oxide thereof,

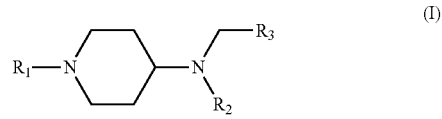

wherein:

$R_1$ is selected from the group consisting of aryl, arylalkyl, cycloalkyl, cycloalkylalkyl, heterocyclyl, heterocyclylalkyl, heteroaryl and heteroarylalkyl, which are unsubstituted or substituted with 1-3 (e.g., 1, 2 or 3) substituents independently selected from the group consisting of: —F, —Cl, —Br, —I, nitro, hydroxy, amino, cyano, $C_{1-6}$alkyl, halo$C_{1-6}$alkyl, $C_{1-6}$ alkylthio, halo$C_{1-6}$alkylthio, $C_{1-6}$alkoxy, halo$C_{1-6}$alkoxy, $C_{3-6}$cycloalkyl, $C_{3-6}$cycloalkyloxy, $C_{2-6}$alkenyl, $C_{2-6}$alkynyl and —NR$_4$R$_5$;

$R_2$ is selected from the group consisting of hydrogen, $C_{1-6}$alkyl, halo$C_{1-6}$alkyl, $C_{3-6}$cycloalkyl, $C_{2-6}$alkenyl and $C_{2-6}$alkynyl;

$R_3$ is selected from the group consisting of aryl, heteroaryl, cycloalkyl and heterocyclyl, which are unsubstituted or substituted with 1 to 5 (e.g. 1, 2, 3, 4 or 5) substituents independently selected from the group consisting of: —F, —Cl, —Br, —I, —NR$_4$R$_5$, nitro, hydroxy, amino, cyano, $C_{1-6}$alkylthio, halo$C_{1-6}$alkylthio, $C_{1-6}$alkyl, halo$C_{1-6}$alkyl, $C_{3-6}$cycloalkyl, $C_{3-6}$cycloalkyloxy, $C_{2-6}$alkenyl, $C_{2-6}$alkynyl, $C_{1-6}$alkoxy and halo$C_{1-6}$alkoxy;

$R_4$ and $R_5$ are independently selected from the group consisting of —H, $C_{3-6}$cycloalkyl, $C_{2-6}$alkenyl and $C_{2-6}$alkynyl, each optionally substituted with substituents independently selected from the group consisting of: —F, —Cl, —Br, —I, —OH, —CN and $C_{1-6}$alkoxy; or $R_4$ and $R_5$ together with the nitrogen atom to which they are attached form 3-8 membered heterocyclyl, optionally containing 1 to 2 oxygen atoms, said 3-8 membered heterocyclyl optionally are substituted with substituents independently selected from the group consisting of: —F, —Cl, —Br, —I, —OH, —CN, $C_{1-6}$alkyl and $C_{1-6}$alkoxy.

In another aspect, the present invention provides a compound of formula (I), a stereoisomer, a pharmaceutically acceptable salt, a solvate or an N-oxide thereof, wherein:

$R_1$ is selected from the group consisting of aryl, arylalkyl, heteroaryl and heteroarylalkyl, which are unsubstituted or substituted with 1 to 3 (e.g. 1, 2 or 3) substituents independently selected from the group consisting of: —F, —Cl, —Br, —I, methyl, ethyl, propyl, cyclopropyl, nitro, hydroxy, amino, cyano, methoxy, ethoxy, propoxy, cyclopropoxy, methylthio, ethylthio, propylthio, methylamino, ethylamino, propylamino and cyclopropylamino;

$R_2$ is selected from the group consisting of hydrogen and $C_{1-6}$alkyl;

$R_3$ is selected from the group consisting of aryl and heteroaryl, which are unsubstituted or substituted with 1 to 5 (1, 2, 3, 4 or 5) substituents independently selected from the group consisting of: —F, —Br, —I, —$NR_4R_5$, nitro, hydroxy, amino, cyano, $C_{1-6}$alkylthio, halo$C_{1-6}$alkylthio, $C_{1-6}$alkyl, halo$C_{1-6}$alkyl, $C_{3-6}$cycloalkyl, $C_{3-6}$cycloalkyloxy, $C_{2-6}$alkenyl, $C_{2-6}$alkynyl, $C_{1-6}$alkoxy and halo$C_{1-6}$alkoxy;

$R_4$ and $R_5$ are independently selected from the group consisting of —H, $C_{1-6}$alkyl, $C_{3-6}$cycloalkyl, $C_{2-6}$alkenyl and $C_{2-6}$alkynyl, each optionally substituted with substituents independently selected from the group consisting of: —F, —Cl, —Br, —I, —OH, —CN and $C_{1-6}$alkoxy; or $R_4$ and $R_5$ together with the nitrogen atom to which they are attached form 3-8 membered heterocyclyl, optionally containing 1 to 2 oxygen atoms, said 3-8 membered heterocyclyl optionally are substituted with substituents independently selected from the group consisting of: —F, —Cl, —Br, —I, —OH, —CN, $C_{1-6}$alkyl and $C_{1-6}$alkoxy.

In still another aspect, the present invention provides a compound of formula (I), a stereoisomer, a pharmaceutically acceptable salt, a solvate or an N-oxide thereof, wherein:

$R_1$ is selected from the group consisting of phenyl, phenyl$(CH_2)_n$—, pyrimidinyl, pyrimidinyl$(CH_2)_n$—, pyridyl, pyridyl$(CH_2)_n$—, pyrazinyl, pyrazinyl$(CH_2)_n$—, pyridazinyl, pyridazinyl$(CH_2)_n$—, thienyl, thienyl$(CH_2)_n$—, thiazolyl, thiazolyl$(CH_2)_n$—, naphthyl and naphthyl$(CH_2)_n$—, which are unsubstituted or substituted with 1 to 3 (e.g. 1, 2 or 3) substituents independently selected from the group consisting of: —F, —Cl, —Br, —I, methyl, ethyl, propyl, cyclopropyl, nitro, hydroxy, amino, cyano, methoxy, ethoxy, propoxy, cyclopropoxy, methylthio, ethylthio, propylthio, methylamino, ethylamino, propylamino and cyclopropylamino;

n is independently 1, 2 or 3;

$R_2$ is selected from the group consisting of hydrogen, methyl and ethyl;

$R_3$ is selected from the group consisting of phenyl, pyrimidinyl, pyridyl, pyrazinyl, pyridazinyl, thienyl, thiazolyl and naphthyl, which are unsubstituted or substituted with 1 to 3 (e.g. 1, 2 or 3) substituents independently selected from the group consisting of: —F, —Cl, —Br, —I, methyl, ethyl, propyl, cyclopropyl, nitro, hydroxy, amino, cyano, methoxy, ethoxy, propoxy, cyclopropoxy, methylthio, ethylthio, propylthio, methylamino, ethylamino, propylamino and cyclopropylamino.

In some embodiments, $R_1$ is selected from the group consisting of optionally substituted aryl, arylalkyl, cycloalkyl, cycloalkylalkyl, heterocyclyl, heterocyclylalkyl, heteroaryl and heteroarylalkyl.

In some preferred embodiments, $R_1$ is selected from the group consisting of optionally substituted aryl, arylalkyl, heteroaryl and heteroarylalkyl.

In some more preferred embodiments, $R_1$ is selected from the group consisting of optionally substituted heteroaryl and heteroarylalkyl.

In some even more preferred embodiments, $R_1$ is selected from the group consisting of optionally substituted phenyl, phenyl$(CH_2)_n$—, pyrimidinyl, pyrimidinyl$(CH_2)_n$—, pyridyl, pyridyl$(CH_2)_n$—, pyrazinyl, pyrazinyl$(CH_2)_n$—, pyridazinyl, pyridazinyl$(CH_2)_n$—, thienyl, thienyl$(CH_2)_n$—, thiazolyl, thiazolyl$(CH_2)_n$—, naphthyl and naphthyl$(CH_2)_n$—, wherein n is independently 1, 2 or 3.

In some embodiments, $R_2$ is selected from the group consisting of hydrogen, $C_{1-6}$alkyl, $C_{3-6}$cycloalkyl, $C_{2-6}$alkenyl and $C_{2-6}$alkynyl.

In some preferred embodiments, $R_2$ is selected from the group consisting of hydrogen, $C_{1-6}$alkyl and $C_{3-6}$cycloalkyl.

In some more preferred embodiments, $R_2$ is selected from the group consisting of hydrogen and $C_{1-6}$alkyl.

In some even more preferred embodiments, $R_2$ is selected from the group consisting of hydrogen, methyl and ethyl.

In some embodiments, $R_3$ is selected from the group consisting of optionally substituted aryl, heteroaryl, cycloalkyl and heterocyclyl.

In some preferred embodiments, $R_3$ is selected from the group consisting of optionally substituted aryl and heteroaryl.

In some more preferred embodiments, $R_3$ is selected from the group consisting of optionally substituted phenyl, pyrimidinyl, pyridyl, pyrazinyl, pyridazinyl, thienyl, thiazolyl and naphthyl.

In some even more preferred embodiments, $R_3$ is selected from the group consisting of optionally substituted phenyl and naphthyl.

In one aspect, the preferred compound of formula (I) is selected from the following compounds:

(1) N-methyl-N-m-chlorobenzyl-N-{1-[(2-ethoxythiazol-5-yl)methyl]piperidin-4-yl}amine, (2) N-methyl-N-o-cyanobenzyl-N-{1-[(2-ethoxythiazol-5-yl)methyl]piperidin-4-yl}amine, (3) N-methyl-N-(3,4-dichlorobenzyl)-N-{1-[(2-ethoxythiazol-5-yl)methyl]piperidin-4-yl}amine, (4) N-methyl-N-(4-cyanobenzyl)-N-{1-[(2-ethoxythiazol-5-yl)methyl]piperidin-4-yl}amine, (5) N-methyl-N-(2-fluoro-6-chlorobenzyl)-N-{1-[(2-ethoxythiazol-5-yl)methyl]piperidin-4-yl}amine, (6) N-methyl-N-(2-chlorobenzyl)-N-{1-[(2-ethoxythiazol-5-yl)methyl]piperidin-4-yl} amine, (7) N-methyl-N-(4-fluorobenzyl)-N-{[1-(2-ethoxythiazol-5-yl)methyl]piperidin-4-yl} amine, (8) N-methyl-N-(2,4-dichlorobenzyl)-N-{[1-(2-ethoxythiazol-5-yl)methyl]piperidin-4-yl} amine, (9) N-methyl-N-(2,6-dichlorobenzyl)-N-{[1-(2-ethoxythiazol-5-yl)methyl]piperidin-4-yl} amine,

(10) N-methyl-N-(2,5-dichlorobenzyl)-N-{[1-(2-ethoxythiazol-5-yl)methyl]piperidin-4-yl} amine,

(11) N-(3,4-dichlorobenzyl)-N-{1-[(2-chlorothiazol-5-yl)methyl]piperidin-4-yl}amine,

(12) N-(4-fluorobenzyl)-N-{1-[(2-chlorothiazol-5-yl)methyl]piperidin-4-yl}amine,

(13) N-(3-chlorobenzyl)-N-{1-[(2-chlorothiazol-5-yl)methyl]piperidin-4-yl}amine,

(14) N-methyl-N-(2-cyanobenzyl)-N-{1-[(2-chlorothiazol-5-yl)methyl]piperidin-4-yl} amine,

(15) N-methyl-N-(4-cyanobenzyl)-N-{1-[(2-chlorothiazol-5-yl)methyl]piperidin-4-yl} amine,

(16) N-methyl-N-(4-fluorobenzyl)-N-{1-[(2-chlorothiazol-5-yl)methyl]piperidin-4-yl} amine,

(17) N-methyl-N-(3,4-dichlorobenzyl)-N-{1-[(2-chlorothiazol-5-yl)methyl]piperidin-4-yl} amine,

(18) N-methyl-N-(3-chlorobenzyl)-N-{1-[(2-chlorothiazol-5-yl)methyl]piperidin-4-yl} amine,

(19) N-methyl-N-(2-fluoro-6-chlorobenzyl)-N-{[1-(2-chlorothiazol-5-yl)methyl]piperidin-4-yl}amine,

(20) N-methyl-N-(2,4-dichlorobenzyl)-N-{[1-(2-chlorothiazol-5-yl)methyl]piperidin-4-yl} amine,

(21) N-methyl-N-(2-methylbenzyl)-N-{[1-(2-chlorothiazol-5-yl)methyl]piperidin-4-yl} amine,
(22) N-methyl-N-(4-methylbenzyl)-N-{[1-(2-chlorothiazol-5-yl)methyl]piperidin-4-yl} amine,
(23) N-methyl-N-(3-fluorobenzyl)-N-{[1-(2-chlorothiazol-5-yl)methyl]piperidin-4-yl} amine,
(24) N-methyl-N-(2,5-dichlorobenzyl)-N-{[1-(2-chlorothiazol-5-yl)methyl]piperidin-4-yl} amine,
(25) N-methyl-N-(2-methylbenzyl)-N-{[1-(2-methylthiothiazol-5-yl)methyl]piperidin-4-yl} amine,
(26) N-methyl-N-(4-methylbenzyl)-N-{[1-(2-methylthiothiazol-5-yl)methyl]piperidin-4-yl} amine,
(27) N-methyl-N-(3-fluorobenzyl)-N-{[1-(2-methylthiothiazol-5-yl)methyl]piperidin-4-yl} amine,
(28) N-methyl-N-(3-chlorobenzyl)-N-{1-[(2-methylthiothiazol-5-yl)methyl]piperidin-4-yl} amine,
(29) N-methyl-N-(4-fluorobenzyl)-N-{1-[(2-methylthiothiazol-5-yl)methyl]piperidin-4-yl} amine,
(30) N-methyl-N-(3,4-dichlorobenzyl)-N-{1-[(2-methylthiothiazol-5-yl)methyl]piperidin-4-yl}amine,
(31) N-methyl-N-(2-fluoro-6-chlorobenzyl)-N-{1-[(2-methylthiothiazol-5-yl)methyl] piperidin-4-yl}amine,
(32) N-methyl-N-(2,5-dichlorobenzyl)-N-{1-[(2-methylthiothiazol-5-yl)methyl]piperidin-4-yl}amine,
(33) N-methyl-N-(2,4-dichlorobenzyl)-N-{1-[(2-methylthiothiazol-5-yl)methyl]piperidin-4-yl}amine,
(34) N-methyl-N-(2,5-dichlorobenzyl)-N-{1-[(2-methylthiothiazol-5-yl)methyl]piperidin-4-yl}amine,
(35) N-methyl-N-(4-fluorobenzyl)-N-[1-(2-methylthiopyrimidin-4-yl)piperidin-4-yl]amine,
(36) N-methyl-N-(4-cyanobenzyl)-N-[1-(2-methylthiopyrimidin-4-yl)piperidin-4-yl]amine,
(37) N-methyl-N-(2-fluoro-6-chlorobenzyl)-N-[1-(2-methylthiopyrimidin-4-yl)piperidin-4-yl]amine,
(38) N-methyl-N-(3,4-dichlorobenzyl)-N-[1-(2-methylthiopyrimidin-4-yl)piperidin-4-yl] amine,
(39) N-methyl-N-(3-chlorobenzyl)-N-[1-(2-methylthiopyrimidin-4-yl)piperidin-4-yl]amine,
(40) N-methyl-N-(2,4-dichlorobenzyl)-N-[1-(2-methylthiopyrimidin-4-yl)piperidin-4-yl] amine,
(41) N-methyl-N-(2-cyanobenzyl)-N-[1-(2-methylthiopyrimidin-4-yl)piperidin-4-yl]amine,
(42) N-methyl-N-(4-methylbenzyl)-N-[1-(2-methylthiopyrimidin-4-yl)piperidin-4-yl]amine,
(43) N-methyl-N-(2-chlorobenzyl)-N-[1-(2-methoxypyrimidin-4-yl)piperidin-4-yl]amine,
(44) N-methyl-N-(2,4-dichlorobenzyl)-N-[1-(2-methylthiopyrimidin-4-yl)piperidin-4-yl] amine,
(45) N-methyl-N-(3-fluorobenzyl)-N-[1-(2-methylthiopyrimidin-4-yl)piperidin-4-yl]amine,
(46) N-methyl-N-[1-(4-methoxypyrimidin-2-yl)piperidin-4-yl]amine,
(47) N-methyl-N-(2-chlorobenzyl)-N-[1-(2-methylthiopyrimidin-4-yl)piperidin-4-yl]amine,
(48) N-methyl-N-(4-cyanobenzyl)-N-[1-(2-methoxypyrimidin-4-yl)piperidin-4-yl]amine,
(49) N-methyl-N-(2,6-dichlorobenzyl)-N-[1-(2-methylthiopyrimidin-4-yl)piperidin-4-yl] amine,
(50) N-methyl-N-(2-cyanobenzyl)-N-[1-(2-methoxypyrimidin-4-yl)piperidin-4-yl]amine,
(51) N-methyl-N-(4-methylbenzyl)-N-[1-(2-methoxypyrimidin-4-yl)piperidin-4-yl]amine,
(52) N-methyl-N-(2,5-dichlorobenzyl)-N-[1-(2-methoxypyrimidin-4-yl)piperidin-4-yl] amine,
(53) N-methyl-N-(3,4-dichlorobenzyl)-N-[1-(2-methoxypyrimidin-4-yl)piperidin-4-yl] amine,
(54) N-methyl-N-(2-fluoro-6-chlorobenzyl)-N-[1-(2-methoxypyrimidin-4-yl)piperidin-4-yl] amine,
(55) N-methyl-N-(3-chlorobenzyl)-N-[1-(2-methoxypyrimidin-4-yl)piperidin-4-yl]amine,
(56) N-methyl-N-(3-fluorobenzyl)-N-[1-(2-methoxypyrimidin-4-yl)piperidin-4-yl]amine,
(57) N-methyl-N-(4-fluorobenzyl)-N-[1-(2-methoxypyrimidin-4-yl)piperidin-4-yl]amine,
(58) N-methyl-N-(2-chlorobenzyl)-N-[1-(6-methoxypyrimidin-4-yl)piperidin-4-yl]amine,
(59) N-methyl-N-(4-methylbenzyl)-N-[1-(6-methoxypyrimidin-4-yl)piperidin-4-yl]amine,
(60) N-methyl-N-(2,6-dichlorobenzyl)-N-[1-(6-methoxypyrimidin-4-yl)piperidin-4-yl] amine,
(61) N-methyl-N-(3,4-dichlorobenzyl)-N-[1-(6-methoxypyrimidin-4-yl)piperidin-4-yl] amine,
(62) N-methyl-N-(4-fluorobenzyl)-N-[1-(6-methoxypyrimidin-4-yl)piperidin-4-yl]amine,
(63) N-methyl-N-(3-chlorobenzyl)-N-[1-(6-methoxypyrimidin-4-yl)piperidin-4-yl]amine,
(64) N-methyl-N-(2-fluoro-6-chlorobenzyl)-N-[1-(6-methoxypyrimidin-4-yl)piperidin-4-yl] amine,
(65) N-methyl-N-(2-cyanobenzyl)-N-[1-(6-methoxypyrimidin-4-yl)piperidin-4-yl]amine,
(66) N-methyl-N-(p-cyanobenzyl)-N-[1-(6-methoxypyrimidin-4-yl)piperidin-4-yl]amine,
(67) N-methyl-N-(2,5-dichlorobenzyl)-N-[1-(6-methoxypyrimidin-4-yl)piperidin-4-yl] amine,
(68) N-methyl-N-(3-fluorobenzyl)-N-[1-(6-methoxypyrimidin-4-yl)piperidin-4-yl]amine,
(69) N-methyl-N-(4-cyanobenzyl)-N-[1-(2-methylthiopyrimidin-4-yl)piperidin-4-yl]amine hydrochloride,
(70) N-methyl-N-(4-cyanobenzyl)-N-[1-(2-methylthiopyrimidin-4-yl)piperidin-4-yl]amine methanesulfonate,
(71) N-methyl-N-(3-cyanobenzyl)-N-[1-(4-methoxypyrimidin-2-yl)piperidin-4-yl]amine,
(72) N-methyl-N-(3-cyanobenzyl)-N-[1-(2-methylthiopyrimidin-4-yl)piperidin-4-yl]amine,
(73) N-methyl-N-(3-cyanobenzyl)-N-[1-(2-chloropyrimidin-4-yl)piperidin-4-yl]amine,
(74) N-methyl-N-(3-cyanobenzyl)-N-[1-(4-methylthiopyrimidin-2-yl)piperidin-4-yl]amine,
(75) N-methyl-N-(3-cyanobenzyl)-N-[1-(4-chloropyrimidin-2-yl)piperidin-4-yl]amine,
(76) N-methyl-N-(4-cyanobenzyl)-N-[1-(4-chloropyrimidin-2-yl)piperidin-4-yl]amine,
(77) N-(4-cyanobenzyl)-N-[1-(2-methoxypyrimidin-4-yl)piperidin-4-yl]amine,
(78) N-methyl-N-(4-cyanobenzyl)-N-[1-(2-ethoxypyrimidin-4-yl)piperidin-4-yl]amine,
(79) N-methyl-N-(3-cyanobenzyl)-N-[1-(2-ethoxypyrimidin-4-yl)piperidin-4-yl]amine,
(80) N-methyl-N-(2-fluorobenzyl)-N-[1-(2-ethoxypyrimidin-4-yl)piperidin-4-yl]amine,
(81) N-methyl-N-(2,6-difluorobenzyl)-N-[1-(2-methoxypyrimidin-4-yl)piperidin-4-yl] amine,
(82) N-methyl-N-(2-fluorobenzyl)-N-[1-(2-methoxypyrimidin-4-yl)piperidin-4-yl]amine,
(83) N-methyl-N-(4-chlorobenzyl)-N-[1-(2-methoxypyrimidin-4-yl)piperidin-4-yl]amine,
(84) N-methyl-N-(4-chlorobenzyl)-N-[1-(2-methylthiopyrimidin-4-yl)piperidin-4-yl]amine,
(85) N-methyl-N-(2-fluorobenzyl)-N-[1-(2-methylthiopyrimidin-4-yl)piperidin-4-yl]amine,
(86) N-methyl-N-(2,6-difluorobenzyl)-N-[1-(2-methylthiopyrimidin-4-yl)piperidin-4-yl] amine,

(87) N-methyl-N-(3,5-dimethoxybenzyl)-N-[1-(2-ethoxypyrimidin-4-yl)piperidin-4-yl] amine,

(88) N-methyl-N-(2-nitrobenzyl)-N-[1-(2-ethoxypyrimidin-4-yl)piperidin-4-yl]amine,

(89) N-methyl-N-(2-nitrobenzyl)-N-[1-(2-methylthiopyrimidin-4-yl)piperidin-4-yl]amine,

(90) N-methyl-N-(2-nitrobenzyl)-N-[1-(2-methoxypyrimidin-4-yl)piperidin-4-yl]amine,

(91) N-methyl-N-(3,5-dimethoxybenzyl)-N-[1-(2-methoxypyrimidin-4-yl)piperidin-4-yl] amine,

(92) N-(2,6-dichlorobenzyl)-N-[1-(2-methoxypyrimidin-4-yl)piperidin-4-yl]amine,

(93) N-(3,5-dimethoxybenzyl)-N-[1-(2-methoxypyrimidin-4-yl)piperidin-4-yl]amine,

(94) N-(2-cyanobenzyl)-N-[1-(2-methoxypyrimidin-4-yl)piperidin-4-yl]amine,

(95) N-(2-nitrobenzyl)-N-[1-(2-methoxypyrimidin-4-yl)piperidin-4-yl]amine,

(96) N-(4-cyanobenzyl)-N-[1-(2-ethoxypyrimidin-4-yl)piperidin-4-yl]amine,

(97) N-(2,6-dichlorobenzyl)-N-[1-(2-ethoxypyrimidin-4-yl)piperidin-4-yl]amine,

(98) N-methyl-N-(4-nitrobenzyl)-N-[1-(2-ethoxypyrimidin-4-yl)piperidin-4-yl]amine,

(99) N-(2,6-difluorobenzyl)-N-[1-(2-ethoxypyrimidin-4-yl)piperidin-4-yl]amine, (100) N-methyl-N-(4-nitrobenzyl)-N-[1-(2-methoxypyrimidin-4-yl)piperidin-4-yl]amine, (101) N-methyl-N-(4-nitrobenzyl)-N-[1-(2-methylthiopyrimidin-4-yl)piperidin-4-yl]amine, (102) N-methyl-N-(naphth-1-ylmethyl)-N-[1-(2-methoxypyrimidin-4-yl)piperidin-4-yl] amine, (103) N-methyl-N-(naphth-1-ylmethyl)-N-[1-(2-ethoxypyrimidin-4-yl)piperidin-4-yl] amine, and (104) N-methyl-N-(2,6-dichlorobenzyl)-N-[1-(2-methoxypyrimidin-4-yl)piperidin-4-yl] amine.

In another aspect, the present invention provides a method for preparing the compound of formula (I) or a pharmaceutically acceptable salt thereof, which method comprises the following steps:

(1) reacting a compound of $(I_A)$

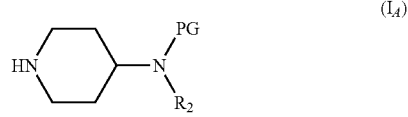

with a compound of formula $R_1$—X in a solvent (such as THF or DMF), in the presence of a base (such as potassium carbonate, sodium carbonate or sodium bicarbonate), wherein $R_1$ and $R_2$ are as defined in the above compound of formula (I), X is a halogen, and PG is a conventional amino protecting group (such as t-butoxycarbonyl or benzyloxycarbonyl), to obtain a compound of $(I_B)$;

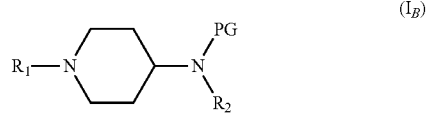

(2) deprotecting the compound of $(I_B)$, to obtain a compound of formula $(I_C)$;

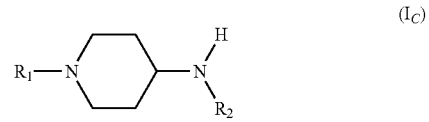

(3) reacting the compound of formula $(I_C)$ with a compound of formula $R_3$—$CH_2$—Y in a solvent (such as acetonitrile, DMF or DCM), in the presence of a base (such as potassium carbonate, sodium carbonate or sodium bicarbonate), wherein $R_3$ is as defined in the above compound of formula (I), and Y is a halogen, to obtain the compound of formula (I); and (4) optionally converting the compound of formula (I) into the pharmaceutically acceptable salt thereof.

In one embodiment shown below, an example of the method for preparing the compound of formula (I) or a pharmaceutically acceptable salt thereof according to the present invention is provided, wherein $R_1$ is substituted thiazolylmethyl, the method comprising the following reaction route:

reacting 2-chloro-5-chloromethylthiazole 1A as a starting material with tert-butyl N-methyl-N-(piperidin-4-yl)carbamate 2A or tert-butyl N-(piperidin-4-yl)carbamate 2B in a solvent such as THF or DMF under room temperature conditions, while neutralizing acid generated during the reaction using potassium carbonate, sodium carbonate or sodium bicarbonate, to obtain a compound 3A or 3C, then reacting the compound 3A with sodium methoxide, sodium ethoxide or sodium thiomethoxide in a corresponding alcohol or THF solvent under heating reflux conditions, to obtain a compound 4A, thereafter, removing BOC protecting group of the compound 4A with trifluoroacetic acid at room temperature in a solvent such as DCM, to obtaina compound 5A, and finally subjecting the compound 5A and a corresponding benzyl chloride 6A (or benzyl bromide) to substitution reaction in a solvent such as acetonitrile, DMF or DCM, in the presence of potassium carbonate, sodium carbonate or sodium bicarbonate, under heating or room temperature conditions, to obtain the compound of the present invention.

In a further embodiment, it is also possible that the compound 3A or 3C is directly subjected to the removal of BOC protecting group with trifluoroacetic acid in a solvent such as DCM to obtain a compound 5B or 5C, and then the compound 5B or 5C and a corresponding benzyl chloride 6A (or benzyl bromide) are subjected to substitution reaction in a solvent such as acetonitrile, DMF or DCM, in the presence of potassium carbonate, sodium carbonate or sodium bicarbonate, under heating or room temperature conditions, to obtain the compound of the present invention.

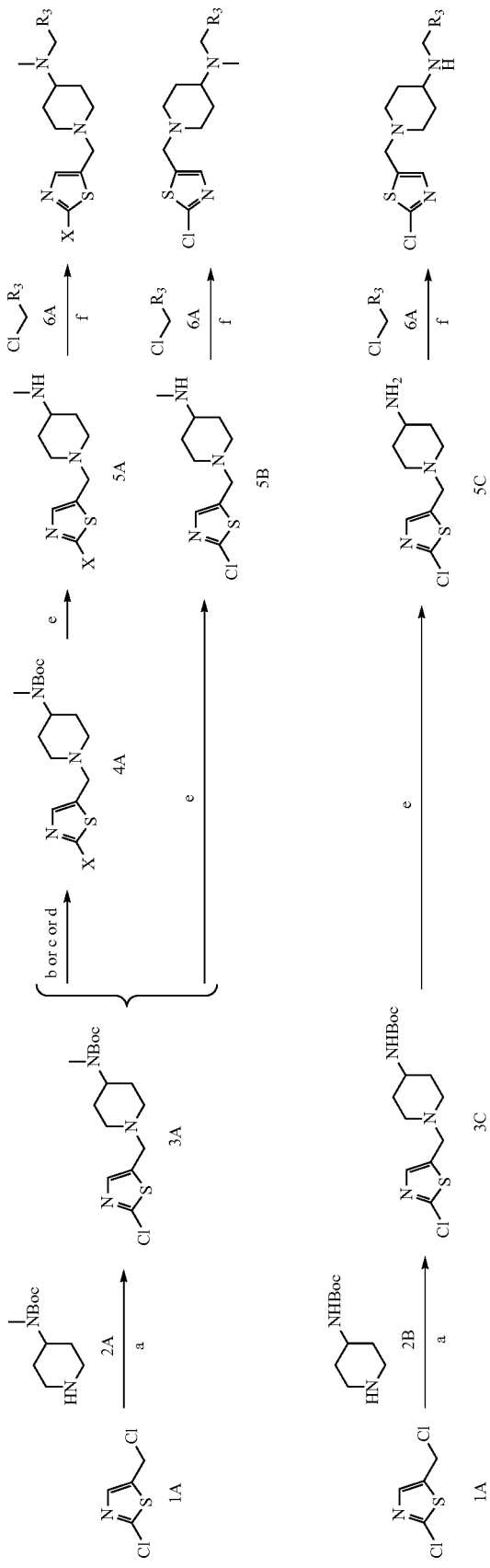
Reagents and conditions: a DMF, K₂CO₃, RT, 6 h; b CH₃ONa, MeOH, reflux, 8 h (X=CH₃O—); c CH₃CH₂ONa, MeOH, reflux, 8 h (X=CH₃CH₂O—); d CH₃SNa, KI, THF, reflux, 10 h (X=CH₃S—); e CF₃COOH, DCM, RT, 5 h; f DMF, K₂CO₃, RT, 4 h.

In another embodiment shown below, an example of the method for preparing the compound of formula (I) or a pharmaceutically acceptable salt thereof according to the present invention is provided, wherein $R_1$ is substituted pyrimidinylmethyl, the method comprising the following reaction route:

reacting 2,4-dichloropyrimidine 1B or 4,6-dichloropyrimidine 1C as a starting material with tert-butyl N-methyl-N-(piperidin-4-yl)carbamate 2A or tert-butyl N-(piperidin-4-yl)carbamate 2B in a solvent such as THF or DMF under room temperature conditions, while neutralizing acid generated during the reaction using potassium carbonate, sodium carbonate or sodium bicarbonate, to obtain a compound 3D, 3H, 3F or 3J, wherein the compounds 3D and 3F can be separated by column chromatography;

then reacting the compound 3D, 3H, 3F or 3J with sodium methoxide, sodium ethoxide or sodium thiomethoxide in a corresponding alcohol or THF solvent under heating reflux conditions, to obtain a compound 4D, 4H, 4F or 4J, thereafter, removing BOC protecting group of the compound 4D, 4H, 4F or 4J with trifluoroacetic acid at room temperature in a solvent such as DCM, to obtain a compound 5D, 5H, 5F or 5J, and finally subjecting the compound 5D, 5H, 5F or 5J and a corresponding benzyl chloride 6A (or benzyl bromide) to substitution reaction in a solvent such as acetonitrile, DMF or DCM, in the presence of potassium carbonate, sodium carbonate or sodium bicarbonate, under heating or room temperature conditions, to obtain the compound of the present invention.

In a further embodiment, it is also possible that the compound 3D, 3H, 3F or 3J is directly subjected to the removal of BOC protecting group with trifluoroacetic acid in a solvent such as DCM to obtain a compound 5C, 5G, 5I or 5K, and then the compound 5C, 5G, 5I or 5K and a corresponding benzyl chloride 6A (or benzyl bromide) are subjected to substitution reaction in a solvent such as acetonitrile, DMF or DCM, in the presence of potassium carbonate, sodium carbonate or sodium bicarbonate, under heating or room temperature conditions, to obtain the compound of the present invention.

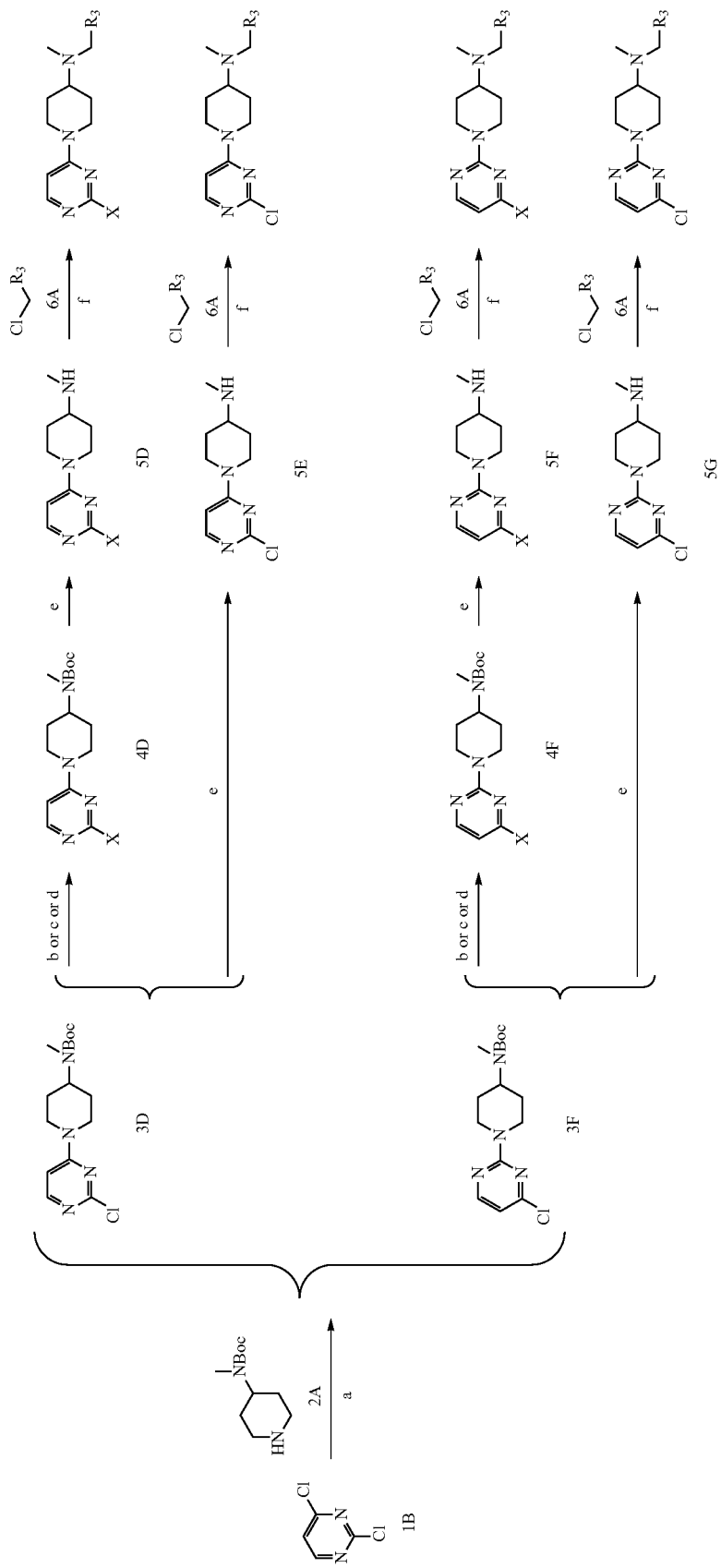

-continued
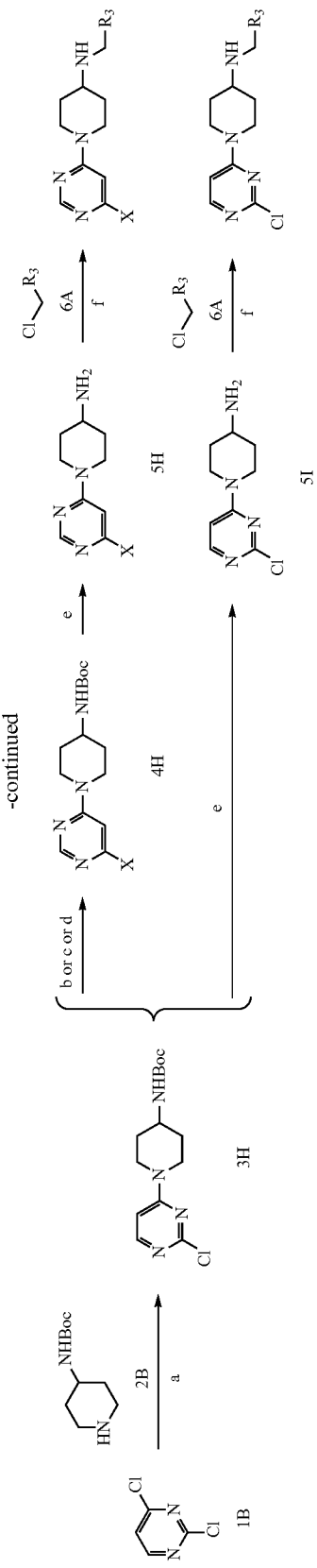
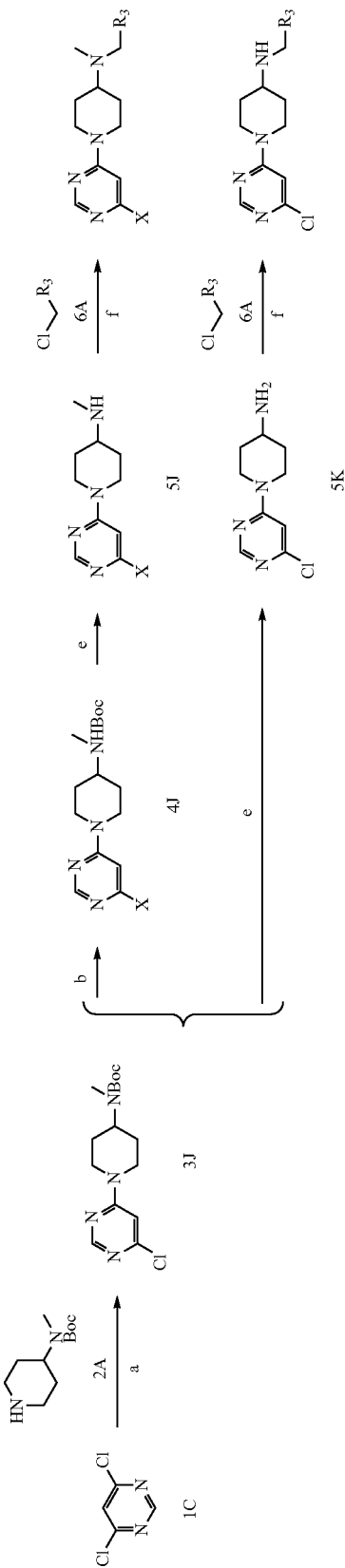
Reagents and conditions: a DMF, K₂CO₃, RT, 6 h; b CH₃ONa, MeOH, reflux, 8 h (X=CH₃O—); c CH₃CH₂ONa, MeOH, reflux, 8 h (X=CH₃CH₂O—); d CH₃SNa, KI, THF, reflux, 10 h (X=CH₃S—); e CF₃CCOOH, DCM, RT, 5 h; f DMF, K₂CO₃, RT, 4 h.

In still another aspect, the present invention provides a pharmaceutical composition comprising the above-mentioned compound of formula (I), stereoisomer, pharmaceutically acceptable salt, solvate or N-oxide thereof, and at least one pharmaceutically acceptable carrier.

In still another aspect, the present invention provides a pharmaceutical composition comprising the above-mentioned compound of formula (I), stereoisomer, pharmaceutically acceptable salt, solvate or N-oxide thereof, and one or more other antitumor drugs, for example, tinib-based antitumor drugs (such as lapatinib), and at least one pharmaceutically acceptable carrier.

In still another aspect, the present invention provides the above-mentioned compound of formula (I), stereoisomer, pharmaceutically acceptable salt, solvate or N-oxide thereof, for use as a drug for treating diseases, wherein the diseases are related to Hsp70, and are preferably selected from tumors, neurodegenerative diseases, allograft rejection and infections.

In still another aspect, the present invention provides use of the above-mentioned compound of formula (I), stereoisomer, pharmaceutically acceptable salt, solvate or N-oxide thereof in the manufacture of a drug for treating diseases, wherein the diseases are related to Hsp70, and are preferably selected from tumors, neurodegenerative diseases, allograft rejection and infections.

In still another aspect, the present invention provides a method for treating diseases, said method comprising administering to a subject especially a human in need thereof a therapeutically effective amount of the above-mentioned compound of formula (I), stereoisomer, pharmaceutically acceptable salt, solvate or N-oxide thereof, wherein the diseases are related to Hsp70, and are preferably selected from tumors, neurodegenerative diseases, allograft rejection and infections.

In some embodiments, the tumors include, but are not limited to, breast cancer, liver cancer, gastric cancer, pancreatic cancer, colorectal cancer and lung cancer.

In some embodiments, the neurodegenerative diseases include, but are not limited to, Alzheimer's disease, Huntington's disease, Parkinson's disease and spinocerebellar ataxia.

In some embodiments, the infections are selected from the group consisting of bacterial infections and viral infections.

In some embodiments, the bacterial infections are selected from the group consisting of *Staphylococcus aureus, Streptococcus mutans, Salmonella, Brucella bacterium, Helicobacter pylori, Listeria monocytogenes, Mycobacterium tuberculosis* and *Salmonella choleraesuis* infections.

In some embodiments, the viral infections are selected from the group consisting of rotavirus, papilloma virus, simian virus 40, Epstein-Barr virus, HIV, polyomavirus and papilloma virus infections.

In still another aspect, the present invention provides the above-mentioned compound of formula (I), stereoisomer, pharmaceutically acceptable salt, solvate or N-oxide thereof, for use as anti-tumor drugs, for treating tumors of a subject especially a human.

In still another aspect, the present invention provides a method of treating tumors of a subject especially a human, said method comprising administering to the subject a therapeutically effective amount of the above-mentioned compound of formula (I), stereoisomer, pharmaceutically acceptable salt, solvate or N-oxide thereof, optionally in combination with one or more other antitumor drugs, for example, tinib-based antitumor drugs (such as lapatinib).

In still another aspect, the present invention provides use of the above-mentioned compound of formula (I), stereoisomer, pharmaceutically acceptable salt, solvate or N-oxide thereof in the manufacture of a drug, wherein the drug is used for treating tumors of a subject especially a human.

In some embodiments, the tumors include, but are not limited to, breast cancer, liver cancer, gastric cancer, pancreatic cancer, colorectal cancer and lung cancer.

In still another aspect, the present invention provides the above-mentioned compound of formula (I), stereoisomer, pharmaceutically acceptable salt, solvate or N-oxide thereof, for use as drugs for treating neurodegenerative diseases, allograft rejection or infections, or for treating neurodegenerative diseases, allograft rejection or infections of a subject especially a human.

In still another aspect, the present invention provides a method for treating neurodegenerative diseases, allograft rejection or infections of a subject especially a human, said method comprising administering to the subject a therapeutically effective amount of the above-mentioned compound of formula (I), stereoisomer, pharmaceutically acceptable salt, solvate or N-oxide thereof, optionally in combination with one or more other drugs for treating neurodegenerative diseases, allograft rejection or infections of a human.

In still another aspect, the present invention provides use of the above-mentioned compound of formula (I), stereoisomer, pharmaceutically acceptable salt, solvate or N-oxide thereof in the manufacture of a drug, wherein the drug is used for treating neurodegenerative diseases, allograft rejection or infections of a subject especially a human.

In some embodiments, the neurodegenerative diseases include, but are not limited to, Alzheimer's disease, Huntington's disease, Parkinson's disease and spinocerebellar ataxia.

In some embodiments, the infections are selected from the group consisting of bacterial infections and viral infections.

In some embodiments, the bacterial infections are selected from the group consisting of *Staphylococcus aureus, Streptococcus mutans, Salmonella, Brucella bacterium, Helicobacter pylori, Listeria monocytogenes, Mycobacterium tuberculosis* and *Salmonella choleraesuis* infections.

In some embodiments, the viral infections are selected from the group consisting of rotavirus, papilloma virus, simian virus 40, Epstein-Barr virus, HIV, polyomavirus and papilloma virus infections.

The terms for describing the present invention occurred in the present application are defined as follows. As to specific terms, if the meanings thereof defined in the present application are inconsistent with the meanings thereof commonly understood by a person skilled in the art, they have the meanings as defined in the present application; if not defined in the present application, the terms have the meanings commonly understood by a person skilled in the art.

The term "alkyl" used herein refers to straight or branched chain saturated hydrocarbon group. The term "$C_{1-10}$alkyl" refers to alkyl having 1 to 10 carbon atoms. The term "$C_{1-6}$alkyl" refers to alkyl having 1 to 6, i.e. 1, 2, 3, 4, 5 or 6, carbon atoms, typically methyl, ethyl, n-propyl, isopropyl, n-butyl, isobutyl, tert-butyl, pentyl and hexyl and the like. The term "$C_{1-3}$alkyl" refers to alkyl having 1, 2 or 3 carbon atoms, i.e. methyl, ethyl, n-propyl and isopropyl. In the present invention, alkyl is preferably $C_{1-6}$alkyl, more preferably $C_{1-3}$alkyl.

The term "alkenyl" used herein refers to straight or branched chain hydrocarbon group having at least one carbon-carbon double bond. The term "$C_{2-10}$alkenyl" refers to alkenyl having 2 to 10 carbon atoms. The term "$C_{2-6}$alkenyl" refers to alkenyl having 2 to 6, i.e. 2, 3, 4, 5 or 6 carbon atoms, typically vinyl, propenyl, butenyl, pentenyl and hexenyl and the like. In the present invention, the preferred alkenyl is alkenyl having 3 to 5, i.e., 3, 4 or 5 carbon atoms.

The term "alkynyl" used herein refers to straight or branched chain hydrocarbon group having at least one carbon-carbon triple bond. The term "$C_{2-10}$alkynyl" refers to alkynyl having 2 to 10 carbon atoms. The term "$C_{2-6}$alkynyl" refers to alkynyl having 2 to 6, i.e. 2, 3, 4, 5 or 6 carbon atoms, typically ethynyl, propynyl, butynyl, pentynyl, hexynyl and the like. In the present invention, the preferred alkynyl is alkynyl having 3 to 5, i.e., 3, 4 or 5 carbon atoms.

The term "cycloalkyl" used herein refers to saturated, partially saturated or unsaturated cyclic hydrocarbon group having 3 to 10 carbon atoms and having a single ring or multiple fused rings (including fused and bridged ring systems), preferably having 3 to 8, 3 to 6, or 5 to 6 carbon atoms. Typical examples of "cycloalkyl" include, but are not limited to, single ring structure, such as cyclopropyl, cyclobutyl, cyclopentyl, cyclooctyl, 1-methylcyclopropyl, 2-methylcyclopentyl, 2-methylcyclooctyl and the like; and polycyclic structure, such as bicyclo[2.2.1]heptyl, adamantyl and the like.

The term "cycloalkylalkyl" used herein refers to alkyl as defined above which is substituted with cycloalkyl as defined above. Preferred cycloalkylalkyl is 5- or 6-membered cycloalkyl-$C_{1-3}$-alkyl, more preferred cycloalkylalkyl is cyclohexyl-$C_{1-3}$-alkyl or cyclopentyl-$C_{1-3}$-alkyl. In the present invention, examples of cycloalkylalkyl include cyclohexylmethyl, cyclohexylethyl and the like.

The term "heterocyclyl" used herein refers to 5, 6 or 7-membered heterocyclyl containing at least one and up to 4 heteroatoms independently selected from the group consisting of N, O and S, preferably having 4 to 10, i.e., 4, 5, 6, 7, 8, 9 or 10 atoms, with the proviso that the ring of the heterocyclyl does not contain two adjacent O or S atoms. The preferred heterocyclyl includes, but is not limited to, pyrrolidinyl, tetrahydrofuryl, dihydrofuryl, tetrahydrothienyl, piperidinyl, morpholinyl or piperazinyl.

The term "heterocyclylalkyl" used herein refers to alkyl as defined above which is substituted with heterocyclyl as defined above. Preferred heterocyclylalkyl is 5- or 6-membered heterocyclyl-$C_{1-3}$-alkyl, more preferred heterocyclylalkyl is tetrahydropyranyl-$C_{1-3}$-alkyl or piperidinyl-$C_{1-3}$-alkyl. In the present invention, examples of heterocyclylalkyl include tetrahydropyranylmethyl, piperidinylmethyl and the like.

The term "alkoxy" used herein refers to the group alkyl-O—. Typical examples of "alkoxy" include, but are not limited to, methoxy, ethoxy, n-propoxy, isopropoxy, n-butoxy, tert-butoxy, sec-butoxy, n-pentyloxy, n-hexyloxy, 1,2-dimethylbutoxy and the like.

The term "cycloalkyloxy" used herein refers to the group cycloalkyl-O—. Typical examples of "cycloalkyloxy" include, but are not limited to, cyclopropoxy, cyclobutoxy, cyclopentyloxy, cyclohexyloxy and the like.

The term "alkylthio" used herein refers to the group alkyl-S—. Typical examples of "alkylthio" include, but are not limited to, methylthio, ethylthio, propylthio, butylthio and the like.

The term "cycloalkylthio" used herein refers to the group cycloalkyl-S—. Typical examples of "cycloalkylthio" include, but are not limited to, cyclopropylthio, cyclobutylthio, cyclopentylthio, cyclohexylthio and the like.

The term "aryl" used herein refers to monocyclic or bicyclic hydrocarbon ring system having at least one unsaturated aromatic ring, preferably having 6 to 10, i.e., 6, 7, 8, 9 or 10 carbon atoms. In the present invention, examples of aryl include phenyl, naphthyl, 1,2,3,4-tetrahydronaphthyl and indenyl and the like.

The term "arylalkyl" used herein refers to alkyl as defined above which is substituted with aryl as defined above. Preferred arylalkyl is aryl-$C_{1-3}$alkyl, more preferred arylalkyl is phenyl-$C_{1-3}$alkyl. In the present invention, examples of arylalkyl include benzyl and phenylethyl and the like.

The term "heteroaryl" used herein refers to aryl as defined above containing at least one heteroatom independently selected from the group consisting of N, O and S, preferably having 5 to 10, i.e. 5, 6, 7, 8, 9 or 10 atoms. Examples of "heteroaryl" include, but are not limited to, thienyl, pyridyl, thiazolyl, isothiazolyl, furyl, pyrrolyl, triazolyl, imidazolyl, triazinyl, oxadiazolyl, oxazolyl, isoxazolyl, pyrazolyl, tetrazolyl, thiadiazolyl, benzimidazolyl, benzoxazolyl, benzothiazolyl, benzofuryl, benzothienyl, thioindenyl, indolyl, isoindolyl, pyridazinyl, pyrazinyl, pyrimidinyl, quinolyl, phthalazinyl, quinoxalinyl, quinazolinyl, imidazopyridyl, oxazopyridyl, thiazopyridyl, imidazopyridazinyl, oxazopyridazinyl, thiazopyridazinyl, pteridinyl, furazanyl, benzotriazolyl, pyrazopyridyl and purinyl and the like.

The term "heteroarylalkyl" used herein refers to alkyl as defined above which is substituted with heteroaryl as defined above. Preferred heteroarylalkyl is 5- or 6-membered heteroaryl-$C_{1-3}$-alkyl, more preferred heteroarylalkyl is thiazolyl-$C_{1-3}$-alkyl or pyrimidinyl-$C_{1-3}$-alkyl. In the present invention, examples of heteroarylalkyl include pyridylethyl and the like.

The term "halogen" used herein refers to fluorine, chlorine, bromine and iodine atoms.

The terms "haloalkyl", "haloalkoxy", "haloalkylthio" used herein refer to "alkyl", "alkoxy", "alkylthio" substituted with halogen.

The term "nitro" used herein refers to the group —$NO_2$.

The term "cyano" used herein refers to the group —CN.

The term "hydroxy" used herein refers to the group —OH.

The term "amino" used herein refers to the group —$NH_2$.

The above substituents in the present invention may be optionally and independently further substituted with substituents selected from the following: —F, —Cl, —Br, —I, nitro, hydroxy, amino, cyano, $C_{1-6}$alkyl, halo$C_{1-6}$alkyl, $C_{1-6}$alkylthio, halo$C_{1-6}$alkylthio, $C_{1-6}$alkoxy, halo$C_{1-6}$alkoxy, $C_{3-6}$cycloalkyl, $C_{3-6}$cycloalkyloxy, $C_{2-6}$alkenyl, $C_{2-6}$alkynyl and —$NR_4R_5$; wherein $R_4$ and $R_5$ are independently selected from the group consisting of —H, $C_{1-6}$alkyl, $C_{3-6}$cycloalkyl, $C_{2-6}$alkenyl, and $C_{2-6}$alkynyl, each optionally and independently substituted with substituents selected from the following: —F, —Cl, —Br, —I, —OH, —CN and $C_{1-6}$alkoxy; or $R_4$ and $R_5$ together with the nitrogen atom to which they are attached form a 3-8 membered heterocyclyl, optionally containing 1 to 2 oxygen atoms, said 3-8 membered heterocyclyl being optionally and independently substituted with substituents selected from the following: —F, —Cl, —Br, —I, —OH, —CN, $C_{1-6}$alkyl and $C_{1-6}$alkoxy.

The term "pharmaceutically acceptable salts" used herein refers to salts of compounds of the present invention which are pharmaceutically acceptable and have the desired pharmacological activity of the parent compounds. The salts include: acid addition salts formed with inorganic acids or organic acids, wherein the inorganic acids are such as hydrochloric acid, hydrobromic acid, sulfuric acid, nitric acid, phosphoric acid and the like; and the organic acids are such as acetic acid, propionic acid, hexanoic acid, cyclopentyl propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, benzenesulfonic acid, naphthalene sulfonic acid, camphor sulfonic acid, glucoheptonic acid, gluconic acid, glutamic acid, hydroxynaphthoic acid, salicylic acid, stearic acid, muconic acid and the like; or salts formed when acidic protons present on the parent compounds are substituted with metal ions, such as alkali metal ions or alkaline earth metal ions; or coordination compounds formed with organic base, wherein the organic base is such as ethanolamine, diethanolamine, triethanolamine, N-methyl glucosamine and the like.

The term "solvate" used herein refers to a substance formed by combining the compound of the present invention with a pharmaceutically acceptable solvent. The pharmaceutically acceptable solvent includes water, ethanol, acetic acid and the like. The solvate includes stoichiometric amount of solvate and non-stoichiometric amount of solvate, and is preferably hydrate. The compound of the present invention may be crystallized or recrystallized with water or various organic solvents. In this case, various solvates may be formed.

The term "subject" used herein includes mammals and human, preferably human.

Those skilled in the art will appreciate that the compound of the invention has stereoisomerism, for example, cis- and trans-isomers. Therefore, when the compound of the present invention is mentioned in the present specification, the compound of the present invention includes the compound of formula (I) and pharmaceutically acceptable salt, stereoisomer, solvate and N-oxide thereof. The compound of the present invention also includes active metabolite of the compound of the present invention in mammals.

The present specification illustrates in the part "Mode of carrying out the invention" the preparation method of the compound of the present invention and the anti-tumor effect of the same.

The pharmaceutical composition of the present invention comprises an effective amount of the compound of formula (I) or stereoisomer, pharmaceutically acceptable salt or solvate (such as hydrate) thereof, and one or more pharmaceutically acceptable carrier. The pharmaceutically acceptable carrier herein includes, but is not limited to: ion exchangers, alumina, aluminum stearate, lecithin, serum proteins such as human serum albumin, buffers such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, cellulose-based materials, polyethylene glycol, sodium carboxymethylcellulose, polyacrylate, beeswax, lanolin.

The pharmaceutical composition comprising the compound of the present invention can be administered according to any of the following routes: oral, spray inhalation, rectal, nasal, buccal, topical, parenteral such as subcutaneous, intravenous, intramuscular, intraperitoneal, intrathecal, intraventricular, intrasternal or intracranial injection or infusion, or by means of an explanted reservoir, wherein oral, intraperitoneal or intravenous administration route is preferred.

In the case of oral administration, the compound of the present invention may be made into any orally acceptable formulation form, including but not limited to tablets, capsules, aqueous solutions or aqueous suspensions. Wherein, the carrier used in tablets generally includes lactose and corn starch, additionally, a lubricant such as magnesium stearate may also be added. The diluent used in capsules generally includes lactose and dried corn starch. Aqueous suspensions are generally used by mixing active ingredient with suitable emulsifier and suspending agent. If desired, some sweetening agents, flavoring agents or coloring agents may also be added in the above oral formulation forms.

In the case of topical administration, especially for the treatment of affected surfaces or organs where topical application is easy to reach, such as eyes, skin, or lower intestinal neurological diseases, the compound of the present invention may be made into different topical formulation forms according to different affected surfaces or organs, which are specifically described as follows:

In the case of topical ocular administration, the compound of the present invention may be formulated into the formulation form of micronised suspension or solution, and the carrier used is isotonic sterile saline at a certain pH, in which a preservative such as benzyl chloride alkoxide may be added or not. For ocular administration, the compound may also be made into an ointment form such as vaseline ointment.

In the case of topical dermal administration, the compound of the present invention may be made into suitable formulation forms of ointments, lotions or creams, wherein active ingredient is suspended or dissolved in one or more carriers. The carrier that may be used in ointments includes, but is not limited to: mineral oil, liquid petrolatum, white petrolatum, propylene glycol, polyoxyethylene, polyoxypropylene, emulsifying wax and water; the carrier that may be used in lotions or creams includes, but is not limited to: mineral oil, sorbitan monostearate, Tween 60, cetyl wax, hexadecene aromatic alcohols, 2-octyldodecanol, benzyl alcohol and water.

The compound of the present invention may also be administered in sterile injectable formulation forms, including sterile injectable aqueous or oil suspensions or sterile injectable solutions. The carrier and solvent that may be used therein include water, Ringer's solution and isotonic sodium chloride solution. In addition, sterile non-volatile oils, such as mono- or diglycerides, may also be used as solvent or suspending medium.

The dose of the compound of the present invention administered to the subject depends on the type and severity of the disease or condition and the characteristics of the subject, for example, general health condition, age, gender, body weight and tolerance to drugs, and also depends on the type of formulation and the administration route of drug, and the period or interval of administration, etc. Those skilled in the art can determine an appropriate dose according to these factors and other factors. Generally, the daily dose of the compound of the present invention useful for treating tumor may be about 1-800 mg, and this daily dose may be administered one or more times according to the specific condition. The compound of the present invention may be provided in dosage unit, and the content of the compound in the dosage unit may be 0.1-200 mg, e.g., 1-100 mg.

Instrument for measuring the affinity between Example compounds and Hsp70 is BIACORE T100 Biomolecular Interaction Analysis (GE, USA), and the positive control drug is VER-155008 that is well-recognized as Hsp70 inhibitor now, and, on the basis of the measured results, according to binding characteristics between the compounds and protein, the binding constant (equilibrium dissociation constant KD) between drugs and protein is calculated by selecting steady state model with the formula: Conc*Rmax/[conc+KD]+offset. Finally, it is found that the compounds of Example 12, Example 14, Example 35, Example 36, Example 57 have KD values equivalent to that of the positive control drug VER-155008, which illustrates that the affinity between these Example compounds and Hsp70 is equivalent to the affinity between the positive control drug and Hsp70.

In antitumor activity evaluation, six human breast cancer cell strains are selected, including BT474, SK-BR3 which are human breast cancer cell strains sensitive to lapatinib, BT/Lap$^R$1.0, SK/Lap$^R$1.0 which are human breast cancer cell strains with secondary resistance to lapatinib, MDA-MB-361, MDA-MB-453 which are human breast cancer cell strains with natural resistance to lapatinib. The results show that the compounds of Example 36, Example 37, Example 40, Example 47, Example 49 each alone exhibit relatively significant growth inhibition to the six human breast cancer cell strains used in the experiment. The compound of Example 36 has an IC$_{50}$ of 1.41 μM to the human breast cancer cell strain BT474 sensitive to lapatinib, and has an IC$_{50}$ of 1.41 μM to the human breast cancer cell strain BT/Lap$^R$1.0 with secondary resistance to lapatinib.

In mice pharmacokinetic evaluation of the compound of Example 36, after intragastric administration to mice of 10 mg/kg of the compound of Example 36, the following results are obtained: C$_{max}$=260.28±63.19 ng/mL, peak time T$_{max}$=0.44±0.49 h, half-life T$_{1/2}$=2.72±2.47 h. Absolute bioavailability is 55.51±10.90%. It demonstrates that, after intragastric administration to mice, in vivo absorption and elimination of the compound both are faster, with the nature of medicine.

In acute toxicity experiment with single intragastric administration to mice of the compound of Example 36, it is calculated using SAS software package that the LD$_{50}$ and 95% confidence limit of the compound of Example 36 are 869.0 (776.5-969.4) mg/kg. It demonstrates that the compound of Example 36 has drug-like properties.

In extended test of the compounds of Examples 36/37/40/47/49 against tumor cell lines, it is found that the compounds of Examples 36/49 exhibit certain inhibition and cytotoxicity to either tumor cells or normal cells, without significant difference. The compounds of Examples 37/40/47 exhibit slightly stronger inhibition to liver cancer than that to other tumor cells, and exhibit cytotoxicity to normal cells lower than inhibition to tumor cells. Among them, the compound of Example 47 has effect superior to that of the compounds of other Examples.

MODE OF CARRYING OUT THE INVENTION

Figure 1:
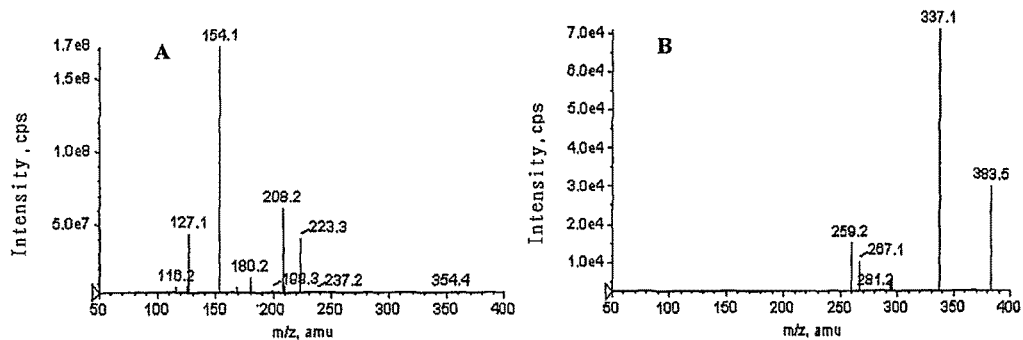
FIG. 1: Secondary mass spectrums of the compound of Example 36 and loratadine. A: the compound of Example 36; B: loratadine (internal standard).
Figure 2:
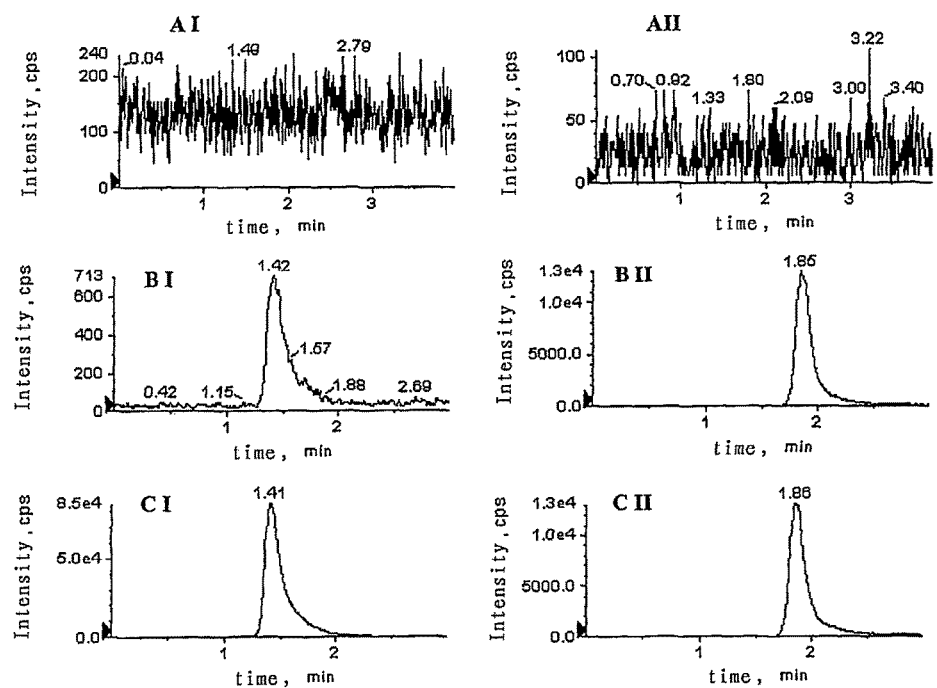
FIG. 2: MRM chromatograms of the compound of Example 36 in mouse plasma samples: A: blank plasma; B: standard added blank plasma; C: drug administered plasma sample. Peak I: Mol; Peak II: Internal standard.
Figure 3:
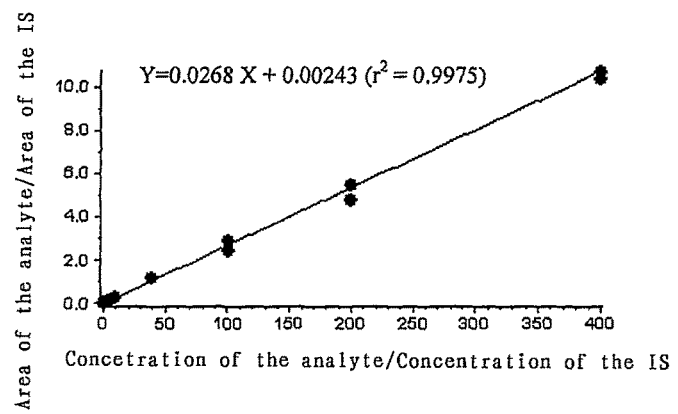
FIG. 3: A standard curve of the compound of Example 36 at sample measurement stage.

The following specific examples are preferred embodiments of the present invention, which should not be construed as constituting any limitation to the present invention.

Melting point of the compound is measured using RY-1 melting point apparatus, with thermometer not corrected. Mass spectrum is measured using Micromass ZabSpec high resolution mass spectrometer (resolution 1000). $^1$H NMR is measured using JNM-ECA-400 superconducting NMR instrument, working frequency $^1$H NMR 300 MHz, $^{13}$C NMR 100 MHz.

EXAMPLE 1

N-methyl-N-m-chlorobenzyl-N-{1-[(2-ethoxythiazol-5-yl)methyl]piperidin-4-yl}amine (Mol-Hsp70-217)

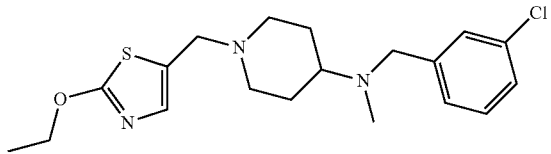 [SMILES: CCOc1ncc(CN2CCC(N(C)Cc3cccc(Cl)c3)CC2)s1]

50 g of 2-chloro-5-chloromethylthiazole was added to a 1000 ml three-necked flask, and dissolved with 300 ml of DMF. Thereafter, 49.3 g of anhydrous K$_2$CO$_3$ was added, and 76.5 g of tert-butyl N-methyl-N-(piperidin-4-yl)carbamate was added under stirring, followed by stirring at room temperature for 6 h, till the reaction was complete as monitored by TLC. Under stirring, a large amount of ice water was added to the reaction mixture. The solid was precipitated and filtered, and the filter cake was washed with a large amount of petroleum ether, and then the filter cake was dried to obtain 92.7 g of a white powder tert-butyl N-methyl-N-{1-[(2-chlorothiazol-5-yl)methyl]piperidin-4-yl}carbamate (A).

20 g of the compound (A) was added to a 250 ml three-necked flask, and dissolved with 100 ml of anhydrous ethanol. Thereafter, 12.7 g of sodium ethoxide was added and the reaction mixture was heated to reflux, followed by reacting for 8 h, till the reaction was complete as monitored by TLC. The reaction mixture was cooled to room temperature, and subjected to distillation under reduced pressure in water bath of 50° C. The resulting residue was dissolved with water and extracted with ethyl acetate. The ethyl acetate phase was dried over anhydrous MgSO$_4$ and filtered. The filter residue was washed with a small amount of ethyl acetate, and then the combined filtrate and washings was subjected to distillation under reduced pressure in water bath of 45° C., to obtain 18 g of a colorless oily compound tert-butyl N-methyl-N-{1-[(2-ethoxythiazol-5-yl)methyl]piperidin-4-yl}carbamate.

10 g of the product resulted from the above step was added to a 100 ml single neck round-bottom flask, and dissolved with 50 ml of DCM. Thereafter, an excess of trifluoroacetic acid was added under ice bath, followed by stirring at room temperature, till the raw material disappeared as monitored by TLC (take a small amount of the reaction mixture, add water, make it basic with $K_2CO_3$, and analyze the DCM phase with thin-layer chromatography), and then the reaction was stopped. The reaction mixture was made basic with saturated aqueous $K_2CO_3$ solution, and extracted three times with 50 ml of water. The organic phase was collected, and subjected to distillation under reduced pressure to obtain 6.2 g of a yellow oily compound N-methyl-N-{1-[(2-ethoxythiazol-5-yl)methyl]piperidin-4-yl}amine.

0.3 g of the resulting compound was added to a 25 ml single neck round-bottom flask, and dissolved with 5 ml of DMF. Thereafter, 0.3 g of anhydrous $K_2CO_3$ was added with stirring, and finally 0.2 g of m-chlorobenzyl chloride was added, followed by reacting at room temperature for 4 h, till the reaction was complete as monitored by TLC, and then water was added to stop the reaction. The reaction mixture was extracted with DCM, and the DCM phase was separated with thin-layer chromatography. The product band silica gel was scraped off, soaked with anhydrous DCM, and filtered. The filter residue was washed with a small amount of DCM, and the combined filtrate and washings was subjected to distillation under reduced pressure in water bath of 30° C. to obtain 161 mg of a colorless oily product.

$^1$H-NMR (300 MHz, $CDCl_3$-d): δ 1.461-1.426 (t, J=7.2 Hz, 3H); 1.674-1.636 (m, 2H); 1.823-1.793 (m, 2H); 2.033-1.979 (m, 2H); 2.209 (s, 3H); 2.444 (m, 1H); 3.014-2.985 (m, 2H); 3.562 (s, 4H); 4.462-4.409 (q, J=7.2 Hz, 2H); 6.904 (s, 1H); 7.348-7.215 (m, 4H). MS (TOF) 379.9 (M+).

EXAMPLE 2

N-methyl-N-o-cyanobenzyl-N-{1-[(2-ethoxythiazol-5-yl)methyl]piperidin-4-yl}amine (Mol-Hsp70-224)

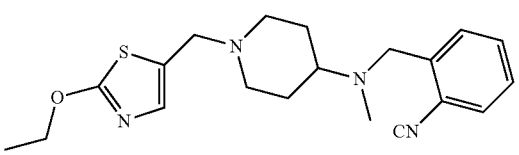

The method of Example 1 was carried out, except for the use of o-cyanobenzylchloride in place of m-chlorobenzyl chloride, to obtain 150 mg of a colorless oily product, yield 34.09%.

$^1$H-NMR (300 MHz, $CDCl_3$-d): δ 1.454-1.419 (t, 3H); 1.702-1.693 (m, 2H); 1.823 (m, 2H); 2.016 (m, 2H); 2.216 (s, 3H); 2.507 (m, 1H); 3.022-2.993 (m, 2H); 3.562 (s, 2H); 3.783 (s, 2H); 4.455-4.402 (q, 2H); 6.900 (s, 1H); 7.644-7.284 (m, 4H). MS (TOF) 370.5 (M+).

EXAMPLE 3

N-methyl-N-(3,4-dichlorobenzyl)-N-{1-[(2-ethoxythiazol-5-yl)methyl]piperidin-4-yl}amine (Mol-Hsp70-215)

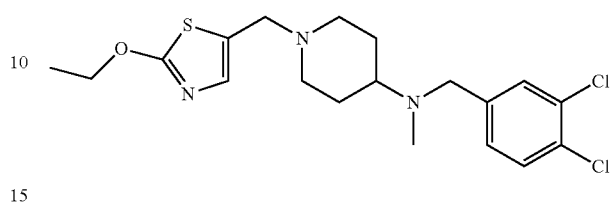

The method of Example 1 was carried out, except for the use of 3,4-dichlorobenzyl chloride in place of m-chlorobenzyl chloride, to obtain 150 mg of a colorless oily product.

$^1$H-NMR (300 MHz, $CDCl_3$-d): δ 1.42-1.46 (t, 3H); 1.63-1.66 (m, 2H); 1.77-1.80 (d, 2H); 2.00 (t, 2H); 2.20 (s, 3H); 2.43 (m, 1H); 2.98-3.01 (d, 2H); 2.53-3.56 (d, 4H); 4.41-4.46 (m, 2H); 6.90 (s, 1H); 7.15-7.18 (dd, 1H); 7.37-7.39 (d, 2H); 7.44-7.75 (d, 1H). MS (TOF) 414 (M+).

EXAMPLE 4

N-methyl-N-(4-cyanobenzyl)-N-{1-[(2-ethoxythiazol-5-yl)methyl]piperidin-4-yl}amine (Mol-Hsp70-218)

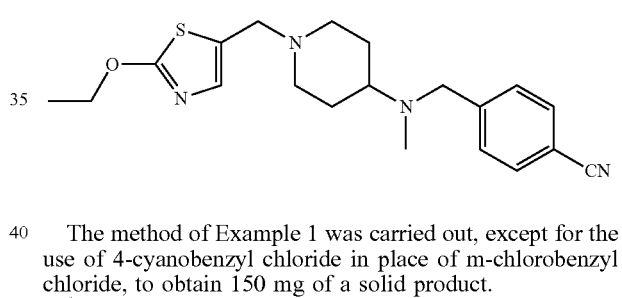

The method of Example 1 was carried out, except for the use of 4-cyanobenzyl chloride in place of m-chlorobenzyl chloride, to obtain 150 mg of a solid product.

$^1$H-NMR (300 MHz, $CDCl_3$-d): δ 1.42-1.46 (t, 3H); 1.63-1.67 (m, 2H); 1.77-1.81 (d, 2H); 1.98-2.03 (t, 2H); 2.20 (s, 3H); 2.43 (m, 1H); 2.98-3.01 (d, 2H); 3.56-3.63 (d, 4H); 4.40-4.46 (m, 2H); 6.90 (s, 1H); 7.44-7.46 (d, 2H); 7.60-7.62 (d, 2H). MS (TOF) 370.5 (M+).

EXAMPLE 5

N-methyl-N-(2-fluoro-6-chlorobenzyl)-N-{1-[(2-ethoxythiazol-5-yl)methyl]piperidin-4-yl} amine (Mol-Hsp70-226)

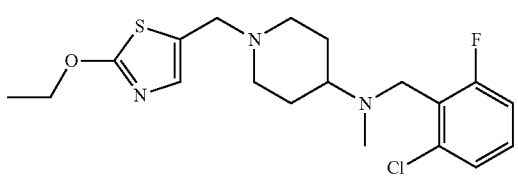 [SMILES: CCOc1ncc(CN2CCC(N(C)Cc3c(F)cccc3Cl)CC2)s1]

The method of Example 1 was carried out, except for the use of 2-fluoro-6-chlorobenzyl chloride in place of m-chlorobenzyl chloride, to obtain 130 mg of a colorless oily product.

¹H-NMR (300 MHz, CDCl₃-d): δ 1.43-1.46 (t, 3H); 1.72-1.75 (m, 2H); 1.84-1.87 (d, 2H); 2.00-2.03 (t, 2H); 2.26 (s, 3H); 2.53 (m, 1H); 3.01-3.04 (d, 2H); 3.58 (s, 2H); 3.73 (s, 2H); 4.41-4.46 (m, 2H); 6.91 (s, 1H); 6.98-6.99 (m, 1H); 7.18-7.28 (m, 2H). MS (TOF) 397.9 (M+).

EXAMPLE 6

N-methyl-N-(2-chlorobenzyl)-N-{1-[(2-ethoxythiazol-5-yl)methyl]piperidin-4-yl}amine (Mol-Hsp70-230)

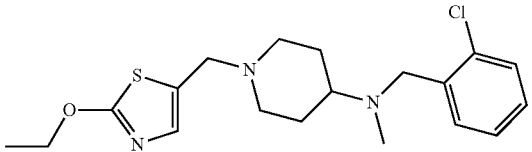 [SMILES: CCOc1ncc(CN2CCC(N(C)Cc3ccccc3Cl)CC2)s1]

The method of Example 1 was carried out, except for the use of 2-chlorobenzyl chloride in place of m-chlorobenzyl chloride, to obtain 140 mg of a solid product.

¹H-NMR (300 MHz, CDCl₃-d): δ 1.42-1.46 (t, 3H); 1.67-1.71 (m, 2H); 1.82-1.85 (d, 2H); 1.99-2.04 (t, 2H); 2.26 (s, 3H); 2.49 (m, 1H); 2.99-3.02 (d, 2H); 3.56 (s, 2H); 3.70 (s, 2H); 4.41-4.46 (m, 2H); 6.91 (s, 1H); 7.17-7.20 (m, 1H); 7.22-7.24 (m, 1H); 7.22-7.24 (m, 1H); 7.33-7.35 (dd, 1H); 7.49 (dd, 1H). MS (TOF) 379.9 (M+).

EXAMPLE 7

N-methyl-N-(4-fluorobenzyl)-N-{[1-(2-ethoxythiazol-5-yl)methyl]piperidin-4-yl}amine (Mol-Hsp70-300)

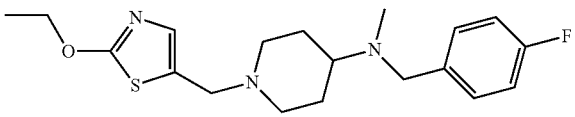 [SMILES: CCOc1ncc(CN2CCC(N(C)Cc3ccc(F)cc3)CC2)s1]

The method of Example 1 was carried out, except for the use of 4-fluorobenzyl chloride in place of m-chlorobenzyl chloride, to obtain 145 mg of a solid product.

¹H-NMR (300 MHz, CDCl₃-d): δ 1.42-1.46 (t, 3H); 1.68-1.69 (m, 2H); 1.80 (d, 2H); 1.98-2.03 (t, 2H); 2.21 (s, 3H); 2.45 (m, 1H); 2.98-3.01 (d, 2H); 3.56 (s, 4H); 4.41-4.46 (m, 2H); 6.90 (s, 1H); 6.98-7.03 (t, 2H); 7.28-7.30 (d, 2H). MS (TOF) 363.5 (M+).

EXAMPLE 8

N-methyl-N-(2,4-dichlorobenzyl)-N-{[1-(2-ethoxythiazol-5-yl)methyl]piperidin-4-yl}amine (Mol-Hsp70-313)

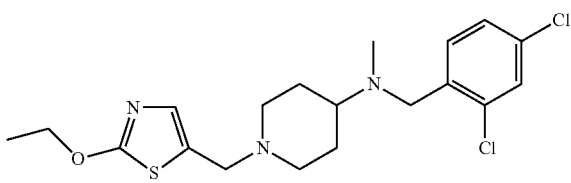 [SMILES: CCOc1ncc(CN2CCC(N(C)Cc3ccc(Cl)cc3Cl)CC2)s1]

The method of Example 1 was carried out, except for the use of 2,4-dichlorobenzyl chloride in place of m-chlorobenzyl chloride, to obtain 153 mg of a solid product.

¹H-NMR (300 MHz, CDCl₃-d): δ 1.42-1.46 (t, 3H); 1.61-1.69 (m, 2H); 1.80-1.83 (d, 2H); 1.99-2.04 (t, 2H); 2.24 (s, 3H); 2.47 (m, 1H); 2.99-3.02 (d, 2H); 3.57 (s, 2H); 3.65 (s, 2H); 4.41-4.46 (m, 2H); 6.91 (s, 1H); 7.21-7.23 (dd, 1H); 7.36 (d, 1H); 7.45 (d, 1H). MS (TOF) 414.4 (M+).

EXAMPLE 9

N-methyl-N-(2,6-dichlorobenzyl)-N-{[1-(2-ethoxythiazol-5-yl)methyl]piperidin-4-yl}amine (Mol-Hsp70-301)

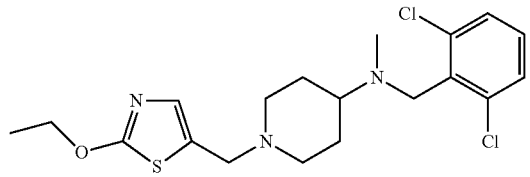 [SMILES: CCOc1ncc(CN2CCC(N(C)Cc3c(Cl)cccc3Cl)CC2)s1]

The method of Example 1 was carried out, except for the use of 2,6-dichlorobenzyl chloride in place of m-chlorobenzyl chloride, to obtain 153 mg of a solid product.

¹H-NMR (300 MHz, CDCl₃-d): δ 1.42-1.46 (t, 3H); 1.78-1.84 (m, 4H); 2.05 (m, 2H); 2.26 (s, 3H); 2.56 (m, 1H); 3.01-3.06 (m, 2H); 3.59 (m, 2H); 3.85 (s, 2H); 4.43-4.45 (m, 2H); 6.92 (s, 1H); 7.14-7.16 (m, 1H); 7.30-7.31 (m, 3H). MS (TOF) 414.4 (M+).

EXAMPLE 10

N-methyl-N-(2,5-dichlorobenzyl)-N-{[1-(2-ethoxythiazol-5-yl)methyl]piperidin-4-yl}amine (Mol-Hsp70-314)

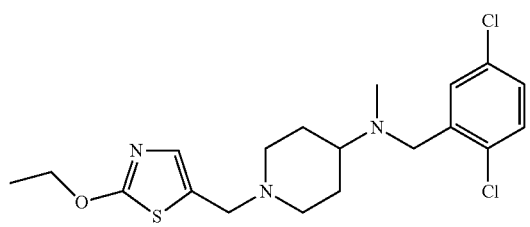 [SMILES: CCOc1ncc(CN2CCC(N(C)Cc3cc(Cl)ccc3Cl)CC2)s1]

The method of Example 1 was carried out, except for the use of 2,5-dichlorobenzyl chloride in place of m-chlorobenzyl chloride, to obtain 153 mg of a solid product.

¹H-NMR (300 MHz, CDCl₃-d): δ 1.42-1.44 (t, 3H); 1.66-1.69 (m, 2H); 1.81 (m, 2H); 2.02 (m, 2H); 2.26 (s, 3H); 2.48 (m, 1H); 3.00-3.03 (m, 2H); 3.58 (s, 1H); 3.65 (s, 1H); 4.09-4.46 (m, 2H); 6.92 (s, 1H); 7.16-7.17 (m, 1H); 7.27-7.28 (m, 1H); 7.54 (s, 3H). MS (TOF) 414.4 (M+).

EXAMPLE 11

N-(3,4-dichlorobenzyl)-N-{1-[(2-chlorothiazol-5-yl)methyl]piperidin-4-yl}amine (Mol-Hsp70-223)

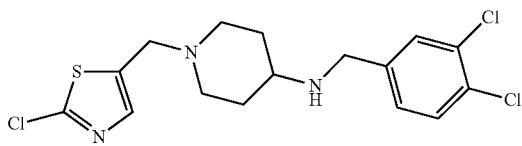 [SMILES: Clc1ncc(CN2CCC(NCc3ccc(Cl)c(Cl)c3)CC2)s1]

According to the first step in Example 1, 2-chloro-5-chloromethylthiazole and tert-butyl N-(piperidin-4-yl)carbamate were reacted, to obtain tert-butyl N-{1-[(2-chlorothiazol-5-yl)methyl]piperidin-4-yl}carbamate.

10 g of the resulting compound was added to a 250 ml single neck round-bottom flask, and dissolved with 50 ml of anhydrous dichloromethane. Thereafter, an excess of trifluoroacetic acid was added under ice bath, followed by stirring at room temperature, till the raw material disappeared as monitored by TLC (take a small amount of the reaction mixture, add water, make it basic with $K_2CO_3$, and analyze the DCM phase with thin-layer chromatography), and then the reaction was stopped. The reaction mixture was made basic with saturated aqueous $K_2CO_3$ solution, and extracted three times with 50 ml of water. The organic phase was collected, and subjected to distillation under reduced pressure to obtain 6 g of a white powdery compound N-{1-[(2-chlorothiazol-5-yl)methyl]piperidin-4-yl}amine, yield 68.18%.

5 g of the resulting compound was added to a 100 ml single neck round-bottom flask, and dissolved with 30 ml of DMF. Thereafter, 0.3 g of anhydrous $K_2CO_3$ was added with stirring, and finally 4.7 g of 3,4-dichlorobenzyl chloride was added slowly, followed by reacting at room temperature for 4 h, till the reaction was complete as monitored by TLC, and then water was added to stop the reaction. The reaction mixture was extracted with DCM, and the DCM phase was dried over anhydrous $MgSO_4$ and filtered. The filter residue was washed with a small amount of DCM, and the combined filtrate and washings was subjected to distillation under reduced pressure in water bath of 30° C. to obtain a yellow oily crude product. The crude product was mixed with silica gel, and separated through a chromatographic column, to obtain 4.0 g of a white powdery product.

$^1$H-NMR (300 MHz, $CDCl_3$-d): δ 1.44-1.45 (m, 2H); 1.871 (m, 2H); 2.09-2.10 (d, 2H); 2.51 (m, 1H); 2.86-2.89 (d, 2H); 3.64-3.65 (d, 2H); 3.78 (s, 2H); 7.17-7.19 (dd, 1H); 7.34 (s, 1H); 7.38-7.41 (d, 1H); 7.46 (d, 1H). MS (TOF) 390.8 (M+).

EXAMPLE 12

N-(4-fluorobenzyl)-N-{1-[(2-chlorothiazol-5-yl)methyl]piperidin-4-yl}amine (Mol-Hsp70-219)

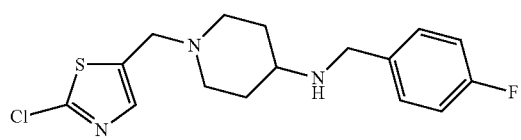 [SMILES: Fc1ccc(CNC2CCN(Cc3cnc(Cl)s3)CC2)cc1]

The method of Example 11 was carried out, except for the use of p-fluorobenzyl chloride in place of 3,4-dichlorobenzyl chloride, to obtain 135 mg of a solid product.

$^1$H-NMR (300 MHz, $CDCl_3$-d): δ 1.46-1.51 (m, 2H); 1.89-1.92 (m, 2H); 2.05-2.12 (d, 2H); 2.54-2.56 (m, 1H); 2.87-2.90 (d, 2H); 3.64 (s, 2H); 3.80 (s, 2H); 6.99-7.04 (m, 2H); 7.31-7.34 (d, 3H). MS (TOF) 339.9 (M+).

EXAMPLE 13

N-(3-chlorobenzyl)-N-{1-[(2-chlorothiazol-5-yl)methyl]piperidin-4-yl}amine (Mol-Hsp70-225)

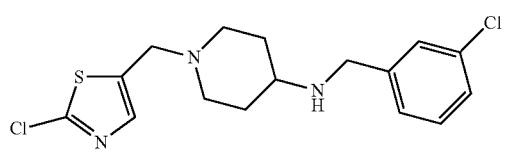 [SMILES: Clc1cccc(CNC2CCN(Cc3cnc(Cl)s3)CC2)c1]

The method of Example 11 was carried out, except for the use of m-chlorobenzyl chloride in place of 3,4-dichlorobenzyl chloride, to obtain 137 mg of a solid product.

$^1$H-NMR (300 MHz, $CDCl_3$-d): δ 1.43-1.46 (m, 2H); 1.88-1.92 (m, 2H); 2.07-2.13 (m, 2H); 2.53 (m, 1H); 2.86-2.90 (d, 2H); 3.64 (s, 2H); 3.81 (s, 2H); 7.21-7.26 (m, 3H); 7.34-7.35 (m, 2H). MS (TOF) 356.3 (M+).

EXAMPLE 14

N-methyl-N-(2-cyanobenzyl)-N-{1-[(2-chlorothiazol-5-yl)methyl]piperidin-4-yl}amine (Mol-Hsp70-243)

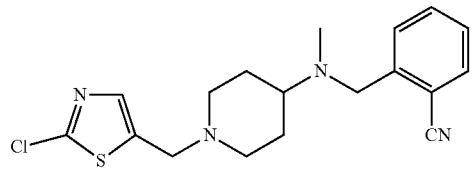 [SMILES: CN(Cc1ccccc1C#N)C1CCN(Cc2cnc(Cl)s2)CC1]

10 g of the compound (A) was added to a 250 ml single neck round-bottom flask, and dissolved with 80 ml of DCM. Thereafter, an excess of trifluoroacetic acid was added under ice bath, followed by stirring at room temperature, till the raw material disappeared as monitored by TLC (take a small amount of the reaction mixture, add water, make it basic with $K_2CO_3$, and analyze the DCM phase with thin-layer chromatography), and then the reaction was stopped. The reaction mixture was made basic with saturated aqueous $K_2CO_3$ solution, and extracted three times with 50 ml of water. The organic phase was collected, and subjected to distillation under reduced pressure to obtain 7.5 g of a yellow oily compound N-methyl-N-{1-[(2-chlorothiazol-5-yl)methyl]piperidin-4-yl}amine, yield 72.12%.

0.5 g of the resulting compound was added to a 25 ml single neck round-bottom flask, and dissolved with 10 ml of DMF. Thereafter, 0.22 g of anhydrous $K_2CO_3$ was added, and finally 0.3 g of 2-cyanobenzyl chloride was added, followed by stirring at room temperature for 4 h, till the reaction was complete as monitored by TLC, and then water was added to stop the reaction. The reaction mixture was extracted with DCM, and the DCM phase was separated with thin-layer chromatography. The product band silica gel was scraped off, soaked with anhydrous DCM, and filtered. The filter residue was washed with a small amount of DCM, and the combined filtrate and washings was subjected to distillation under reduced pressure in water bath of 30° C. to obtain 255 mg of a colorless oily product, yield 48.29%.

$^1$H-NMR (300 MHz, CDCl$_3$-d): δ 1.66-1.70 (m, 2H); 1.84-1.87 (d, 2H); 2.03-2.09 (t, 2H); 2.22 (s, 3H); 2.52 (m, 1H); 2.98-3.01 (d, 2H); 3.65 (s, 2H); 3.79 (s, 2H); 7.34-7.37 (m, 2H); 7.55-7.57 (d, 2H); 7.63-7.65 (d, 2H). MS (TOF) 360.9 (M+).

EXAMPLE 15

N-methyl-N-(4-cyanobenzyl)-N-{1-[(2-chlorothiazol-5-yl)methyl]piperidin-4-yl}amine (Mol-Hsp70-244)

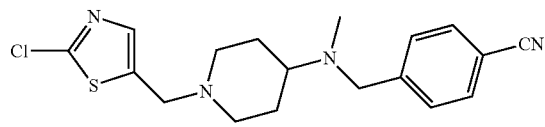 [SMILES: CN(Cc1ccc(C#N)cc1)C1CCN(Cc2cnc(Cl)s2)CC1]

The method of Example 14 was carried out, except for the use of p-cyanobenzyl chloride in place of 2-cyanobenzyl chloride, to obtain 234 mg of a solid product.

$^1$H-NMR (300 MHz, CDCl$_3$-d): δ 1.62-1.66 (m, 2H); 1.78-1.81 (d, 2H); 1.99-2.05 (t, 2H); 2.18 (s, 3H); 2.43 (m, 1H); 2.69 (s, 3H); 2.69-3.00 (d, 2H); 3.62-3.67 (d, 4H); 7.41 (s, 1H); 7.44-7.46 (d, 2H); 7.60-7.62 (d, 2H). MS (TOF) 360.9 (M+).

EXAMPLE 16

N-methyl-N-(4-fluorobenzyl)-N-{1-[(2-chlorothiazol-5-yl)methyl]piperidin-4-yl}amine (Mol-Hsp70-245)

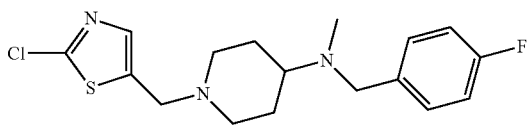 [SMILES: CN(Cc1ccc(F)cc1)C1CCN(Cc2cnc(Cl)s2)CC1]

The method of Example 14 was carried out, except for the use of 4-fluorobenzyl chloride in place of 2-cyanobenzyl chloride, to obtain 223 mg of a solid product.

$^1$H-NMR (300 MHz, CDCl$_3$-d): δ 1.64-1.71 (m, 2H); 1.80-1.83 (d, 2H); 2.01-2.07 (t, 2H); 2.20 (s, 3H); 2.45 (m, 1H); 2.97-3.00 (d, 2H); 3.56 (s, 2H); 3.65 (s, 2H); 6.98-7.03 (t, 2H); 7.27-7.316 (m, 2H); 7.34 (s, 1H). MS (TOF) 353.9 (M+).

EXAMPLE 17

N-methyl-N-(3,4-dichlorobenzyl)-N-{1-[(2-chlorothiazol-5-yl)methyl]piperidin-4-yl}amine (Mol-Hsp70-246)

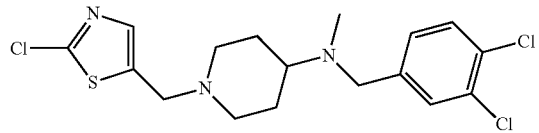 [SMILES: CN(Cc1ccc(Cl)c(Cl)c1)C1CCN(Cc2cnc(Cl)s2)CC1]

The method of Example 14 was carried out, except for the use of 3,4-dichlorobenzyl chloride in place of 2-cyanobenzyl chloride, to obtain 221 mg of a solid product.

$^1$H-NMR (300 MHz, CDCl$_3$-d): δ 1.62-1.69 (m, 2H); 1.80-1.82 (d, 2H); 2.01-2.07 (t, 2H); 2.20 (s, 3H); 2.44 (m, 1H); 2.97-3.00 (d, 2H); 3.54 (s, 2H); 3.65 (s, 2H); 7.16-7.18 (d, 1H); 7.35-7.39 (m, 2H); 7.45 (d, 1H). MS (TOF) 404.8 (M+).

EXAMPLE 18

N-methyl-N-(3-chlorobenzyl)-N-{1-[(2-chlorothiazol-5-yl)methyl]piperidin-4-yl}amine (Mol-Hsp70-247)

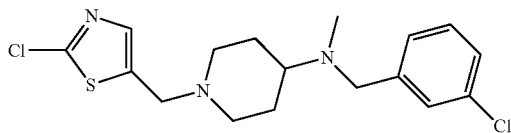 [SMILES: CN(Cc1cccc(Cl)c1)C1CCN(Cc2cnc(Cl)s2)CC1]

The method of Example 14 was carried out, except for the use of m-chlorobenzyl chloride in place of 2-cyanobenzyl chloride, to obtain 210 mg of a solid product.

$^1$H-NMR (300 MHz, CDCl$_3$-d): δ 1.64-1.71 (m, 2H); 1.82-1.85 (d, 2H); 2.02-2.08 (t, 2H); 2.22 (s, 3H); 2.47 (m, 1H); 2.97-3.00 (d, 2H); 3.60 (s, 2H); 3.65 (s, 2H); 7.23 (m, 3H); 7.35-7.36 (m, 2H). MS (TOF) 370.3 (M+).

EXAMPLE 19

N-methyl-N-(2-fluoro-6-chlorobenzyl)-N-{[1-(2-chlorothiazol-5-yl)methyl]piperidin-4-yl}amine (Mol-Hsp70-299)

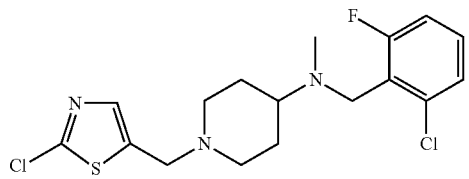 [SMILES: CN(Cc1c(F)cccc1Cl)C1CCN(Cc2cnc(Cl)s2)CC1]

The method of Example 14 was carried out, except for the use of 2-fluoro-6-chlorobenzyl chloride in place of 2-cyanobenzyl chloride, to obtain 230 mg of a solid product.

$^1$H-NMR (300 MHz, CDCl$_3$-d): δ 1.74-1.75 (m, 2H); 1.85 (d, 2H); 2.07 (t, 2H); 2.26 (s, 3H); 2.54 (m, 1H); 3.00-3.03

(d, 2H); 3.67 (s, 2H); 3.74 (s, 2H); 6.99 (m, 1H); 7.19-7.21 (m, 2H); 7.34 (s, 1H). MS (TOF) 388.3 (M+).

EXAMPLE 20

N-methyl-N-(2,4-dichlorobenzyl)-N-{[1-(2-chloro-thiazol-5-yl)methyl]piperidin-4-yl}amine (Mol-Hsp70-303)

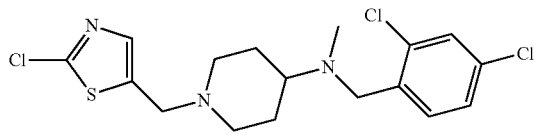 [SMILES: CN(Cc1ccc(Cl)cc1Cl)C1CCN(Cc2cnc(Cl)s2)CC1]

The method of Example 14 was carried out, except for the use of 2,4-dichlorobenzyl chloride in place of 2-cyanobenzyl chloride, to obtain 240 mg of a solid product.

$^1$H-NMR (300 MHz, CDCl$_3$-d): δ 1.45 (m, 2H); 1.68-1.69 (m, 2H); 2.02-2.08 (t, 2H); 2.25 (s, 3H); 2.47 (m, 1H); 2.98-3.01 (d, 2H); 3.65 (s, 4H); 7.22-7.25 (m, 1H); 7.35-7.37 (m, 2H); 7.45 (s, 1H). MS (TOF) 404.8 (M+).

EXAMPLE 21

N-methyl-N-(2-methylbenzyl)-N-{[1-(2-chlorothi-azol-5-yl)methyl]piperidin-4-yl}amine (Mol-Hsp70-305)

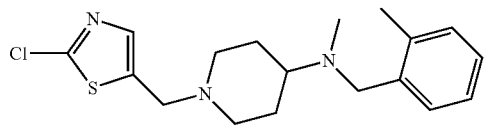 [SMILES: Cc1ccccc1CN(C)C1CCN(Cc2cnc(Cl)s2)CC1]

The method of Example 14 was carried out, except for the use of o-methylbenzyl chloride in place of 2-cyanobenzyl chloride, to obtain 250 mg of a solid product.

$^1$H-NMR (300 MHz, CDCl$_3$-d): δ 1.71-1.72 (m, 2H); 1.83 (d, 2H); 2.05-2.06 (t, 2H); 2.20 (s, 3H); 2.37 (s, 3H); 2.48 (m, 1H); 2.98-3.01 (d, 2H); 3.58 (s, 2H); 3.66 (s, 2H); 7.16-7.17 (m, 3H); 7.29 (m, 1H); 7.35 (s, 1H). MS (TOF) 349.9 (M+).

EXAMPLE 22

N-methyl-N-(4-methylbenzyl)-N-{[1-(2-chlorothi-azol-5-yl)methyl]piperidin-4-yl}amine (Mol-Hsp70-306)

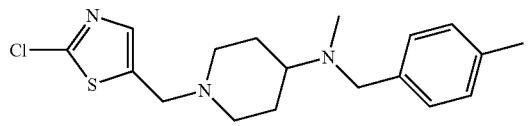 [SMILES: Cc1ccc(CN(C)C2CCN(Cc3cnc(Cl)s3)CC2)cc1]

The method of Example 14 was carried out, except for the use of p-methylbenzyl chloride in place of 2-cyanobenzyl chloride, to obtain 232 mg of a solid product.

$^1$H-NMR (300 MHz, CDCl$_3$-d): δ 1.67 (m, 2H); 1.82 (d, 2H); 2.04 (t, 2H); 2.22 (s, 3H); 2.35 (s, 3H); 2.47 (m, 1H); 2.97-3.00 (d, 2H); 3.57 (s, 2H); 3.64 (s, 2H); 7.13-7.15 (d, 2H); 7.21-7.23 (d, 2H); 7.34 (s, 1H). MS (TOF) 349.9 (M+).

EXAMPLE 23

N-methyl-N-(3-fluorobenzyl)-N-{[1-(2-chlorothi-azol-5-yl)methyl]piperidin-4-yl}amine (Mol-Hsp70-307)

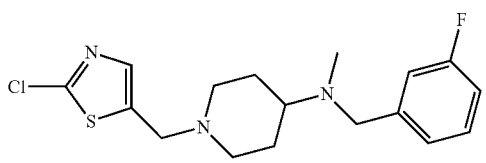 [SMILES: CN(Cc1cccc(F)c1)C1CCN(Cc2cnc(Cl)s2)CC1]

The method of Example 14 was carried out, except for the use of m-fluorobenzyl chloride in place of 2-cyanobenzyl chloride, to obtain 240 mg of a solid product.

$^1$H-NMR (300 MHz, CDCl$_3$-d): δ 1.63-1.67 (m, 2H); 1.80-1.83 (d, 2H); 2.01-2.07 (t, 2H); 2.22 (s, 3H); 2.46 (m, 1H); 2.97-3.00 (d, 2H); 3.59 (s, 2H); 3.65 (s, 2H); 6.94 (m, 1H); 7.07-7.10 (m, 2H); 7.24-7.28 (m, 1H); 7.34 (s, 1H). MS (TOF) 353.9 (M+).

EXAMPLE 24

N-methyl-N-(2,6-dichlorobenzyl)-N-{[1-(2-chloro-thiazol-5-yl)methyl]piperidin-4-yl}amine (Mol-Hsp70-302)

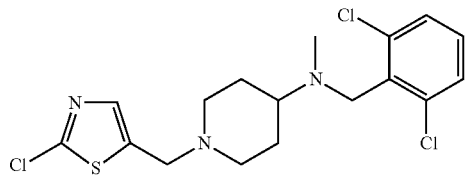 [SMILES: CN(Cc1c(Cl)cccc1Cl)C1CCN(Cc2cnc(Cl)s2)CC1]

The method of Example 14 was carried out, except for the use of 2,6-dichlorobenzyl chloride in place of 2-cyanoben-zyl chloride, to obtain 240 mg of a solid product.

$^1$H-NMR (300 MHz, CDCl$_3$-d): δ 1.76-1.84 (m, 2H); 2.08 (m, 2H); 2.26 (m, 2H); 2.56 (s, 3H); 3.01-3.04 (m, 1H); 3.67 (m, 2H); 3.86 (s, 2H); 7.15-1.17 (s, 1H); 7.28-7.30 (t, 1H); 7.32-7.36 (m, 3H). MS (TOF) 404.8 (M+).

EXAMPLE 25

N-methyl-N-(2-methylbenzyl)-N-{[1-(2-methylthio-thiazol-5-yl)methyl]piperidin-4-yl}amine (Mol-Hsp70-310)

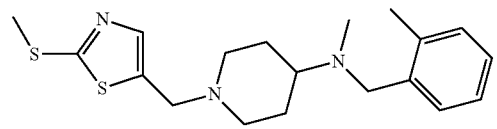 [SMILES: CSc1ncc(CN2CCC(N(C)Cc3ccccc3C)CC2)s1]

20 g of the compound (A) was added to a 250 ml three-necked flask, and dissolved with 100 ml of anhydrous ethanol. Thereafter, 12.7 g of sodium thiomethoxide was added and the reaction mixture was heated to reflux, followed by reacting for 8 h, till the reaction was complete as monitored by TLC. The reaction mixture was cooled to room temperature, and subjected to distillation under reduced pressure in water bath of 50° C. The resulting residue was dissolved with water and extracted with ethyl acetate. The ethyl acetate phase was dried over anhydrous MgSO$_4$ and filtered. The filter residue was washed with a small amount of ethyl acetate, and then the combined filtrate and washings was subjected to distillation under reduced pressure in water bath of 45° C., to obtain 18 g of a colorless oily compound tert-butyl N-methyl-N-{1-[(2-methylthiothiazol-5-yl)methyl]piperidin-4-yl}carbamate, yield 87.4%.

10 g of the resulting compound was added to a 100 ml single neck round-bottom flask, and dissolved with 50 ml of DCM. Thereafter, an excess of trifluoroacetic acid was added under ice bath, followed by stirring at room temperature, till the raw material disappeared as monitored by TLC (take a small amount of the reaction mixture, add water, make it basic with K$_2$CO$_3$, and analyze the DCM phase with thin-layer chromatography), and then the reaction was stopped. The reaction mixture was made basic with saturated aqueous K$_2$CO$_3$ solution, and extracted three times with 50 ml of water. The organic phase was collected, and subjected to distillation under reduced pressure to obtain 6.2 g of a yellow oily compound N-methyl-N-{1-[(2-methylthiothiazol-5-yl)methyl]piperidin-4-yl}amine, yield 62.00%.

0.3 g of the resulting compound was added to a 25 ml single neck round-bottom flask, and dissolved with 5 ml of DMF. Thereafter, 0.3 g of anhydrous K$_2$CO$_3$ was added with stirring, and finally 0.2 g of o-methylbenzyl chloride was added, followed by reacting at room temperature for 4 h, till the reaction was complete as monitored by TLC, and then water was added to stop the reaction. The reaction mixture was extracted with DCM, and the DCM phase was separated with thin-layer chromatography. The product band silica gel was scraped off, soaked with anhydrous DCM, and filtered. The filter residue was washed with a small amount of DCM, and the combined filtrate and washings was subjected to distillation under reduced pressure in water bath of 30° C. to obtain 161 mg of a colorless oily product.

$^1$H-NMR (300 MHz, CDCl$_3$-d): δ 1.71-1.72 (m, 2H); 1.82 (d, 2H); 2.03-2.04 (t, 2H); 2.20 (s, 3H); 2.37 (s, 3H); 2.47 (m, 1H); 2.70 (s, 3H); 2.98-3.01 (d, 2H); 3.57 (s, 2H); 3.67 (s, 2H); 7.16-7.17 (m, 3H); 7.29 (m, 1H); 7.42 (s, 1H). MS (TOF) 361.6 (M+).

EXAMPLE 26

N-methyl-N-(4-methylbenzyl)-N-{[1-(2-methylthiothiazol-5-yl)methyl]piperidin-4-yl}amine (Mol-Hsp70-311)

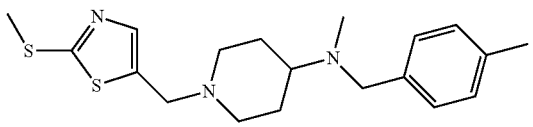

The method of Example 25 was carried out, except for the use of p-methylbenzyl chloride in place of o-methylbenzyl chloride, to obtain 150 mg of a solid product.

$^1$H-NMR (300 MHz, CDCl$_3$-d): δ 1.67-1.68 (m, 2H); 1.80 (d, 2H); 1.99-2.01 (t, 2H); 2.21 (s, 3H); 2.35 (s, 3H); 2.45 (m, 1H); 2.69 (s, 3H); 2.97-2.99 (d, 2H); 3.56 (s, 2H); 3.66 (s, 2H); 7.12-7.14 (d, 2H); 7.20-7.28 (d, 2H); 7.41 (s, 1H). MS (TOF) 361.6 (M+).

EXAMPLE 27

N-methyl-N-(3-fluorobenzyl)-N-{[1-(2-methylthiothiazol-5-yl)methyl]piperidin-4-yl}amine (Mol-Hsp70-312)

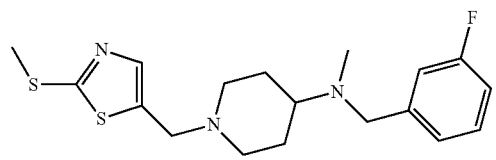 [SMILES: CSc1ncc(CN2CCC(N(C)Cc3cccc(F)c3)CC2)s1]

The method of Example 25 was carried out, except for the use of m-fluorobenzyl chloride in place of o-methylbenzyl chloride, to obtain 132 mg of a solid product.

$^1$H-NMR (300 MHz, CDCl$_3$-d): δ 1.63-1.67 (m, 2H); 1.79-1.82 (d, 2H); 1.99-2.05 (t, 2H); 2.22 (s, 3H); 2.45 (m, 1H); 2.69 (s, 3H); 2.97-3.00 (d, 2H); 3.58 (s, 2H); 3.67 (s, 2H); 6.93-6.94 (t, 2H); 7.06-7.10 (m, 2H); 7.26-7.28 (m, 1H); 7.42 (s, 1H). MS (TOF) 365.5 (M+).

EXAMPLE 28

N-methyl-N-(3-chlorobenzyl)-N-{1-[(2-methylthiothiazol-5-yl)methyl]piperidin-4-yl}amine (Mol-Hsp70-220)

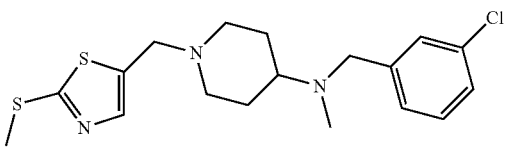 [SMILES: CSc1ncc(CN2CCC(N(C)Cc3cccc(Cl)c3)CC2)s1]

The method of Example 25 was carried out, except for the use of m-chlorobenzyl chloride in place of o-methylbenzyl chloride, to obtain 138 mg of a solid product.

$^1$H-NMR (300 MHz, CDCl$_3$-d): δ 1.63-1.70 (m, 2H); 1.79-1.82 (d, 2H); 1.99-2.05 (t, 2H); 2.22 (s, 3H); 2.44 (m, 1H); 2.69 (s, 3H); 2.97-3.00 (d, 2H); 3.56 (s, 2H); 3.66 (s, 2H); 7.21-7.24 (m, 3H); 7.34 (s, 1H); 7.42 (s, 1H); 7.42 (s, 1H). MS (TOF) 382 (M+).

EXAMPLE 29

N-methyl-N-(4-fluorobenzyl)-N-{1-[(2-methylthiothiazol-5-yl)methyl]piperidin-4-yl}amine (Mol-Hsp70-227)

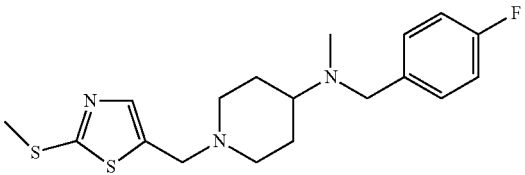 [SMILES: CSc1ncc(CN2CCC(N(C)Cc3ccc(F)cc3)CC2)s1]

The method of Example 25 was carried out, except for the use of p-fluorobenzyl chloride in place of o-methylbenzyl chloride, to obtain 145 mg of a solid product.

¹H-NMR (300 MHz, CDCl₃-d): δ 1.63-1.67 (m, 2H); 1.79-1.82 (d, 2H); 1.99-2.05 (t, 2H); 2.20 (s, 3H); 2.44 (m, 1H); 2.69 (s, 3H); 2.97-3.00 (d, 2H); 3.55 (s, 2H); 3.66 (s, 2H); 6.99-7.02 (t, 2H); 7.26-7.30 (t, 2H); 7.41 (s, 1H). MS (TOF) 365.5 (M+).

EXAMPLE 30

N-methyl-N-(3,4-dichlorobenzyl)-N-{1-[(2-methyl-thiothiazol-5-yl)methyl]piperidin-4-yl}amine (Mol-Hsp70-241)

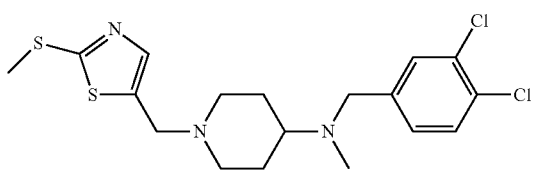 [SMILES: CSc1ncc(CN2CCC(N(C)Cc3ccc(Cl)c(Cl)c3)CC2)s1]

The method of Example 25 was carried out, except for the use of 3,4-dichlorobenzyl chloride in place of o-methylbenzyl chloride, to obtain 160 mg of a solid product.

¹H-NMR (300 MHz, CDCl₃-d): δ 1.62-1.66 (m, 2H); 1.79 (d, 2H); 2.00 (t, 2H); 2.20 (s, 3H); 2.37-2.46 (m, 1H); 2.69 (s, 3H); 2.97-3.00 (d, 2H); 3.37 (s, 2H); 3.84 (s, 2H); 7.02-7.17 (d, 1H); 7.37-7.72 (m, 3H). MS (TOF) 416.4 (M+).

EXAMPLE 31

N-methyl-N-(2-fluoro-6-chlorobenzyl)-N-{1-[(2-methylthiothiazol-5-yl)methyl]piperidin-4-yl}amine (Mol-Hsp70-228)

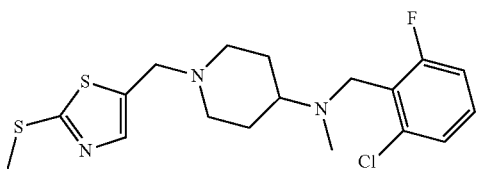 [SMILES: CSc1ncc(CN2CCC(N(C)Cc3c(F)cccc3Cl)CC2)s1]

The method of Example 25 was carried out, except for the use of 2-fluoro-6-chlorobenzyl chloride in place of o-methylbenzyl chloride, to obtain 160 mg of a solid product.

¹H-NMR (300 MHz, CDCl₃-d): δ 1.71-1.75 (m, 2H); 1.84-1.87 (m, 2H); 2.02-2.05 (m, 2H); 2.26 (s, 3H); 2.52 (m, 1H); 2.69 (s, 3H); 3.00-3.03 (d, 2H); 3.68 (s, 2H); 3.72 (s, 2H); 6.98-6.99 (m, 1H); 7.17-7.20 (m, 2H); 7.42 (s, 1H). MS (TOF) 416.4 (M+).

EXAMPLE 32

N-methyl-N-(2,6-dichlorobenzyl)-N-{1-[(2-methyl-thiothiazol-5-yl)methyl]piperidin-4-yl}amine (Mol-Hsp70-231)

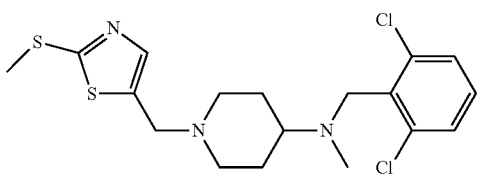 [SMILES: CSc1ncc(CN2CCC(N(C)Cc3c(Cl)cccc3Cl)CC2)s1]

The method of Example 25 was carried out, except for the use of 2,6-dichlorobenzyl chloride in place of o-methylbenzyl chloride, to obtain 155 mg of a solid product.

¹H-NMR (300 MHz, CDCl₃-d): δ 1.72-1.76 (m, 2H); 1.83-1.86 (m, 2H); 2.02-2.08 (m, 2H); 2.25 (s, 3H); 2.55 (m, 1H); 2.69 (s, 3H); 3.00-3.03 (d, 2H); 3.68 (s, 2H); 3.85 (s, 2H); 7.12-7.14 (m, 1H); 7.28-7.30 (m, 2H); 7.42 (s, 1H). MS (TOF) 416.4 (M+).

EXAMPLE 33

N-methyl-N-(2,4-dichlorobenzyl)-N-{1-[(2-methyl-thiothiazol-5-yl)methyl]piperidin-4-yl}amine (Mol-Hsp70-308)

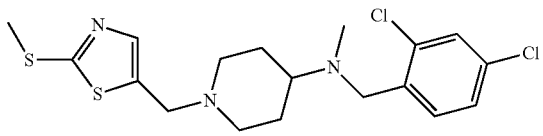 [SMILES: CSc1ncc(CN2CCC(N(C)Cc3ccc(Cl)cc3Cl)CC2)s1]

The method of Example 25 was carried out, except for the use of 2,4-dichlorobenzyl chloride in place of o-methylbenzyl chloride, to obtain 155 mg of a solid product.

¹H-NMR (300 MHz, CDCl₃-d): δ 1.42-1.44 (m, 3H); 1.66-1.69 (m, 2H); 1.81 (m, 2H); 2.02 (m, 2H); 2.26 (s, 3H); 2.48 (m, 1H); 3.00-3.03 (d, 2H); 3.58 (s, 1H); 3.65 (s, 1H); 4.41-4.46 (m, 2H); 6.91 (s, 1H); 7.16-7.17 (m, 1H); 7.25-7.27 (m, 1H); 7.54 (s, 1H). MS (TOF) 416.4 (M+).

EXAMPLE 34

N-methyl-N-(2,5-dichlorobenzyl)-N-{1-[(2-methyl-thiothiazol-5-yl)methyl]piperidin-4-yl}amine (Mol-Hsp70-309)

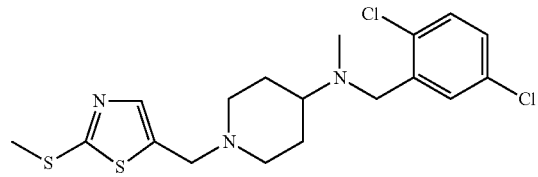 [SMILES: CSc1ncc(CN2CCC(N(C)Cc3cc(Cl)ccc3Cl)CC2)s1]

The method of Example 25 was carried out, except for the use of 2,5-dichlorobenzyl chloride in place of o-methylbenzyl chloride, to obtain 155 mg of a solid product.

¹H-NMR (300 MHz, CDCl₃-d): δ 1.68-1.69 (m, 2H); 1.81 (m, 2H); 2.04 (m, 2H); 2.26 (s, 3H); 2.47 (m, 1H); 2.69 (s, 1H); 2.98-3.01 (m, 2H); 3.65-3.68 (m, 4H); 7.14-7.17 (m, 1H); 7.27-7.28 (m, 1H); 7.42 (s, 1H); 7.54 (s, 1H). MS (TOF) 416.4 (M+).

EXAMPLE 35

N-methyl-N-(4-fluorobenzyl)-N-[1-(2-methylthiopyrimidin-4-yl)piperidin-4-yl]amine (Mol-Hsp70-93)

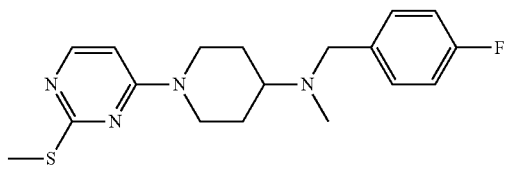

60 g of 2,4-dichloropyrimidine was added to a 1000 ml three-necked flask, and dissolved with 300 ml of DMF. Thereafter, 49.3 g (1.2 mol) of anhydrous K₂CO₃ was added, and 76.5 g (1.2 mol) of tert-butyl N-methyl-N-(piperidin-4-yl)carbamate was added under stirring, followed by stirring at room temperature for 6 h, till the reaction was complete as monitored by TLC. Under stirring, a large amount of ice water was added to the reaction mixture, the precipitated solid was filtered, the filter cake was washed with a large amount of petroleum ether, and then the filter cake was dried to obtain a white powder, which is a mixture of tert-butyl N-methyl-N-{1-[(2-chloropyrimidin-4-yl)methyl]piperidin-4-yl}carbamate and tert-butyl N-methyl-N-{1-[(4-chloropyrimidin-2-yl)methyl]piperidin-4-yl}carbamate. After separation through chromatographic column, 95.7 g of tert-butyl N-methyl-N-{1-[(2-chloropyrimidin-4-yl)methyl]piperidin-4-yl}carbamate was obtained.

20 g of the resulting compound was added to a 250 ml three-necked flask, and dissolved with 100 ml of anhydrous THF. Thereafter, 12.7 g of sodium thiomethoxide was added and the reaction mixture was heated to reflux, followed by reacting for 8 h, till the reaction was complete as monitored by TLC. The reaction mixture was cooled to room temperature, and subjected to distillation under reduced pressure in water bath of 50° C. The resulting residue was dissolved with water and extracted with ethyl acetate. The ethyl acetate phase was dried over anhydrous MgSO₄ and filtered. The filter residue was washed with a small amount of ethyl acetate, and then the combined filtrate and washings was subjected to distillation under reduced pressure in water bath of 45° C., to obtain 18 g of a colorless oily compound tert-butyl N-methyl-N-{1-[(2-methylthiopyrimidin-4-yl)methyl]piperidin-4-yl}carbamate.

10 g of the resulting compound was added to a 100 ml single neck round-bottom flask, and dissolved with 50 ml of DCM. Thereafter, an excess of trifluoroacetic acid was added under ice bath, followed by stirring at room temperature, till the raw material disappeared as monitored by TLC (take a small amount of the reaction mixture, add water, make it basic with K₂CO₃, and analyze the DCM phase with thin-layer chromatography), and then the reaction was stopped. The reaction mixture was made basic with saturated aqueous K₂CO₃ solution, and extracted three times with 50 ml of water. The organic phase was collected, and subjected to distillation under reduced pressure to obtain 5.7 g of a yellow oily compound N-methyl-N-{1-[(2-methylthiopyrimidin-4-yl)methyl]piperidin-4-yl}amine.

0.3 g of the resulting compound was added to a 25 ml single neck round-bottom flask, and dissolved with 5 ml of DMF. Thereafter, 0.3 g of anhydrous K₂CO₃ was added with stirring, and finally 0.2 g of p-fluorobenzyl chloride was added, followed by reacting at room temperature for 4 h, till the reaction was complete as monitored by TLC, and then water was added to stop the reaction. The reaction mixture was extracted with DCM, and the DCM phase was separated with thin-layer chromatography. The product band silica gel was scraped off, soaked with anhydrous DCM, and filtered. The filter residue was washed with a small amount of DCM, and the combined filtrate and washings was subjected to distillation under reduced pressure in water bath of 30° C. to obtain 171 mg of a colorless oily product.

¹H-NMR (300 MHz, CDCl₃-d): δ 1.56-1.60 (m, 2H); 1.90-1.93 (d, 2H); 2.20 (s, 3H); 2.53 (s, 3H); 2.73 (m, 1H); 2.85-2.92 (m, 2H); 3.57 (s, 2H); 4.47-4.49 (d, 2H); 6.21-6.23 (d, 1H); 6.99-7.03 (t, 2H); 7.28-7.31 (m, 2H); 8.01-8.03 (d, 1H). MS (TOF) 346.5 (M+).

EXAMPLE 36

N-methyl-N-(4-cyanobenzyl)-N-[1-(2-methylthiopyrimidin-4-yl)piperidin-4-yl]amine (Mol-Hsp70-144)

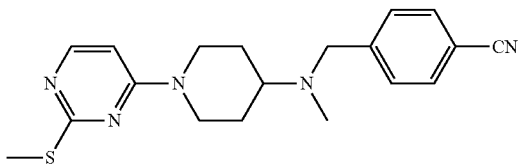

The method of Example 35 was carried out, except for the use of p-cyanobenzyl chloride in place of p-fluorobenzyl chloride, to obtain 160 mg of a solid product.

¹H-NMR (300 MHz, CDCl₃-d): δ 1.55-1.59 (m, 2H); 1.91-1.94 (d, 2H); 2.21 (s, 3H); 2.50 (s, 3H); 2.75 (m, 1H); 2.84-2.90 (t, 2H); 3.65 (s, 2H); 4.48 (d, 2H); 6.21-6.22 (d, 1H); 7.46-7.48 (d, 3H); 7.61-7.63 (d, 2H); 8.01-8.02 (d, 1H). MS (TOF) 353.5 (M+).

EXAMPLE 37

N-methyl-N-(2-fluoro-6-chlorobenzyl)-N-[1-(2-methylthiopyrimidin-4-yl)piperidin-4-yl]amine (Mol-Hsp70-125)

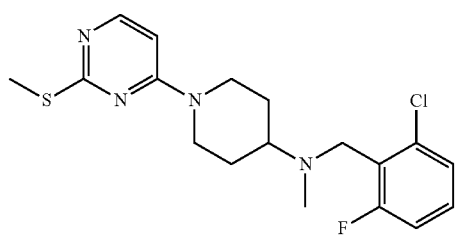 [SMILES: CSc1nccc(N2CCC(N(C)Cc3c(F)cccc3Cl)CC2)n1]

The method of Example 35 was carried out, except for the use of 2-fluoro-6-chlorobenzyl chloride in place of p-fluorobenzyl chloride, to obtain 160 mg of a solid product.

¹H-NMR (300 MHz, CDCl₃-d): δ 1.62-1.69 (m, 2H); 1.97-2.00 (d, 2H); 2.28 (s, 3H); 2.50 (s, 3H); 2.85-2.92 (t, 3H); 3.71 (s, 2H); 4.5 (s, 2H); 6.21-6.23 (d, 1H); 6.99-7.05 (m, 1H); 7.20-7.22 (m, 2H); 8.00-8.02 (d, 1H). MS (TOF) 380.9 (M+).

EXAMPLE 38

N-methyl-N-(3,4-dichlorobenzyl)-N-[1-(2-methylthiopyrimidin-4-yl)piperidin-4-yl]amine (Mol-Hsp70-138)

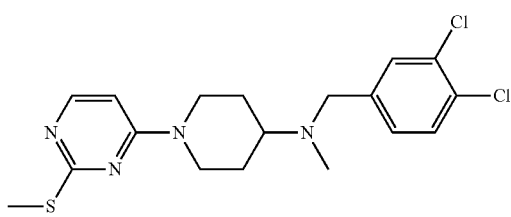

The method of Example 35 was carried out, except for the use of 3,4-dichlorobenzyl chloride in place of p-fluorobenzyl chloride, to obtain 160 mg of a solid product.

¹H-NMR (300 MHz, CDCl₃-d): δ 1.55-1.57 (m, 2H); 1.90-1.93 (d, 2H); 2.20 (s, 3H); 2.50 (s, 3H); 2.74-2.90 (m, 3H); 3.55 (s, 2H); 4.48 (s, 2H); 6.20-6.22 (d, 1H); 7.19 (s, 1H); 7.37-7.45 (m, 2H); 8.00-8.02 (d, 1H). MS (TOF) 397.4 (M+).

EXAMPLE 39

N-methyl-N-(3-chlorobenzyl)-N-[1-(2-methylthiopyrimidin-4-yl)piperidin-4-yl]amine (Mol-Hsp70-94)

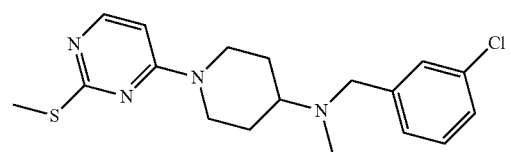 [SMILES: CSc1nccc(N2CCC(N(C)Cc3cccc(Cl)c3)CC2)n1]

The method of Example 35 was carried out, except for the use of m-chlorobenzyl chloride in place of p-fluorobenzyl chloride, to obtain 150 mg of a solid product.

¹H-NMR (300 MHz, CDCl₃-d): δ 1.57-1.60 (m, 2H); 1.90-1.93 (d, 2H); 2.22 (s, 3H); 2.52 (s, 3H); 2.74 (m, 1H); 2.89-2.90 (m, 2H); 3.58 (s, 2H); 4.47-4.49 (d, 2H); 6.21-6.23 (d, 1H); 7.24-7.28 (m, 3H); 7.36 (s, 1H); 8.02-8.03 (d, 1H). MS (TOF) 362.9 (M+).

EXAMPLE 40

N-methyl-N-(2,4-dichlorobenzyl)-N-[1-(2-methylthiopyrimidin-4-yl)piperidin-4-yl]amine (Mol-Hsp70-145)

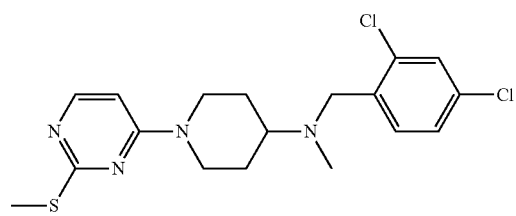 [SMILES: CSc1nccc(N2CCC(N(C)Cc3ccc(Cl)cc3Cl)CC2)n1]

The method of Example 35 was carried out, except for the use of 2,4-dichlorobenzyl chloride in place of p-fluorobenzyl chloride, to obtain 140 mg of a solid product.

¹H-NMR (300 MHz, CDCl₃-d): δ 1.64-1.68 (m, 2H); 1.96 (d, 2H); 2.27 (s, 3H); 2.53 (s, 3H); 2.86-2.89 (t, 3H); 3.89 (s, 2H); 4.54 (m, 2H); 6.23-6.24 (d, 1H); 7.17-7.19 (t, 1H); 7.32-7.34 (d, 2H); 8.02-8.04 (d, 1H). MS (TOF) 397.4 (M+).

EXAMPLE 41

N-methyl-N-(2-cyanobenzyl)-N-[1-(2-methylthiopyrimidin-4-yl)piperidin-4-yl]amine (Mol-Hsp70-146)

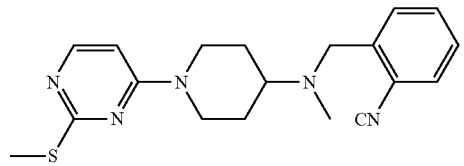

The method of Example 35 was carried out, except for the use of o-cyanobenzyl chloride in place of p-fluorobenzyl chloride, to obtain 160 mg of a solid product.

¹H-NMR (300 MHz, CDCl₃-d): δ 1.59-1.65 (m, 2H); 1.96-1.99 (d, 2H); 2.21 (s, 3H); 2.51 (s, 3H); 2.82-2.93 (t, 3H); 3.80 (s, 2H); 4.50-4.52 (m, 2H); 6.22-6.23 (d, 1H); 7.35-7.38 (m, 1H); 7.56-7.57 (m, 2H); 7.64-7.66 (d, 1H); 8.01-8.02 (d, 1H). MS (TOF) 353.5 (M+).

EXAMPLE 42

N-methyl-N-(4-methylbenzyl)-N-[1-(2-methylthiopyrimidin-4-yl)piperidin-4-yl]amine (Mol-Hsp70-147)

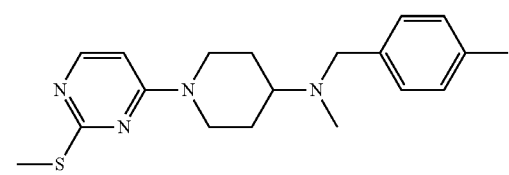

The method of Example 35 was carried out, except for the use of p-methylbenzyl chloride in place of p-fluorobenzyl chloride, to obtain 145 mg of a solid product.

¹H-NMR (300 MHz, CDCl₃-d): δ 1.58-1.62 (m, 2H); 1.92-1.95 (d, 2H); 2.23 (s, 3H); 2.36 (s, 3H); 2.52 (s, 3H); 2.76 (m, 1H); 2.85-2.92 (t, 2H); 3.59 (s, 2H); 4.47 (m, 2H); 6.21-6.23 (d, 1H); 7.14-7.16 (d, 2H); 7.22-7.24 (d, 2H); 8.02-8.03 (d, 1H). MS (TOF) 342.5 (M+).

EXAMPLE 43

N-methyl-N-(2-chlorobenzyl)-N-[1-(2-methoxypyrimidin-4-yl)piperidin-4-yl]amine (Mol-Hsp70-148)

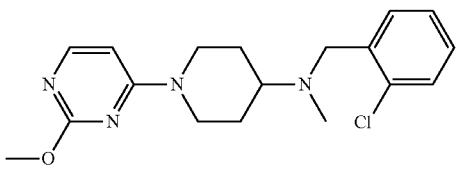

60 g of 2,4-dichloropyrimidine was added to a 1000 ml three-necked flask, and dissolved with 300 ml of DMF. Thereafter, 49.3 g of anhydrous K₂CO₃ was added, and 76.5 g of tert-butyl N-methyl-N-(piperidin-4-yl)carbamate was added under stirring, followed by stirring at room temperature for 6 h, till the reaction was complete as monitored by TLC. Under stirring, a large amount of ice water was added to the reaction mixture, the precipitated solid was filtered, the filter cake was washed with a large amount of petroleum ether, and then the filter cake was dried to obtain 90 g of a white powder, which is a mixture of tert-butyl N-methyl-N-{1-[(2-chloropyrimidin-4-yl)methyl]piperidin-4-yl}carbamate and tert-butyl N-methyl-N-{1-[(4-chloropyrimidin-2-yl)methyl]piperidin-4-yl}carbamate. After separation through chromatographic column, tert-butyl N-methyl-N-{1-[(2-chloropyrimidin-4-yl)methyl]piperidin-4-yl}carbamate was obtained.

20 g of the resulting compound was added to a 250 ml three-necked flask, and dissolved with 100 ml of anhydrous ethanol. Thereafter, 12.7 g of sodium methoxide was added and the reaction mixture was heated to reflux, followed by reacting for 8 h, till the reaction was complete as monitored by TLC. The reaction mixture was cooled to room temperature, and subjected to distillation under reduced pressure in water bath of 50° C. The resulting residue was dissolved with water and extracted with ethyl acetate. The ethyl acetate phase was dried over anhydrous MgSO₄ and filtered. The filter residue was washed with a small amount of ethyl acetate, and then the combined filtrate and washings was subjected to distillation under reduced pressure in water bath of 45° C., to obtain 18 g of a colorless oily compound tert-butyl N-methyl-N-{1-[(2-methoxypyrimidin-4-yl)methyl]piperidin-4-yl}carbamate.

10 g of the resulting compound was added to a 100 ml single neck round-bottom flask, and dissolved with 50 ml of DCM. Thereafter, an excess of trifluoroacetic acid was added under ice bath, followed by stirring at room temperature, till the raw material disappeared as monitored by TLC (take a small amount of the reaction mixture, add water, make it basic with K₂CO₃, and analyze the DCM phase with thin-layer chromatography), and then the reaction was stopped. The reaction mixture was made basic with saturated aqueous K₂CO₃ solution, and extracted three times with 50 ml of water. The organic phase was collected, and subjected to distillation under reduced pressure to obtain 6.2 g of a yellow oily compound N-methyl-N-{1-[(2-methoxypyrimidin-4-yl)methyl]piperidin-4-yl}amine.

0.3 g of the resulting compound was added to a 25 ml single neck round-bottom flask, and dissolved with 5 ml of DMF. Thereafter, 0.3 g of anhydrous K₂CO₃ was added with stirring, and finally 0.2 g of o-chlorobenzyl chloride was added, followed by reacting at room temperature for 4 h, till the reaction was complete as monitored by TLC, and then water was added to stop the reaction. The reaction mixture was extracted with DCM, and the DCM phase was separated with thin-layer chromatography. The product band silica gel was scraped off, soaked with anhydrous DCM, and filtered. The filter residue was washed with a small amount of DCM, and the combined filtrate and washings was subjected to distillation under reduced pressure in water bath of 30° C. to obtain 154 mg of a solid product.

¹H-NMR (300 MHz, CDCl₃-d): δ 1.57-1.67 (m, 2H); 1.94-1.97 (d, 2H); 2.27 (s, 3H); 2.76-2.79 (m, 1H); 2.88-2.94 (t, 2H); 3.72 (s, 2H); 3.95 (s, 3H); 4.48-4.50 (m, 2H); 6.21-6.22 (d, 1H); 7.18-7.26 (m, 2H); 7.35-7.37 (dd, 1H); 7.49-7.51 (d, 1H); 8.02-8.04 (d, 1H). MS (TOF) 346.9 (M+).

EXAMPLE 44

N-methyl-N-(2,5-dichlorobenzyl)-N-[1-(2-methylthiopyrimidin-4-yl)piperidin-4-yl]amine (Mol-Hsp70-149)

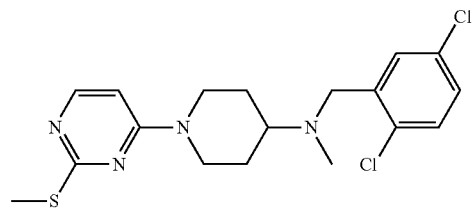 [SMILES: CSc1nccc(N2CCC(N(C)Cc3cc(Cl)ccc3Cl)CC2)n1]

The method of Example 35 was carried out, except for the use of 2,5-dichlorobenzyl chloride in place of p-fluorobenzyl chloride, to obtain 130 mg of a solid product.

¹H-NMR (300 MHz, CDCl₃-d): δ 1.58-1.62 (m, 2H); 1.92-1.95 (d, 2H); 2.25 (s, 3H); 2.52 (s, 3H); 2.86-2.87 (m, 1H); 2.89-2.93 (t, 2H); 3.67 (s, 2H); 4.49-4.51 (m, 2H); 6.22-6.23 (d, 1H); 7.23-7.26 (dd, 1H); 7.38-7.45 (s, 1H); 7.45-7.47 (d, 1H); 8.02-8.04 (d, 1H). MS (TOF) 397.4 (M+).

EXAMPLE 45

N-methyl-N-(3-fluorobenzyl)-N-[1-(2-methylthiopyrimidin-4-yl)piperidin-4-yl]amine (Mol-Hsp70-150)

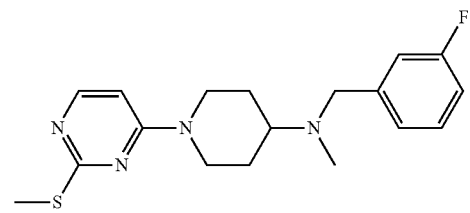 [SMILES: CSc1nccc(N2CCC(N(C)Cc3cccc(F)c3)CC2)n1]

The method of Example 35 was carried out, except for the use of m-fluorobenzyl chloride in place of p-fluorobenzyl chloride, to obtain 144 mg of a solid product.

¹H-NMR (300 MHz, CDCl₃-d): δ 1.57-1.61 (m, 2H); 1.92-1.95 (d, 2H); 2.23 (s, 3H); 2.52 (s, 3H); 2.86-2.87 (m, 1H); 2.89-2.93 (t, 2H); 3.61 (s, 2H); 4.48-4.50 (m, 2H); 6.22-6.23 (d, 1H); 6.95 (t, 1H); 7.09-7.11 (m, 2H); 7.29 (s, 1H); 8.02-8.04 (d, 1H). MS (TOF) 346.5 (M+).

EXAMPLE 46

N-methyl-N-[1-(4-methoxypyrimidin-2-yl)piperidin-4-yl]amine (Mol-Hsp70-002)

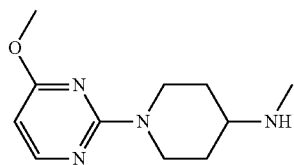 [SMILES: CNC1CCN(c2nccc(OC)n2)CC1]

60 g of 2,4-dichloropyrimidine was added to a 1000 ml three-necked flask, and dissolved with 300 ml of DMF. Thereafter, 49.3 g of anhydrous K₂CO₃ was added, and 76.5 g of tert-butyl N-methyl-N-(piperidin-4-yl)carbamate was added under stirring, followed by stirring at room temperature for 6 h, till the reaction was complete as monitored by TLC. Under stirring, a large amount of ice water was added to the reaction mixture, the precipitated solid was filtered, the filter cake was washed with a large amount of petroleum ether, and then the filter cake was dried to obtain 50 g of a white powder, which is a mixture of tert-butyl N-methyl-N-[1-(4-chloropyrimidin-2-yl)piperidin-4-yl]carbamate and tert-butyl N-methyl-N-[1-(2-chloropyrimidin-4-yl)piperidin-4-yl]carbamate. After separation through chromatographic column, tert-butyl N-methyl-N-[1-(4-chloropyrimidin-2-yl)piperidin-4-yl]carbamate was obtained.

20 g of the resulting compound was added to a 250 ml three-necked flask, and dissolved with 100 ml of anhydrous ethanol. Thereafter, 12.7 g of sodium methoxide was added and the reaction mixture was heated to reflux, followed by reacting for 8 h, till the reaction was complete as monitored by TLC. The reaction mixture was cooled to room temperature, and subjected to distillation under reduced pressure in water bath of 50° C. The resulting residue was dissolved with water and extracted with ethyl acetate. The ethyl acetate phase was dried over anhydrous MgSO₄ and filtered. The filter residue was washed with a small amount of ethyl acetate, and then the combined filtrate and washings was subjected to distillation under reduced pressure in water bath of 45° C., to obtain 18 g of a colorless oily compound tert-butyl N-methyl-N-[1-(4-methoxypyrimidin-2-yl)piperidin-4-yl]carbamate.

10 g of the resulting compound was added to a 100 ml single neck round-bottom flask, and dissolved with 50 ml of DCM. Thereafter, an excess of trifluoroacetic acid was added under ice bath, followed by stirring at room temperature, till the raw material disappeared as monitored by TLC (take a small amount of the reaction mixture, add water, make it basic with K₂CO₃, and analyze the DCM phase with thin-layer chromatography), and then the reaction was stopped. The reaction mixture was made basic with saturated aqueous K₂CO₃ solution, and extracted three times with 50 ml of water. The organic phase was collected, and subjected to distillation under reduced pressure to obtain 5.2 g of a yellow oily compound N-methyl-N-[1-(4-methoxypyrimidin-2-yl)piperidin-4-yl]amine.

¹H-NMR (300 MHz, D₂O-d₂): δ 1.61-1.71 (m, 2H); 2.24-2.27 (d, 2H); 2.70 (s, 2H); 3.20-3.26 (t, 2H); 3.41-3.49 (m, 1H); 4.00 (s, 3H); 4.53 (m, 1H); 6.36-6.38 (d, 1H); 7.87-7.88 (d, 1H). MS (TOF) 258.7 (M+).

EXAMPLE 47

N-methyl-N-(2-chlorobenzyl)-N-[1-(2-methylthiopyrimidin-4-yl)piperidin-4-yl]amine (Mol-Hsp70-151)

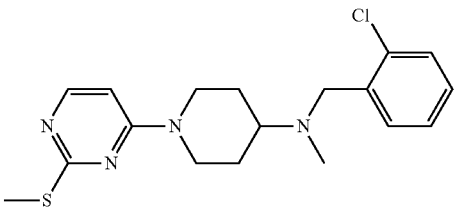

The method of Example 35 was carried out, except for the use of o-chlorobenzyl chloride in place of p-fluorobenzyl chloride, to obtain 181 mg of a coloroless oily product.

¹H-NMR (300 MHz, CDCl₃-d): δ 1.60-1.64 (m, 2H); 1.95-1.98 (d, 2H); 2.27 (s, 3H); 2.52 (s, 3H); 2.87-2.88 (m, 1H); 2.91-2.94 (t, 2H); 3.72 (s, 2H); 4.49-4.50 (m, 2H); 6.21-6.24 (d, 1H); 7.20-7.26 (m, 2H); 7.35-7.37 (d, 1H); 7.49 (d, 1H); 8.02-8.03 (d, 1H). MS (TOF) 362.9 (M+).

EXAMPLE 48

N-methyl-N-(4-cyanobenzyl)-N-[1-(2-methoxypyrimidin-4-yl)piperidin-4-yl]amine (Mol-Hsp70-152)

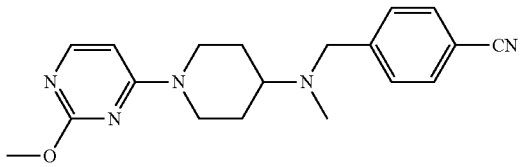 [SMILES: COc1nccc(N2CCC(N(C)Cc3ccc(C#N)cc3)CC2)n1]

The method of Example 43 was carried out, except for the use of p-cyanobenzyl chloride in place of o-chlorobenzyl chloride, to obtain 159 mg of a solid product.

¹H-NMR (300 MHz, CDCl₃-d): δ 1.54-1.58 (m, 2H); 1.89-1.92 (d, 2H); 2.20 (s, 3H); 2.72 (m, 1H); 2.85-2.92 (t, 2H); 3.64 (s, 2H); 3.92 (s, 3H); 4.45-4.48 (m, 2H); 6.19-6.20 (d, 1H); 7.44-7.46 (d, 2H); 7.59-7.61 (d, 2H); 7.49-7.51 (d, 1H); 8.01-8.02 (d, 1H). MS(TOF) 337.4 (M+).

EXAMPLE 49

N-methyl-N-(2,6-dichlorobenzyl)-N-[1-(2-methylthiopyrimidin-4-yl)piperidin-4-yl]amine (Mol-Hsp70-153)

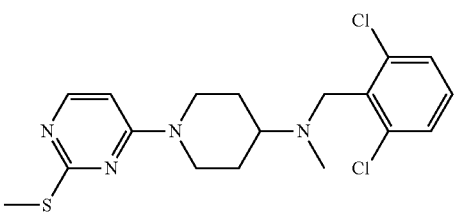

The method of Example 35 was carried out, except for the use of 2,6-dichlorobenzyl chloride in place of p-fluorobenzyl chloride, to obtain 176 mg of a solid product.

¹H-NMR (300 MHz, CDCl₃-d): δ 1.63-1.67 (m, 2H); 1.94-1.97 (d, 2H); 2.24 (s, 3H); 2.86-2.90 (m, 3H); 3.87 (s,

2H); 3.94 (s, 3H); 4.51-4.53 (m, 2H); 6.21-6.22 (d, 1H); 7.13-7.17 (t, 1H); 7.30-7.33 (m, 2H); 8.02-8.03 (d, 1H). MS (TOF) 381.3 (M+).

EXAMPLE 50

N-methyl-N-(2-cyanobenzyl)-N-[1-(2-methoxypyrimidin-4-yl)piperidin-4-yl]amine (Mol-Hsp70-154)

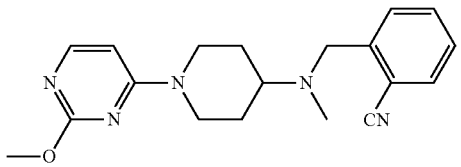 [SMILES: COc1nccc(N2CCC(N(C)Cc3ccccc3C#N)CC2)n1]

The method of Example 43 was carried out, except for the use of o-cyanobenzyl chloride in place of o-chlorobenzyl chloride, to obtain 165 mg of a solid product.

$^1$H-NMR (300 MHz, CDCl$_3$-d): δ 1.60-1.64 (m, 2H); 1.97-2.00 (d, 2H); 2.23 (s, 3H); 2.84-2.94 (m, 3H); 3.82 (s, 2H); 3.95 (s, 3H); 4.49-4.52 (m, 2H); 6.21-6.22 (d, 1H); 7.31-7.39 (m, 1H); 7.57-7.58 (m, 2H); 7.65-7.67 (d, 1H); 8.03-8.04 (d, 1H). MS (TOF) 337.4 (M+).

EXAMPLE 51

N-methyl-N-(4-methylbenzyl)-N-[1-(2-methoxypyrimidin-4-yl)piperidin-4-yl]amine (Mol-Hsp70-155)

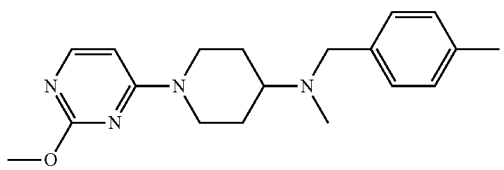

The method of Example 43 was carried out, except for the use of p-methylbenzyl chloride in place of o-chlorobenzyl chloride, to obtain 157 mg of a solid product.

$^1$H-NMR (300 MHz, CDCl$_3$-d): δ 1.57-1.61 (m, 2H); 1.91-1.92 (d, 2H); 2.22 (s, 3H); 2.35 (s, 3H); 2.74 (m, 1H); 2.86-2.92 (t, 2H); 3.58 (s, 2H); 3.94 (s, 3H); 4.45-4.47 (m, 2H); 6.20-6.21 (d, 1H); 7.13-7.15 (dd, 2H); 7.21-7.23 (dd, 2H); 8.02-8.03 (d, 1H). MS (TOF) 326.4 (M+).

EXAMPLE 52

N-methyl-N-(2,5-dichlorobenzyl)-N-[1-(2-methoxypyrimidin-4-yl)piperidin-4-yl]amine (Mol-Hsp70-156)

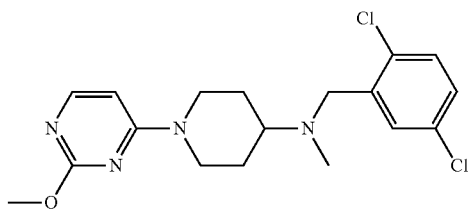 [SMILES: COc1nccc(N2CCC(N(C)Cc3cc(Cl)ccc3Cl)CC2)n1]

The method of Example 43 was carried out, except for the use of 2,5-dichlorobenzyl chloride in place of o-chlorobenzyl chloride, to obtain 143 mg of a solid product.

$^1$H-NMR (300 MHz, CDCl$_3$-d): δ 1.57-1.61 (m, 2H); 1.92-1.95 (d, 2H); 2.24 (s, 3H); 2.76 (m, 1H); 2.86-2.93 (t, 2H); 3.67 (s, 2H); 3.93 (s, 3H); 4.47-4.50 (m, 2H); 6.20-6.21 (d, 1H); 7.22-7.25 (dd, 2H); 7.37 (d, 1H); 7.45-7.47 (d, 1H); 8.02-8.03 (d, 1H). MS (TOF) 381.3 (M+).

EXAMPLE 53

N-methyl-N-(3,4-dichlorobenzyl)-N-[1-(2-methoxypyrimidin-4-yl)piperidin-4-yl]amine (Mol-Hsp70-128)

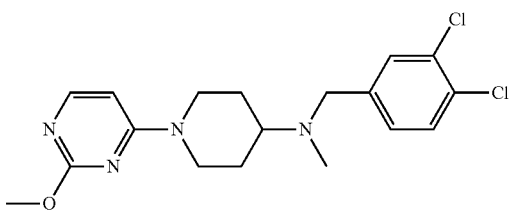

The method of Example 43 was carried out, except for the use of 3,4-dichlorobenzyl chloride in place of o-chlorobenzyl chloride, to obtain 143 mg of a solid product.

$^1$H-NMR (300 MHz, CDCl$_3$-d): δ 1.54-1.60 (m, 2H); 1.92-1.95 (d, 2H); 2.24 (s, 3H); 2.76 (m, 1H); 2.90-2.92 (t, 2H); 3.55 (s, 2H); 3.93 (s, 3H); 4.48 (s, 2H); 6.19-6.21 (d, 1H); 7.17-7.19 (d, 2H); 7.30-7.44 (m, 1H); 8.01-8.03 (d, 1H). MS (TOF) 381.3 (M+).

EXAMPLE 54

N-methyl-N-(2-fluoro-6-chlorobenzyl)-N-[1-(2-methoxypyrimidin-4-yl)piperidin-4-yl]amine (Mol-Hsp70-134)

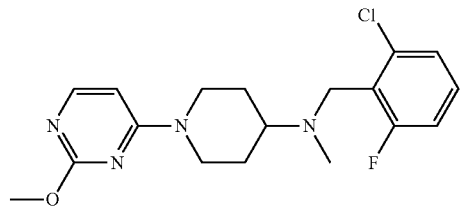

The method of Example 43 was carried out, except for the use of 2-fluoro-6-chlorobenzyl chloride in place of o-chlorobenzyl chloride, to obtain 143 mg of a solid product.

$^1$H-NMR (300 MHz, CDCl$_3$-d): δ 1.63-1.66 (m, 2H); 1.95-1.98 (d, 2H); 2.26 (s, 3H); 2.78 (m, 1H); 2.86-2.92 (t, 2H); 3.74 (s, 2H); 3.93 (s, 3H); 4.51 (s, 2H); 6.20-6.22 (d, 1H); 6.99-7.01 (m, 2H); 7.19-7.21 (m, 1H); 8.01-8.03 (d, 1H). MS (TOF) 364.8 (M+).

EXAMPLE 55

N-methyl-N-(3-chlorobenzyl)-N-[1-(2-methoxypyrimidin-4-yl)piperidin-4-yl]amine (Mol-Hsp70-135)

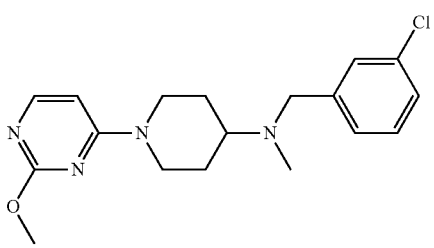 [SMILES: COc1nccc(N2CCC(N(C)Cc3cccc(Cl)c3)CC2)n1]

The method of Example 43 was carried out, except for the use of m-chlorobenzyl chloride in place of o-chlorobenzyl chloride, to obtain 167 mg of a solid product.

$^1$H-NMR (300 MHz, CDCl$_3$-d): δ 1.55-1.62 (m, 2H); 1.91-1.94 (d, 2H); 2.21 (s, 3H); 2.74 (s, 1H); 2.85-2.90 (t, 2H); 3.58 (s, 2H); 3.93 (s, 3H); 4.48 (m, 2H); 6.19-6.21 (d, 1H); 7.23 (m, 2H); 7.34 (s, 2H); 8.00-8.02 (d, 1H). MS (TOF) 346.9 (M+).

EXAMPLE 56

N-methyl-N-(3-fluorobenzyl)-N-[1-(2-methoxypyrimidin-4-yl)piperidin-4-yl]amine (Mol-Hsp70-157)

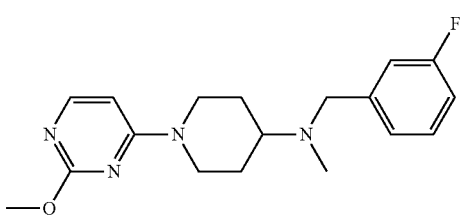

The method of Example 43 was carried out, except for the use of m-fluorobenzyl chloride in place of o-chlorobenzyl chloride, to obtain 167 mg of a solid product.

$^1$H-NMR (300 MHz, CDCl$_3$-d): δ 1.56-1.64 (m, 2H); 1.91-1.94 (d, 2H); 2.22 (s, 3H); 2.74-2.75 (m, 1H); 2.86-2.93 (t, 2H); 3.60 (s, 2H); 3.94 (s, 3H); 4.46-4.49 (m, 2H); 6.20-6.21 (d, 1H); 6.93-6.97 (t, 2H); 7.08-7.11 (m, 2H); 7.25-7.30 (m, 1H); 8.02-8.04 (d, 1H). MS (TOF) 330.4 (M+).

EXAMPLE 57

N-methyl-N-(4-fluorobenzyl)-N-[1-(2-methoxypyrimidin-4-yl)piperidin-4-yl]amine (Mol-Hsp70-127)

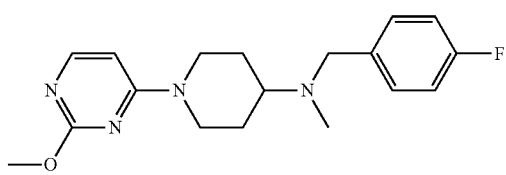 [SMILES: COc1nccc(N2CCC(N(C)Cc3ccc(F)cc3)CC2)n1]

The method of Example 43 was carried out, except for the use of p-fluorobenzyl chloride in place of o-chlorobenzyl chloride, to obtain 167 mg of a solid product.

$^1$H-NMR (300 MHz, CDCl$_3$-d): δ 1.56-1.60 (m, 2H); 1.91-1.94 (d, 2H); 2.20 (s, 3H); 2.74 (s, 1H); 2.84-2.90 (t, 2H); 3.58 (s, 2H); 3.93 (s, 3H); 4.47 (s, 2H); 6.18-6.20 (d, 1H); 6.98-7.02 (t, 2H); 7.30 (m, 2H); 7.25-7.30 (m, 1H); 8.00-8.02 (d, 1H). MS (TOF) 330.4 (M+).

EXAMPLE 58

N-methyl-N-(2-chlorobenzyl)-N-[1-(6-methoxypyrimidin-4-yl)piperidin-4-yl]amine (Mol-Hsp70-248)

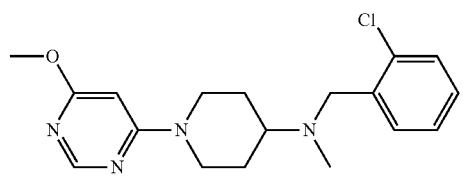 [SMILES: COc1cc(N2CCC(N(C)Cc3ccccc3Cl)CC2)ncn1]

The method of Example 43 was carried out, except for the use of 4,6-dichloropyrimidine in place of 2,4-dichloropyrimidine, to obtain 147 mg of a solid product.

$^1$H-NMR (300 MHz, CDCl$_3$-d): δ 1.60-1.67 (m, 2H); 1.93-1.96 (d, 2H); 2.27 (s, 3H); 2.77 (m, 1H); 2.85-2.92 (t, 2H); 3.72 (s, 2H); 3.93 (s, 3H); 4.40-4.44 (m, 2H); 5.86 (s, 1H); 7.20-7.26 (m, 2H); 7.35-7.37 (dd, 1H); 7.49-7.51 (d, 1H); 8.34 (s, 1H). MS (TOF) 346.9 (M+).

EXAMPLE 59

N-methyl-N-(4-methylbenzyl)-N-[1-(6-methoxypyrimidin-4-yl)piperidin-4-yl]amine (Mol-Hsp70-249)

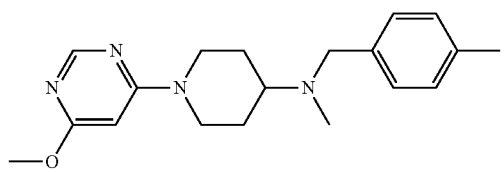

The method of Example 43 was carried out, except for the use of 4,6-dichloropyrimidine in place of 2,4-dichloropyrimidine, and the use of p-methylbenzyl chloride in place of o-chlorobenzyl chloride, to obtain 150 mg of a solid product.

$^1$H-NMR (300 MHz, CDCl$_3$-d): δ 1.58-1.62 (m, 2H); 1.91-1.94 (d, 2H); 2.22 (s, 3H); 2.35 (s, 3H); 2.74 (m, 2H); 2.83-2.90 (t, 2H); 3.58 (s, 2H); 3.93 (s, 3H); 4.38-4.42 (m, 2H); 5.85 (s, 1H); 7.13-7.15 (d, 2H); 7.22-7.24 (d, 2H); 8.34 (s, 1H). MS (TOF) 326.4 (M+).

EXAMPLE 60

N-methyl-N-(2,6-dichlorobenzyl)-N-[1-(6-methoxy-pyrimidin-4-yl)piperidin-4-yl]amine (Mol-Hsp70-250)

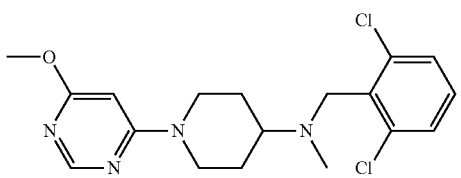 [SMILES: COc1cc(N2CCC(N(C)Cc3c(Cl)cccc3Cl)CC2)ncn1]

The method of Example 43 was carried out, except for the use of 4,6-dichloropyrimidine in place of 2,4-dichloropyrimidine, and the use of 2,6-dichlorobenzyl chloride in place of o-chlorobenzyl chloride, to obtain 153 mg of a solid product.

$^1$H-NMR (300 MHz, CDCl$_3$-d): δ 1.63-1.67 (m, 2H); 1.93-1.96 (d, 2H); 2.24 (s, 3H); 2.83-2.90 (m, 3H); 3.87 (s, 2H); 3.93 (s, 3H); 4.43-4.46 (m, 2H); 5.86 (s, 1H); 7.15-7.17 (t, 1H); 7.29-7.32 (m, 2H); 8.34 (s, 1H). MS (TOF) 381.3 (M+).

EXAMPLE 61

N-methyl-N-(3,4-dichlorobenzyl)-N-[1-(6-methoxy-pyrimidin-4-yl)piperidin-4-yl]amine (Mol-Hsp70-126)

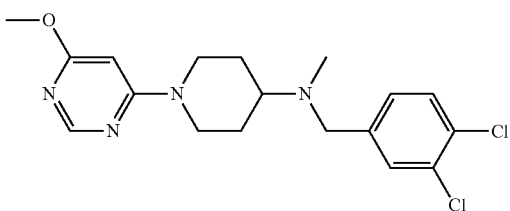 [SMILES: COc1cc(N2CCC(N(C)Cc3ccc(Cl)c(Cl)c3)CC2)ncn1]

The method of Example 43 was carried out, except for the use of 4,6-dichloropyrimidine in place of 2,4-dichloropyrimidine, and the use of 3,4-dichlorobenzyl chloride in place of o-chlorobenzyl chloride, to obtain 153 mg of a solid product.

$^1$H-NMR (300 MHz, CDCl$_3$-d): δ 1.43-1.58 (m, 2H); 1.88-1.90 (m, 2H); 2.19 (s, 3H); 2.72 (m, 1H); 2.82-2.89 (m, 2H); 3.53 (s, 2H); 3.91 (s, 3H); 4.38-4.42 (m, 2H); 5.84 (s, 1H); 7.16 (s, 1H); 7.37-7.44 (m, 2H); 8.32 (s, 1H). MS (TOF) 381.3 (M+).

EXAMPLE 62

N-methyl-N-(4-fluorobenzyl)-N-[1-(6-methoxypy-rimidin-4-yl)piperidin-4-yl]amine (Mol-Hsp70-130)

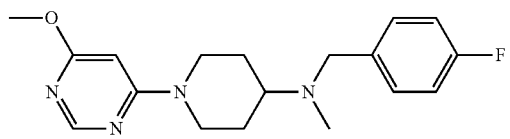

The method of Example 43 was carried out, except for the use of 4,6-dichloropyrimidine in place of 2,4-dichloropyrimidine, and the use of p-fluorobenzyl chloride in place of o-chlorobenzyl chloride, to obtain 130 mg of a solid product.

$^1$H-NMR (300 MHz, CDCl$_3$-d): δ 1.56-1.62 (m, 2H); 1.89-1.92 (m, 2H); 2.19 (s, 3H); 2.72 (s, 1H); 2.82-2.89 (m, 2H); 3.56 (s, 2H); 3.88 (s, 3H); 4.38-4.41 (m, 2H); 5.84 (s, 1H); 6.98-7.02 (t, 1H); 7.27-7.29 (m, 2H); 8.32 (s, 1H). MS (TOF) 330.4 (M+).

EXAMPLE 63

N-methyl-N-(3-chlorobenzyl)-N-[1-(6-methoxypy-rimidin-4-yl)piperidin-4-yl]amine (Mol-Hsp70-131)

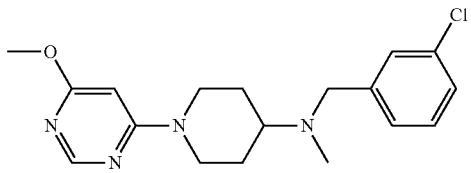 [SMILES: COc1cc(N2CCC(N(C)Cc3cccc(Cl)c3)CC2)ncn1]

The method of Example 43 was carried out, except for the use of 4,6-dichloropyrimidine in place of 2,4-dichloropyrimidine, and the use of m-chlorobenzyl chloride in place of o-chlorobenzyl chloride, to obtain 153 mg of a solid product.

$^1$H-NMR (300 MHz, CDCl$_3$-d): δ 1.55-1.62 (m, 2H); 1.89-1.92 (m, 2H); 2.20 (s, 3H); 2.72 (m, 1H); 2.83-2.89 (m, 2H); 3.57 (m, 2H); 3.91 (s, 3H); 4.38-4.41 (m, 2H); 5.83 (s, 1H); 7.23 (m, 3H); 7.34 (s, 1H); 8.32 (s, 1H). MS (TOF) 346.9 (M+).

EXAMPLE 64

N-methyl-N-(2-fluoro-6-chlorobenzyl)-N-[1-(6-methoxypyrimidin-4-yl)piperidin-4-yl] amine (Mol-Hsp70-132)

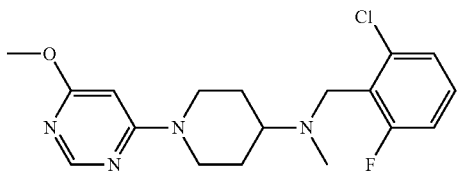

The method of Example 43 was carried out, except for the use of 4,6-dichloropyrimidine in place of 2,4-dichloropyrimidine, and the use of 2-fluoro-6-chlorobenzyl chloride in place of o-chlorobenzyl chloride, to obtain 153 mg of a solid product.

$^1$H-NMR (300 MHz, CDCl$_3$-d): δ 1.59-1.68 (m, 2H); 1.94-1.96 (m, 2H); 2.25 (s, 3H); 2.75 (m, 1H); 2.84-2.87 (m, 2H); 3.73 (s, 2H); 3.91 (s, 3H); 4.42-4.45 (m, 2H); 5.84 (s, 1H); 6.99 (t, 1H); 7.19 (d, 2H); 8.32 (s, 1H). MS (TOF) 364.8 (M+).

EXAMPLE 65

N-methyl-N-(2-cyanobenzyl)-N-[1-(6-methoxypyrimidin-4-yl)piperidin-4-yl]amine (Mol-Hsp70-133)

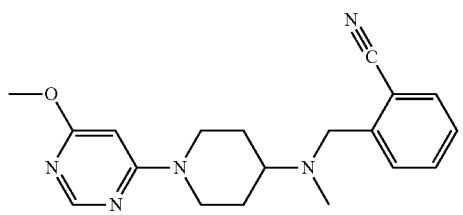 [SMILES: COc1cc(N2CCC(N(C)Cc3ccccc3C#N)CC2)ncn1]

The method of Example 43 was carried out, except for the use of 4,6-dichloropyrimidine in place of 2,4-dichloropyrimidine, and the use of o-cyanobenzyl chloride in place of o-chlorobenzyl chloride, to obtain 153 mg of a solid product.

$^1$H-NMR (300 MHz, CDCl$_3$-d): δ 1.58-1.62 (m, 2H); 1.93-1.96 (m, 2H); 2.20 (s, 3H); 2.72 (m, 1H); 2.83-2.87 (m, 2H); 3.78 (s, 2H); 3.91 (s, 3H); 4.41-4.44 (m, 2H); 5.84 (s, 1H); 7.35 (s, 3H); 7.54 (s, 1H); 7.63-7.65 (d, 1H); 8.32 (s, 1H). MS (TOF) 337.4 (M+).

EXAMPLE 66

N-methyl-N-(p-cyanobenzyl)-N-[1-(6-methoxypyrimidin-4-yl)piperidin-4-yl]amine (Mol-Hsp70-136)

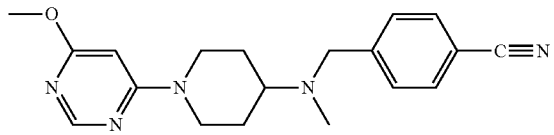

The method of Example 43 was carried out, except for the use of 4,6-dichloropyrimidine in place of 2,4-dichloropyrimidine, and the use of p-cyanobenzyl chloride in place of o-chlorobenzyl chloride, to obtain 153 mg of a solid product.

$^1$H-NMR (300 MHz, CDCl$_3$-d): δ 1.55-1.61 (m, 2H); 1.88-1.91 (m, 2H); 2.22 (s, 3H); 2.71 (m, 1H); 2.80-2.89 (m, 2H); 3.63 (s, 2H); 3.93 (s, 3H); 4.39-4.41 (d, 2H); 5.8 (s, 1H); 7.26 (s, 3H); 7.44-7.46 (d, 1H); 7.60-7.62 (d, 1H); 8.32 (s, 1H). MS (TOF) 337.4 (M+).

EXAMPLE 67

N-methyl-N-(2,5-dichlorobenzyl)-N-[1-(6-methoxypyrimidin-4-yl)piperidin-4-yl]amine (Mol-Hsp70-251)

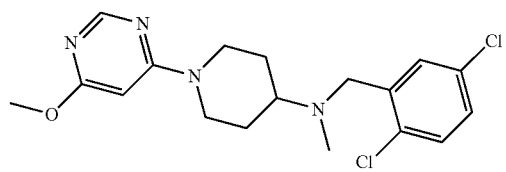 [SMILES: COc1cc(N2CCC(N(C)Cc3cc(Cl)ccc3Cl)CC2)ncn1]

The method of Example 43 was carried out, except for the use of 4,6-dichloropyrimidine in place of 2,4-dichloropyrimidine, and the use of 2,5-dichlorobenzyl chloride in place of o-chlorobenzyl chloride, to obtain 153 mg of a solid product.

$^1$H-NMR (300 MHz, CDCl$_3$-d): δ 1.59-1.62 (m, 2H); 1.91-1.94 (m, 2H); 2.25 (s, 3H); 2.75 (m, 1H); 2.85-2.92 (m, 2H); 3.66 (s, 2H); 3.93 (s, 3H); 4.41-4.44 (m, 2H); 5.86 (s, 1H); 7.23-7.25 (t, 1H); 7.38 (m, 1H); 7.45-7.47 (m, 1H); 8.34 (s, 1H). MS (TOF) 381.3 (M+).

EXAMPLE 68

N-methyl-N-(3-fluorobenzyl)-N-[1-(6-methoxypyrimidin-4-yl)piperidin-4-yl]amine (Mol-Hsp70-252)

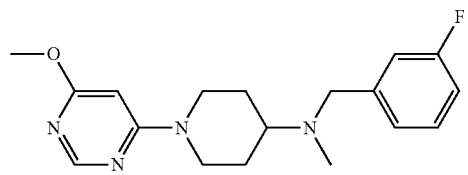 [SMILES: COc1cc(N2CCC(N(C)Cc3cccc(F)c3)CC2)ncn1]

The method of Example 43 was carried out, except for the use of 4,6-dichloropyrimidine in place of 2,4-dichloropyrimidine, and the use of 3-fluorobenzyl chloride in place of o-chlorobenzyl chloride, to obtain 153 mg of a solid product.

$^1$H-NMR (300 MHz, CDCl$_3$-d): δ 1.58-1.64 (m, 2H); 1.91-1.94 (m, 2H); 2.21 (s, 3H); 2.74 (m, 1H); 2.84-2.91 (m, 2H); 3.61 (m, 2H); 3.93 (s, 3H); 4.40-4.43 (m, 2H); 5.86 (s, 1H); 6.95 (t, 1H); 7.11 (m, 2H); 7.28-7.30 (s, 2H); 8.34 (s, 1H). MS (TOF) 330.4 (M+).

EXAMPLE 69

N-methyl-N-(4-cyanobenzyl)-N-[1-(2-methylthiopyrimidin-4-yl)piperidin-4-yl]amine hydrochloride

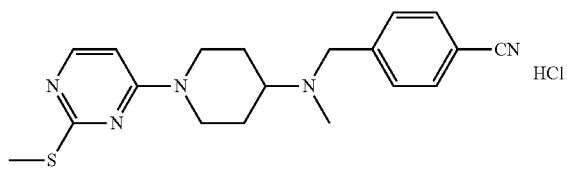

N-methyl-N-(4-cyanobenzyl)-N-[1-(2-methylthiopyrimidin-4-yl)piperidin-4-yl]amine was dissolved with ethyl acetate, diethyl ether hydrochloride was added dropwise slowly in ice bath, while white solid salt precipitated out slowly, till forming hydrochloride completely, followed by filtration to obtain 160 mg of N-methyl-N-(4-cyanobenzyl)-N-[1-(2-methylthiopyrimidin-4-yl) piperidin-4-yl]amine hydrochloride.

$^1$H-NMR (300 MHz, DMSO-d$_6$): δ 1.55-1.59 (m, 2H); 1.91-1.94 (d, 2H); 2.21 (s, 3H); 2.50 (s, 3H); 2.75 (m, 1H); 2.84-2.90 (t, 2H); 3.65 (s, 2H); 4.48 (d, 2H); 6.21-6.22 (d,

1H); 7.46-7.48 (d, 3H); 7.61-7.63 (d, 2H); 8.01-8.02 (d, 1H); 10.90 (S, 1H). Elemental analysis: C, 58.51; H, 6.22; Cl, 9.08; N, 17.97; S, 8.20.

EXAMPLE 70

N-methyl-N-(4-cyanobenzyl)-N-[1-(2-methylthiopyrimidin-4-yl)piperidin-4-yl]amine methanesulfonate

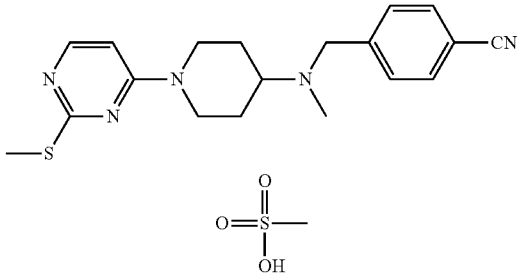

N-methyl-N-(4-cyanobenzyl)-N-[1-(2-methylthiopyrimidin-4-yl)piperidin-4-yl]amine was dissolved with ethyl acetate, methanesulfonic acid was added dropwise slowly in ice bath, while white solid salt precipitated out slowly, till forming methanesulfonate completely, followed by filtration to obtain 160 mg of N-methyl-N-(4-cyanobenzyl)-N-[1-(2-methylthiopyrimidin-4-yl) piperidin-4-yl]amine methanesulfonate.

$^1$H-NMR (300 MHz, DMSO-$d_6$): δ 1.55-1.59 (m, 2H); 1.91-1.94 (d, 2H); 2.20 (s, 1H); 2.21 (s, 3H); 2.50 (s, 3H); 2.75 (m, 1H); 2.84-2.90 (t, 2H); 3.29 (s, 3H); 3.65 (s, 2H); 4.48 (d, 2H); 6.21-6.22 (d, 1H); 7.46-7.48 (d, 3H); 7.61-7.63 (d, 2H); 8.01-8.02 (d, 1H). Elemental analysis: C, 53.42; H, 6.06; N, 15.59; 0, 10.69; S, 14.24.

EXAMPLE 71

N-methyl-N-(3-cyanobenzyl)-N-[1-(4-methoxypyrimidin-2-yl)piperidin-4-yl]amine (Mol-Hsp70-411)

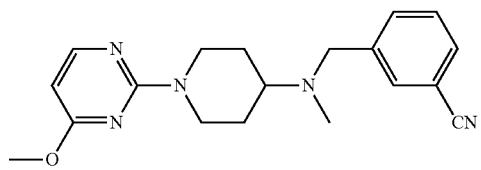 [SMILES: COc1ccnc(N2CCC(N(C)Cc3cccc(C#N)c3)CC2)n1]

The method of Example 43 was carried out, except for the use of 3-cyanobenzyl chloride in place of o-chlorobenzyl chloride, to obtain 153 mg of a solid product.

$^1$H-NMR (300 MHz, CDCl$_3$-d): δ 1.55-1.58 (m, 2H); 1.88-1.91 (d, 2H); 2.20 (s, 3H); 2.82-2.88 (s, 3H); 3.61 (s, 2H); 3.89 (s, 3H); 4.83-4.86 (d, 2H); 5.95-5.97 (d, 1H); 7.41-7.43 (m, 1H); 7.52-7.57 (m, 2H); 7.66-7.67 (s, 1H); 8.04-8.05 (d, 1H). MS (TOF) 337.4 (M+).

EXAMPLE 72

N-methyl-N-(3-cyanobenzyl)-N-[1-(2-methylthiopyrimidin-4-yl)piperidin-4-yl]amine (Mol-Hsp70-412)

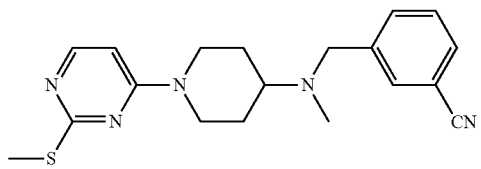 [SMILES: CSc1nccc(N2CCC(N(C)Cc3cccc(C#N)c3)CC2)n1]

The method of Example 35 was carried out, except for the use of 3-cyanobenzyl chloride in place of p-fluorobenzyl chloride, to obtain 167 mg of a solid product.

$^1$H-NMR (300 MHz, DMSO-$d_6$): δ 1.55-1.59 (m, 2H); 1.91-1.94 (d, 2H); 2.20 (s, 1H); 2.21 (s, 3H); 2.50 (s, 3H); 2.75 (m, 1H); 2.84-2.90 (t, 2H); 3.29 (s, 3H); 3.65 (s, 2H); 4.48 (d, 2H); 6.21-6.22 (d, 1H); 7.46-7.48 (d, 3H); 7.61-7.63 (d, 2H); 8.01-8.02 (d, 1H). MS (TOF) 353.5 (M+).

EXAMPLE 73

N-methyl-N-(3-cyanobenzyl)-N-[1-(2-chloropyrimidin-4-yl)piperidin-4-yl]amine (Mol-Hsp70-413)

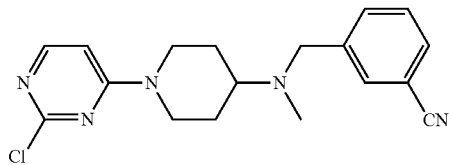 [SMILES: CN(Cc1cccc(C#N)c1)C1CCN(c2ccnc(Cl)n2)CC1]

The method of Example 43 was carried out, except for not performing the second step reaction, and the use of 3-cyanobenzyl chloride in place of o-chlorobenzyl chloride, to obtain 167 mg of a solid product.

$^1$H-NMR (300 MHz, DMSO-$d_6$): δ 1.58-1.61 (m, 2H); 1.94-1.97 (d, 2H); 2.20 (s, 3H); 2.77 (s, 1H); 2.90-2.96 (m, 2H); 3.63 (s, 2H); 4.49 (s, 2H); 6.41-6.43 (d, 1H); 7.42-7.45 (m, 1H); 7.54-7.56 (d, 2H); 7.66 (s, 1H); 8.02-8.04 (d, 1H). MS (TOF) 341.8 (M+).

EXAMPLE 74

N-methyl-N-(3-cyanobenzyl)-N-[1-(4-methylthiopyrimidin-2-yl)piperidin-4-yl]amine (Mol-Hsp70-414)

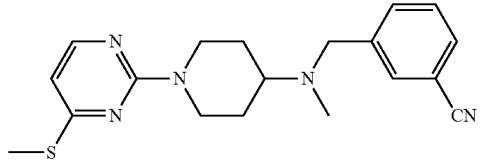 [SMILES: CSc1ccnc(N2CCC(N(C)Cc3cccc(C#N)c3)CC2)n1]

The method of Example 35 was carried out, except for the use of 3-cyanobenzyl chloride in place of p-fluorobenzyl chloride, to obtain 153 mg of a solid product.

$^1$H-NMR (300 MHz, CDCl$_3$-d): δ 1.55-1.61 (m, 2H); 1.88-1.91 (d, 2H); 2.20 (s, 3H); 2.73 (m, 1H); 2.82-2.88 (m, 2H); 3.62 (s, 2H); 4.86-4.89 (d, 2H); 6.38-6.39 (d, 1H); 7.40-7.42 (m, 1H); 7.53-7.55 (m, 2H); 7.67 (s, 1H); 7.96-7.99 (d, 1H). MS (TOF) 353.3 (M+).

EXAMPLE 75

N-methyl-N-(3-cyanobenzyl)-N-[1-(4-chloropyrimidin-2-yl)piperidin-4-yl]amine (Mol-Hsp70-415)

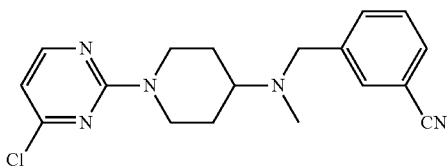 [SMILES: CN(Cc1cccc(C#N)c1)C1CCN(c2nccc(Cl)n2)CC1]

The method of Example 43 was carried out, except for not performing the second step reaction, and the use of 3-cyanobenzyl chloride in place of o-chlorobenzyl chloride, to obtain 167 mg of a solid product.

$^1$H-NMR (300 MHz, CDCl$_3$-d): δ 1.55-1.58 (m, 2H); 1.88-1.93 (d, 2H); 2.20 (s, 3H); 2.86 (m, 1H); 2.88-2.92 (m, 2H); 3.62 (s, 2H); 4.82-4.84 (d, 2H); 6.47-6.49 (d, 1H); 7.42-7.44 (m, 1H); 7.53-7.55 (m, 2H); 7.66 (s, 1H); 8.01-8.02 (d, 1H). MS (TOF) 341.8 (M+).

EXAMPLE 76

N-methyl-N-(4-cyanobenzyl)-N-[1-(4-chloropyrimidin-2-yl)piperidin-4-yl]amine(Mol-Hsp 70-416)

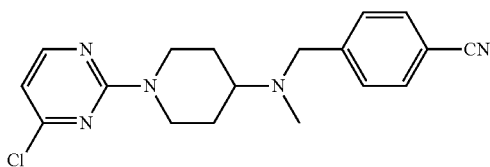 [SMILES: CN(Cc1ccc(C#N)cc1)C1CCN(c2nccc(Cl)n2)CC1]

The method of Example 43 was carried out, except for the use of 4-cyanobenzyl chloride in place of o-chlorobenzyl chloride, to obtain 167 mg of a solid product.

$^1$H-NMR (300 MHz, DMSO-d$_6$): δ 1.51-1.60 (m, 2H); 1.88-1.92 (d, 2H); 2.20 (s, 3H); 2.86 (m, 1H); 2.85-2.88 (m, 2H); 3.64 (s, 2H); 4.80-4.84 (d, 2H); 6.48-6.49 (d, 1H); 7.45-7.47 (m, 2H); 7.60-7.62 (m, 2H); 8.14-8.15 (d, 1H). MS (TOF) 341.8 (M+).

EXAMPLE 77

N-(4-cyanobenzyl)-N-[1-(2-methoxypyrimidin-4-yl)piperidin-4-yl]amine (Mol-Hsp70-417)

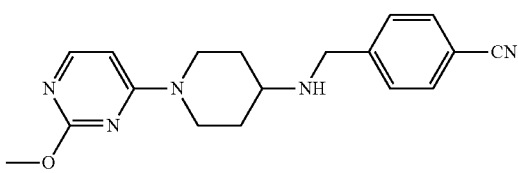 [SMILES: COc1nccc(N2CCC(NCc3ccc(C#N)cc3)CC2)n1]

The method of Example 43 was carried out, except for the use of tert-butyl N-(piperidin-4-yl)carbamate in place of tert-butyl N-methyl-N-(piperidin-4-yl)carbamate, and the use of 4-cyanobenzyl chloride in place of o-chlorobenzyl chloride, to obtain 167 mg of a solid product.

$^1$H-NMR (300 MHz, CDCl$_3$-d: δ1.38-1.43 (m, 2H); 1.96-2.00 (d, 2H); 2.75 (m, 1H); 3.01-3.04 (m, 2H); 3.90 (s, 5H); 4.28-4.31 (d, 2H); 6.18-6.19 (d, 1H); 7.47-7.49 (d, 2H); 7.61-7.63 (d, 2H); 7.99-8.01 (d, 1H). MS (TOF) 323.4 (M+).

EXAMPLE 78

N-methyl-N-(4-cyanobenzyl)-N-[1-(2-ethoxypyrimidin-4-yl)piperidin-4-yl]amine (Mol-Hsp70-418)

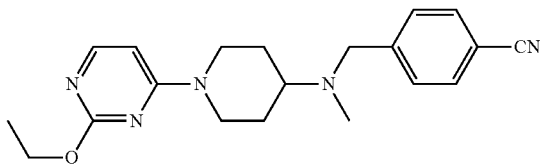 [SMILES: CCOc1nccc(N2CCC(N(C)Cc3ccc(C#N)cc3)CC2)n1]

The method of Example 43 was carried out, except for the use of sodium ethoxide in place of sodium methoxide, and the use of 4-cyanobenzyl chloride in place of o-chlorobenzyl chloride, to obtain 167 mg of a solid product.

$^1$H-NMR (300 MHz, CDCl$_3$-d): δ 1.39-1.42 (t, 3H); 1.57-1.58 (m, 2H); 1.89-1.92 (d, 2H); 2.21 (s, 3H); 2.50 (s, 3H); 2.75 (m, 1H); 2.83-2.90 (t, 2H); 3.64 (s, 2H); 4.31-4.37 (m, 2H); 4.45 (m, 2H); 6.17-6.20 (d, 1H); 7.45-7.47 (d, 2H); 7.60-7.62 (d, 2H); 7.99-8.01 (d, 1H). MS (TOF) 351.4 (M+).

EXAMPLE 79

N-methyl-N-(3-cyanobenzyl)-N-[1-(2-ethoxypyrimidin-4-yl)piperidin-4-yl]amine (Mol-Hsp70-419)

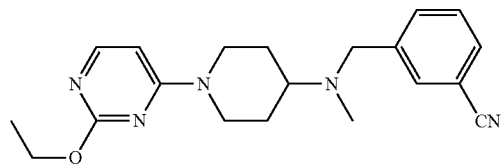 [SMILES: CCOc1nccc(N2CCC(N(C)Cc3cccc(C#N)c3)CC2)n1]

The method of Example 43 was carried out, except for the use of sodium ethoxide in place of sodium methoxide, and the use of 3-cyanobenzyl chloride in place of o-chlorobenzyl chloride, to obtain 167 mg of a solid product.

$^1$H-NMR (300 MHz, CDCl$_3$-d): δ 1.39-1.42 (t, 3H); 1.58-1.61 (m, 2H); 1.94-1.97 (d, 2H); 2.21 (s, 3H); 2.50 (s, 3H); 2.75 (m, 1H); 2.83-2.90 (t, 2H); 3.79 (s, 2H); 4.32-4.37 (m, 2H); 4.50 (m, 2H); 6.18-6.20 (d, 1H); 7.34-7.36 (m, 1H); 7.54-7.55 (d, 2H); 7.63 (m, 1H); 7.99-8.01 (d, 1H). MS (TOF) 351.4 (M+).

EXAMPLE 80

N-methyl-N-(2-fluorobenzyl)-N-[1-(2-ethoxypyrimidin-4-yl)piperidin-4-yl]amine

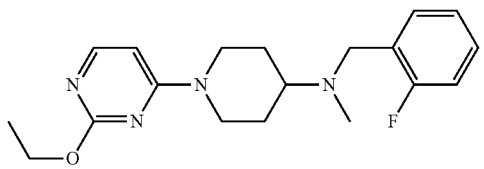 [SMILES: CCOc1nccc(N2CCC(N(C)Cc3ccccc3F)CC2)n1]

The method of Example 43 was carried out, except for the use of sodium ethoxide in place of sodium methoxide, and the use of 2-fluorobenzyl chloride in place of o-chlorobenzyl chloride, to obtain 167 mg of a solid product.

$^1$H-NMR (300 MHz, CDCl$_3$-d): δ 1.39-1.42 (t, 3H); 1.58-1.61 (m, 2H); 1.94-1.97 (d, 2H); 2.21 (s, 3H); 2.50 (s, 3H); 2.75 (m, 1H); 2.83-2.90 (t, 2H); 3.79 (s, 2H); 4.32-4.37 (m, 2H); 4.50 (m, 2H); 6.19-6.21 (d, 1H); 7.03-7.05 (m, 1H); 7.12-7.14 (m, 1H); 7.23-7.25 (m, 1H); 7.40 (m, 1H); 8.00-8.02 (d, 1H). MS (TOF) 344.4 (M+).

EXAMPLE 81

N-methyl-N-(2,6-difluorobenzyl)-N-[1-(2-methoxypyrimidin-4-yl)piperidin-4-yl]amine (Mol-Hsp70-420)

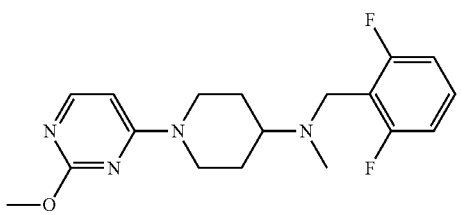 [SMILES: COc1nccc(N2CCC(N(C)Cc3c(F)cccc3F)CC2)n1]

The method of Example 43 was carried out, except for the use of 2,6-difluorobenzyl chloride in place of o-chlorobenzyl chloride, to obtain 167 mg of a solid product.

$^1$H-NMR (300 MHz, CDCl$_3$-d): δ 1.59-1.62 (m, 2H); 1.95-1.98 (d, 2H); 2.28 (s, 3H); 2.77 (m, 1H); 2.87-2.93 (t, 2H); 3.69 (s, 2H); 3.92 (s, 3H); 4.48 (m, 2H); 6.20-6.21 (d, 1H); 6.87-6.90 (m, 2H); 7.24-7.26 (m, 1H); 7.63 (m, 1H); 8.00-8.02 (d, 1H). MS (TOF) 348.4 (M+).

EXAMPLE 82

N-methyl-N-(2-fluorobenzyl)-N-[1-(2-methoxypyrimidin-4-yl)piperidin-4-yl]amine (Mol-Hsp70-421)

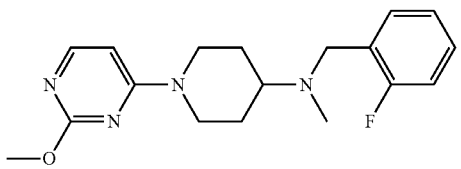

The method of Example 43 was carried out, except for the use of 2-fluorobenzyl chloride in place of o-chlorobenzyl chloride, to obtain 167 mg of a solid product.

$^1$H-NMR (300 MHz, CDCl$_3$-d): δ 1.59-1.62 (m, 2H); 1.94-1.97 (d, 2H); 2.26 (s, 3H); 2.77 (m, 1H); 2.85-2.91 (t, 2H); 3.67 (s, 2H); 3.93 (s, 3H); 4.48 (m, 2H); 6.19-6.21 (d, 1H); 7.03-7.05 (m, 1H); 7.12-7.14 (m, 1H); 7.23-7.25 (m, 1H); 7.40 (m, 1H); 8.00-8.02 (d, 1H). MS (TOF) 330.4 (M+).

EXAMPLE 83

N-methyl-N-(4-chlorobenzyl)-N-[1-(2-methoxypyrimidin-4-yl)piperidin-4-yl]amine (Mol-Hsp70-422)

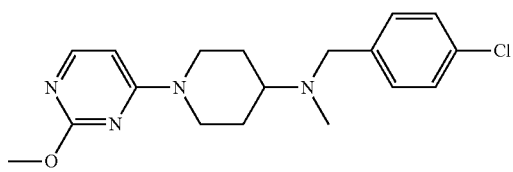

The method of Example 43 was carried out, except for the use of 4-chlorobenzyl chloride in place of o-chlorobenzyl chloride, to obtain 167 mg of a solid product.

$^1$H-NMR (300 MHz, DMSO-d$_6$): δ 1.40-1.44 (m, 2H); 1.80-1.83 (m, 2H); 2.08 (s, 3H); 2.70 (m, 1H); 2.82-2.88 (t, 2H); 3.53 (s, 2H); 3.78 (s, 3H); 4.11 (m, 2H); 6.48-6.50 (d, 1H); 7.31-7.35 (m, 4H); 7.97-7.99 (d, 1H). MS (TOF) 346.9 (M+).

EXAMPLE 84

N-methyl-N-(4-chlorobenzyl)-N-[1-(2-methylthiopyrimidin-4-yl)piperidin-4-yl]amine (Mol-Hsp70-423)

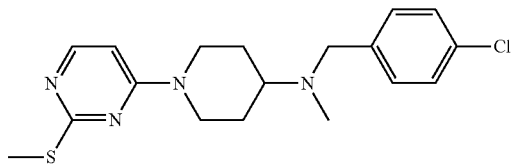 [SMILES: CSc1nccc(N2CCC(N(C)Cc3ccc(Cl)cc3)CC2)n1]

The method of Example 35 was carried out, except for the use of 4-chlorobenzyl chloride in place of p-fluorobenzyl chloride, to obtain 167 mg of a solid product.

$^1$H-NMR (300 MHz, DMSO-d$_6$): δ 1.41-1.44 (m, 2H); 1.81-1.84 (m, 2H); 2.08 (s, 3H); 2.70 (m, 1H); 2.82-2.88 (t, 2H); 3.53 (s, 2H); 3.78 (s, 3H); 4.11 (m, 2H); 6.54-6.56 (d, 1H); 7.33-7.37 (m, 4H); 7.98-7.99 (d, 1H). MS (TOF) 362.9 (M+).

EXAMPLE 85

N-methyl-N-(2-fluorobenzyl)-N-[1-(2-methylthiopyrimidin-4-yl)piperidin-4-yl]amine (Mol-Hsp70-424)

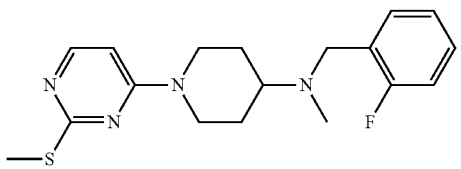 [SMILES: CSc1nccc(N2CCC(N(C)Cc3ccccc3F)CC2)n1]

The method of Example 35 was carried out, except for the use of 2-fluorobenzyl chloride in place of p-fluorobenzyl chloride, to obtain 167 mg of a solid product.

$^1$H-NMR (300 MHz, CDCl$_3$-d): δ 1.55-1.64 (m, 2H); 1.97 (d, 2H); 2.26 (s, 3H); 2.78 (m, 3H); 2.84-2.91 (m, 3H); 3.69 (s, 2H); 4.49 (m, 2H); 6.20-6.21 (d, 1H); 7.01-7.06 (m, 1H); 7.12-7.14 (m, 1H); 7.23-7.25 (m, 1H); 7.40 (m, 1H); 8.00-8.02 (d, 1H). MS (TOF) 346.9 (M+).

EXAMPLE 86

N-methyl-N-(2,6-difluorobenzyl)-N-[1-(2-methylthiopyrimidin-4-yl)piperidin-4-yl]amine (Mol-Hsp70-425)

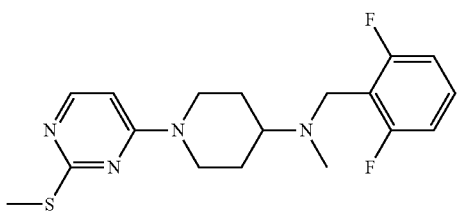 [SMILES: CSc1nccc(N2CCC(N(C)Cc3c(F)cccc3F)CC2)n1]

The method of Example 35 was carried out, except for the use of 2,6-difluorobenzyl chloride in place of p-fluorobenzyl chloride, to obtain 167 mg of a solid product.

$^1$H-NMR (300 MHz, CDCl$_3$-d): δ 1.59-1.62 (m, 2H); 1.95-1.98 (d, 2H); 2.27 (s, 3H); 2.50 (s, 3H); 2.77 (m, 1H); 2.87-2.93 (t, 2H); 3.67 (s, 2H); 4.48 (m, 2H); 6.21-6.22 (d, 1H); 6.86-6.90 (m, 2H); 7.21-7.23 (m, 1H); 7.99-8.01 (d, 1H). MS (TOF) 364.5 (M+).

EXAMPLE 87

N-methyl-N-(3,5-dimethoxybenzyl)-N-[1-(2-ethoxypyrimidin-4-yl)piperidin-4-yl]amine (Mol-Hsp70-426)

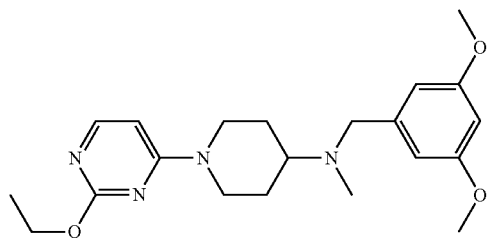 [SMILES: CCOc1nccc(N2CCC(N(C)Cc3cc(OC)cc(OC)c3)CC2)n1]

The method of Example 43 was carried out, except for the use of sodium ethoxide in place of sodium methoxide, and the use of 3,5-dimethoxybenzyl chloride in place of o-chlorobenzyl chloride, to obtain 167 mg of a solid product.

$^1$H-NMR (300 MHz, CDCl$_3$-d): δ 1.38-1.42 (m, 2H); 1.57-1.58 (m, 2H); 1.89-1.92 (d, 2H); 2.22 (s, 3H); 2.73 (m, 1H); 2.83-2.89 (m, 2H); 3.54 (s, 3H); 3.79-3.82 (s, 6H); 4.31-4.33 (m, 2H); 4.35-4.37 (m, 2H); 6.17-6.18 (d, 1H); 6.35-6.36 (s, 1H); 6.51 (s, 1H); 7.98-8.00 (d, 1H). MS (TOF) 386.5 (M+).

EXAMPLE 88

N-methyl-N-(2-nitrobenzyl)-N-[1-(2-ethoxypyrimidin-4-yl)piperidin-4-yl]amine (Mol-Hsp70-427)

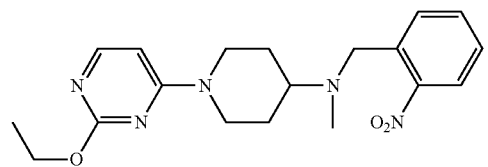

The method of Example 43 was carried out, except for the use of sodium ethoxide in place of sodium methoxide, and the use of 2-nitrobenzyl chloride in place of o-chlorobenzyl chloride, to obtain 167 mg of a solid product.

$^1$H-NMR (300 MHz, CDCl$_3$-d): δ 1.38-1.42 (m, 3H); 1.51-1.54 (m, 2H); 1.83-1.86 (d, 2H); 2.21 (s, 3H); 2.67-2.70 (m, 1H); 2.82-2.87 (t, 2H); 3.90 (s, 2H); 4.31-4.33 (m, 2H); 4.50 (m, 2H); 6.17-6.19 (d, 1H); 7.39-7.40 (m, 1H); 7.54-7.56 (m, 1H); 7.62-7.64 (m, 1H); 7.80-7.82 (m, 1H); 7.98-8.00 (d, 1H). MS (TOF) 344.4 (M+).

EXAMPLE 89

N-methyl-N-(2-nitrobenzyl)-N-[1-(2-methylthiopyrimidin-4-yl)piperidin-4-yl]amine (Mol-Hsp70-428)

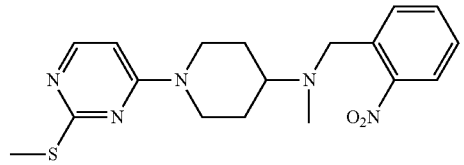 [SMILES: CSc1nccc(N2CCC(N(C)Cc3ccccc3[N+](=O)[O-])CC2)n1]

The method of Example 35 was carried out, except for the use of 2-nitrobenzyl chloride in place of p-fluorobenzyl chloride, to obtain 167 mg of a solid product.

$^1$H-NMR (300 MHz, CDCl$_3$-d): δ 1.52-1.55 (m, 2H); 1.85-1.88 (d, 2H); 2.13 (s, 3H); 2.50 (s, 3H); 2.70 (m, 1H); 2.82-2.88 (t, 2H); 3.91 (s, 2H); 4.8 (m, 2H); 6.20-6.22 (d, 1H); 7.39-7.40 (m, 1H); 7.54-7.56 (m, 1H); 7.62-7.64 (m, 1H); 7.80-7.82 (m, 1H); 7.99-8.01 (d, 1H). MS (TOF) 373.5 (M+).

EXAMPLE 90

N-methyl-N-(2-nitrobenzyl)-N-[1-(2-methoxypyrimidin-4-yl)piperidin-4-yl]amine (Mol-Hsp70-429)

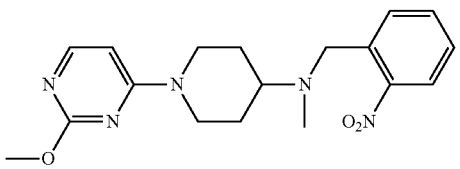

The method of Example 43 was carried out, except for the use of 2-nitrobenzyl chloride in place of o-chlorobenzyl chloride, to obtain 167 mg of a solid product.

$^1$H-NMR (300 MHz, CDCl$_3$-d): δ 1.52-1.55 (m, 2H); 1.84-1.90 (d, 2H); 2.13 (s, 3H); 2.68 (m, 1H); 2.82-2.89 (t, 2H); 3.92 (s, 5H); 4.47 (m, 2H); 6.18-6.20 (d, 1H); 7.40-7.41 (m, 1H); 7.52-7.56 (m, 1H); 7.63-7.65 (m, 1H); 7.80-7.82 (m, 1H); 8.00-8.02 (d, 1H). MS (TOF) 357.4 (M+).

EXAMPLE 91

N-methyl-N-(3,5-dimethoxybenzyl)-N-[1-(2-methoxypyrimidin-4-yl)piperidin-4-yl]amine (Mol-Hsp70-430)

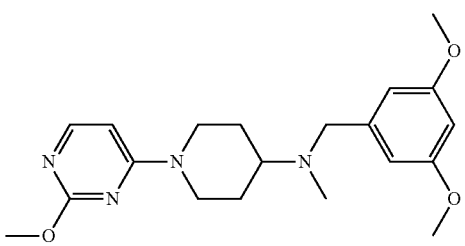 [SMILES: COc1cc(CN(C)C2CCN(c3ccnc(OC)n3)CC2)cc(OC)c1]

The method of Example 43 was carried out, except for the use of 3,5-dimethoxybenzyl chloride in place of o-chlorobenzyl chloride, to obtain 167 mg of a solid product.

$^1$H-NMR (300 MHz, CDCl$_3$-d): δ 1.60-1.42 (m, 4H); 1.94 (m, 1H); 2.25 (s, 2H); 2.84-2.90 (t, 2H); 3.57-3.62 (m, 1H); 3.79 (s, 6H); 3.91 (s, 3H); 4.48 (m, 2H); 6.15-6.20 (d, 1H); 6.37 (s, 1H); 6.54 (s, 1H); 8.01-8.02 (d, 1H). MS (TOF) 372.5 (M+).

EXAMPLE 92

N-(2,6-dichlorobenzyl)-N-[1-(2-methoxypyrimidin-4-yl)piperidin-4-yl]amine (Mol-Hsp70-431)

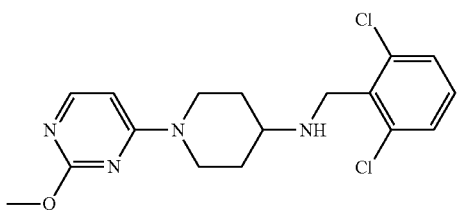 [SMILES: COc1nccc(N2CCC(NCc3c(Cl)cccc3Cl)CC2)n1]

The method of Example 43 was carried out, except for the use of tert-butyl N-(piperidin-4-yl)carbamate in place of tert-butyl N-methyl-N-(piperidin-4-yl)carbamate, and the use of 2,6-dichlorobenzyl chloride in place of o-chlorobenzyl chloride, to obtain 167 mg of a solid product.

$^1$H-NMR (300 MHz, CDCl$_3$-d): δ 1.42-1.45 (m, 2H); 1.98-2.01 (d, 2H); 2.77 (m, 1H); 3.03-3.08 (t, 2H); 3.91 (s, 3H); 4.13 (s, 2H); 4.28 (m, 2H); 6.18-6.19 (d, 1H); 7.15-7.17 (m, 2H); 7.30-7.32 (m, 1H); 8.00-8.02 (d, 1H). MS (TOF) 367.5 (M+).

EXAMPLE 93

N-(3,5-dimethoxybenzyl)-N-[1-(2-methoxypyrimidin-4-yl)piperidin-4-yl]amine (Mol-Hsp70-432)

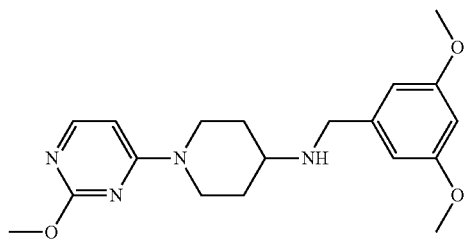

The method of Example 43 was carried out, except for the use of tert-butyl N-(piperidin-4-yl)carbamate in place of tert-butyl N-methyl-N-(piperidin-4-yl)carbamate, and the use of 3,5-dimethoxybenzyl chloride in place of o-chlorobenzyl chloride, to obtain 167 mg of a solid product.

$^1$H-NMR (300 MHz, CDCl$_3$-d): δ 1.43-1.45 (m, 2H); 1.97-1.99 (d, 2H); 2.73 (m, 1H); 2.97-3.30 (m, 2H); 3.77-3.80 (m, 8H); 3.91 (s, 3H); 4.28-4.31 (m, 2H); 6.17-6.19 (d, 2H); 6.37 (s, 1H); 6.51 (s, 2H); 7.99-8.01 (d, 1H). MS (TOF) 358.4 (M+).

EXAMPLE 94

N-(2-cyanobenzyl)-N-[1-(2-methoxypyrimidin-4-yl)piperidin-4-yl]amine (Mol-Hsp70-442)

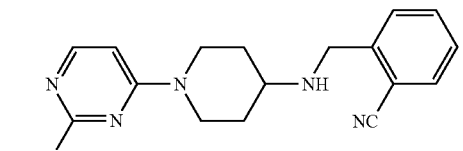

The method of Example 43 was carried out, except for the use of tert-butyl N-(piperidin-4-yl)carbamate in place of tert-butyl N-methyl-N-(piperidin-4-yl)carbamate, and the use of 2-cyanobenzyl chloride in place of o-chlorobenzyl chloride, to obtain 167 mg of a solid product.

$^1$H-NMR (300 MHz, CDCl$_3$-d): δ 1.40-1.45 (m, 2H); 1.70-1.80 (d, 2H); 1.97-2.00 (d, 2H); 2.68 (m, 1H); 3.02-3.07 (t, 2H); 3.92 (s, 3H); 4.10 (s, 2H); 4.29 (m, 2H); 6.18-6.20 (d, 1H); 7.44-7.45 (m, 1H); 7.60-7.67 (m, 2H); 7.94-8.01 (m, 2H). MS (TOF) 323.4 (M+).

EXAMPLE 95

N-(2-nitrobenzyl)-N-[1-(2-methoxypyrimidin-4-yl)piperidin-4-yl]amine (Mol-Hsp70-433)

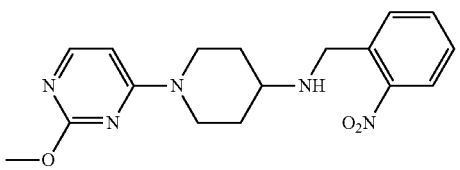 [SMILES: COc1nccc(N2CCC(NCc3ccccc3[N+](=O)[O-])CC2)n1]

The method of Example 43 was carried out, except for the use of tert-butyl N-(piperidin-4-yl)carbamate in place of tert-butyl N-methyl-N-(piperidin-4-yl)carbamate, and the use of 2-nitrobenzyl chloride in place of o-chlorobenzyl chloride, to obtain 167 mg of a solid product.

$^1$H-NMR (300 MHz, CDCl$_3$-d): δ 1.40-1.45 (m, 2H); 1.70-1.80 (d, 2H); 1.97-2.00 (d, 2H); 2.68 (m, 1H); 3.02-3.07 (t, 2H); 3.92 (s, 3H); 4.10 (s, 2H); 4.29 (m, 2H); 6.18-6.20 (d, 1H); 7.44-7.45 (m, 1H); 7.60-7.67 (m, 2H); 7.94-8.01 (m, 2H). MS (TOF) 343.4 (M+).

EXAMPLE 96

N-(4-cyanobenzyl)-N-[1-(2-ethoxypyrimidin-4-yl)piperidin-4-yl]amine (Mol-Hsp70-434)

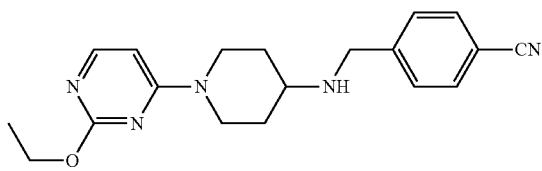

The method of Example 43 was carried out, except for the use of tert-butyl N-(piperidin-4-yl)carbamate in place of tert-butyl N-methyl-N-(piperidin-4-yl)carbamate, the use of sodium ethoxide in place of sodium methoxide, and the use of 4-cyanobenzyl chloride in place of o-chlorobenzyl chloride, to obtain 167 mg of a solid product.

$^1$H-NMR (300 MHz, CDCl$_3$-d): δ 1.38-1.42 (t, 3H); 1.66 (m, 1H); 1.95-1.99 (d, 2H); 2.70 (m, 1H); 2.98-3.04 (t, 2H); 3.92 (s, 3H); 4.30-4.35 (m, 4H); 6.16-6.18 (d, 1H); 6.46-6.48 (d, 2H); 7.61-7.63 (d, 2H); 7.98-8.00 (d, 1H). MS (TOF) 337.4 (M+).

EXAMPLE 97

N-(2,6-dichlorobenzyl)-N-[1-(2-ethoxypyrimidin-4-yl)piperidin-4-yl]amine (Mol-Hsp70-435)

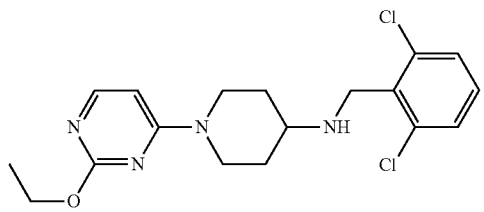 [SMILES: CCOc1nccc(N2CCC(NCc3c(Cl)cccc3Cl)CC2)n1]

The method of Example 43 was carried out, except for the use of tert-butyl N-(piperidin-4-yl)carbamate in place of tert-butyl N-methyl-N-(piperidin-4-yl)carbamate, the use of sodium ethoxide in place of sodium methoxide, and the use of 2,6-dichlorobenzyl chloride in place of o-chlorobenzyl chloride, to obtain 167 mg of a solid product.

$^1$H-NMR (300 MHz, CDCl$_3$-d): δ 1.38-1.42 (t, 3H); 1.97-2.05 (m, 3H); 2.70 (m, 1H); 3.02-3.09 (m, 2H); 4.12 (s, 3H); 4.31-4.36 (m, 4H); 6.16-6.18 (d, 1H); 7.15-7.17 (m, 1H); 7.30-7.32 (d, 2H); 7.98-8.00 (d, 1H). MS (TOF) 381.3 (M+).

EXAMPLE 98

N-methyl-N-(4-nitrobenzyl)-N-[1-(2-ethoxypyrimidin-4-yl)piperidin-4-yl]amine (Mol-Hsp70-436)

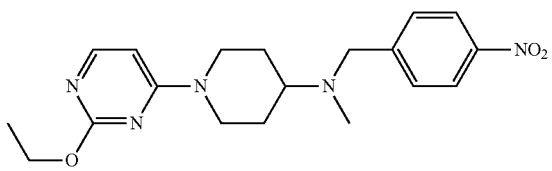

The method of Example 43 was carried out, except for the use of sodium ethoxide in place of sodium methoxide, and the use of 4-nitrobenzyl chloride in place of o-chlorobenzyl chloride, to obtain 167 mg of a solid product.

$^1$H-NMR (300 MHz, CDCl$_3$-d): δ 1.39-1.42 (t, 3H); 1.60-1.61 (m, 2H); 1.95-1.98 (m, 2H); 2.25 (s, 3H); 2.85-2.91 (m, 3H); 3.73 (s, 2H); 4.33-4.38 (m, 2H); 4.50 (m, 2H); 6.18-6.20 (d, 1H); 7.55-7.57 (d, 2H); 8.00-8.02 (d, 1H); 8.18-8.20 (d, 2H). MS (TOF) 371.4 (M+).

EXAMPLE 99

N-(2,6-difluorobenzyl)-N-[1-(2-ethoxypyrimidin-4-yl)piperidin-4-yl]amine (Mol-Hsp70-437)

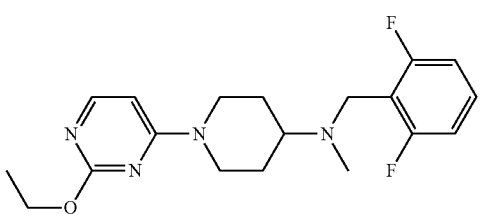 [SMILES: CCOc1nccc(N2CCC(N(C)Cc3c(F)cccc3F)CC2)n1]

The method of Example 43 was carried out, except for the use of sodium ethoxide in place of sodium methoxide, and the use of 2,6-difluorobenzyl chloride in place of o-chlorobenzyl chloride, to obtain 167 mg of a solid product.

$^1$H-NMR (300 MHz, CDCl$_3$-d): δ 1.38-1.42 (t, 3H); 1.97-2.05 (m, 3H); 2.70 (m, 1H); 3.02-3.09 (m, 2H); 4.12 (s, 3H); 4.31-4.36 (m, 4H); 6.16-6.18 (d, 1H); 7.15-7.17 (m, 1H); 7.30-7.32 (d, 2H); 7.98-8.00 (d, 1H). MS (TOF) 362.4 (M+).

EXAMPLE 100

N-methyl-N-(4-nitrobenzyl)-N-[1-(2-methoxypyrimidin-4-yl)piperidin-4-yl]amine (Mol-Hsp70-438)

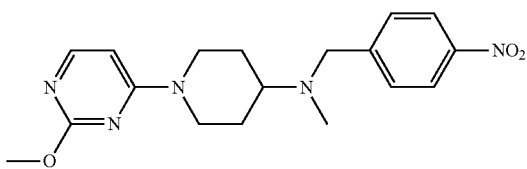

The method of Example 43 was carried out, except for the use of 4-nitrobenzyl chloride in place of o-chlorobenzyl chloride, to obtain 167 mg of a solid product.

$^1$H-NMR (300 MHz, CDCl$_3$-d): δ 1.55-1.62 (m, 2H); 1.90-1.93 (d, 2H); 2.11 (s, 3H); 2.74 (m, 1H); 2.85-2.91 (m, 2H); 3.68 (s, 2H); 3.93 (s, 3H); 4.47 (m, 2H); 6.19-6.20 (d, 1H); 7.50-7.52 (d, 2H); 8.01-8.03 (d, 1H); 8.17-8.19 (d, 2H). MS (TOF) 357.4 (M+).

EXAMPLE 101

N-methyl-N-(4-nitrobenzyl)-N-[1-(2-methylthiopyrimidin-4-yl)piperidin-4-yl]amine (Mol-Hsp70-439)

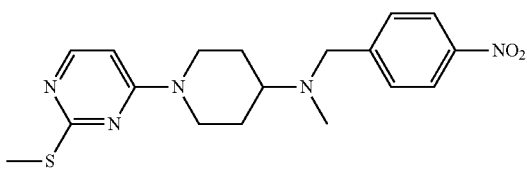 [SMILES: CSc1nccc(N2CCC(N(C)Cc3ccc([N+](=O)[O-])cc3)CC2)n1]

The method of Example 35 was carried out, except for the use of 4-nitrobenzyl chloride in place of p-fluorobenzyl chloride, to obtain 167 mg of a solid product.

$^1$H-NMR (300 MHz, CDCl$_3$-d): δ 1.56-1.63 (m, 2H); 1.93-1.96 (d, 2H); 2.22 (s, 3H); 2.50 (s, 3H); 2.74 (m, 1H); 2.84-2.90 (m, 2H); 3.71 (s, 2H); 4.50 (m, 2H); 6.20-6.22 (d, 1H); 7.52-7.54 (d, 2H); 8.00-8.02 (d, 1H); 8.18-8.20 (d, 2H). MS (TOF) 373.4 (M+).

EXAMPLE 102

N-methyl-N-(naphth-1-ylmethyl)-N-[1-(2-methoxypyrimidin-4-yl)piperidin-4-yl]amine (Mol-Hsp70-440)

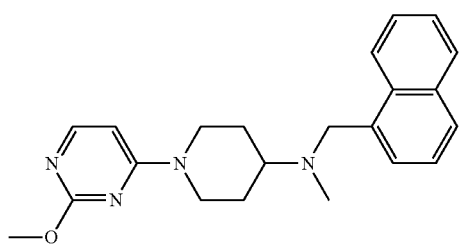 [SMILES: COc1nccc(N2CCC(N(C)Cc3cccc4ccccc34)CC2)n1]

The method of Example 43 was carried out, except for the use of 1-chloromethylnaphthalene in place of o-chlorobenzyl chloride, to obtain 167 mg of a solid product.

$^1$H-NMR (300 MHz, CDCl$_3$-d): δ 1.66-1.69 (m, 2H); 1.98-2.01 (d, 2H); 2.22 (s, 3H); 2.85-2.90 (m, 3H); 3.93 (s, 3H); 4.00 (s, 3H); 4.50 (m, 2H); 6.20-6.21 (d, 1H); 7.41-7.50 (m, 4H); 7.76-7.78 (d, 1H); 7.85-7.85 (d, 1H); 8.00-8.02 (d, 1H); 8.23-8.25 (d, 2H). MS (TOF) 362.5 (M+).

EXAMPLE 103

N-methyl-N-(naphth-1-ylmethyl)-N-[1-(2-ethoxypyrimidin-4-yl)piperidin-4-yl]amine (Mol-Hsp70-441)

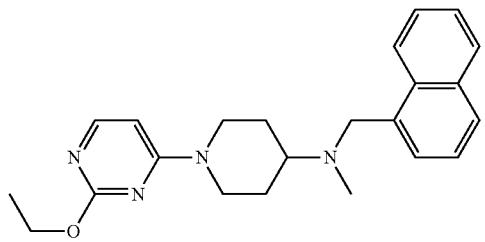 [SMILES: CCOc1nccc(N2CCC(N(C)Cc3cccc4ccccc34)CC2)n1]

The method of Example 43 was carried out, except for the use of sodium ethoxide in place of sodium methoxide, and the use of 1-chloromethylnaphthalene in place of o-chlorobenzyl chloride, to obtain 167 mg of a solid product.

$^1$H-NMR (300 MHz, CDCl$_3$-d): δ 1.39-1.42 (t, 3H); 1.66-1.69 (m, 2H); 1.98-2.01 (d, 2H); 2.22 (s, 3H); 2.83-2.86 (m, 3H); 4.05 (s, 2H); 4.32-4.38 (m, 2H); 4.60 (m, 2H); 6.18-6.20 (d, 1H); 7.41-7.49 (m, 4H); 7.77-7.79 (d, 1H); 7.85-7.85 (d, 1H); 7.99-8.01 (d, 1H); 8.23-8.25 (d, 2H). MS (TOF) 376.5 (M+).

EXAMPLE 104

N-methyl-N-(2,6-dichlorobenzyl)-N-[1-(2-methoxypyrimidin-4-yl)piperidin-4-yl]amine (Mol-Hsp70-443)

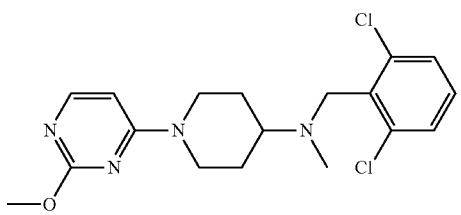 [SMILES: COc1nccc(N2CCC(N(C)Cc3c(Cl)cccc3Cl)CC2)n1]

The method of Example 43 was carried out, except for the use of 2,6-dichlorobenzyl chloride in place of o-chlorobenzyl chloride, to obtain 167 mg of a solid product.

$^1$H-NMR (300 MHz, DMSO-d$_6$): δ 1.45-1.52 (m, 2H); 1.81-1.85 (d, 2H); 2.08 (s, 3H); 2.78-2.87 (m, 3H); 3.78 (s, 5H); 4.46 (m, 2H); 6.49-6.51 (d, 1H); 7.30-7.34 (q, 1H); 7.45-7.47 (d, 2H); 7.97-7.98 (d, 1H). MS (TOF) 381.3 (M+).

EXAMPLE 105

Measurement of affinity between the compounds of Examples and Hsp70 according to the method described below Materials and Method 1. Instrument: BIACORE T100 Biomolecular Interaction Analysis (GE, USA)
2. Reagents: PBS Buffer (×10), P20, CM5 chip (GE, USA), Hsp70 (human, ADI-ESP-550-D), manufactured by Enzo Life Sciences.

Formulation of the Compound 30 mM mother liquor of the compound was formulated with DMSO, which was diluted to 2 mM application solution with DMSO before use. 5 µl of the application solution was taken and diluted with 95 µl 1.05×PBS to 100 µM, and then diluted in turn with PBS containing 5% DMSO to 10, 3, 1, 0.3, 0.1, 0.03, 0.01, 0.003, 0.3 µM. PBS containing 5% DMSO was used as solvent control.

Operating Procedures

1. Coupling of Hsp70 protein and CM5 chip

Hsp70 protein was diluted with 10 mmol/L sodium acetate buffer solution (pH 5.0) to 30 µg/ml, and coupled directly on a hydrophilic carboxylmethyl dextran matrix sensor chip M5 through normalized primary amine coupling reaction, RU=11209, and then the chip was balanced for 1-2 h with PBS Buffer at constant current.

2. Measurement of affinity between the compound and Hsp70 protein

At a flow rate of 30 µl/ml, with PBS containing 5% DMSO as mobile phase, at 25° C., the compound was introduced in the sequence of 0.003, 0.01, 0.03, 0.1, 0.3, 1, 3 and 10 µM, with binding time of 90 seconds, and dissociation time of 120 seconds.

3. Result analysis:

According to binding characteristics between the compounds and protein, the binding constant (equilibrium dissociation constant KD) between drugs and protein was calculated by selecting steady state model with the formula: Conc*Rmax/[conc+KD]+offset.

Test results are as follows:

TABLE 1

Binding constant between the compounds of Examples and Hsp70

| Name of the compound | KD (Mol/L) |
|---|---|
| Example 35 | $2.045 \times 10^{-7}$ |
| Example 57 | $2.811 \times 10^{-7}$ |
| Example 36 | $2.463 \times 10^{-7}$ |
| Example 12 | $1.999 \times 10^{-7}$ |
| Example 14 | $2.454 \times 10^{-7}$ |

EXAMPLE 106

Antitumor bioactivity evaluation of the compounds of Examples according to the method described below Test Materials

TABLE 2

Types of breast cancer cells used in Example 106:

| Name | Generation | Viability % |
|---|---|---|
| BT474 | P103 | 100 |
| BT/Lap$^R$1.0 | / | 97.12 |
| MDA-MB-361 | F72 | 97.76 |
| SK-BR3 | F28 | 95.95 |
| SK/Lap$^R$1.0 | / | 93.35 |
| MDA-MB-453 | F8 | 96.8 |

Note:
BT474, SK-BR3 are human breast cancer cell strains sensitive to lapatinib, BT/Lap$^R$, SK/Lap$^R$ are human breast cancer cell strains with secondary resistance to lapatinib, after being stimulated with lapatinib, MDA-MB-361, MDA-MB-453 are human breast cancer cell strains with natural resistance to lapatinib.

Lapatinib: 10 mM DMSO solution, BioVision, Cat: 1624-100, Lot: 50324

ATPlit kit: CellTiter-Glo Substrate, Promega, Part: G755B, Lot: 2513501, EXP: 2014-05

Experimental Procedures

Cells plating: a 100 mm culture dish with overgrown adherent cells was digested with 1 ml 0.25% trypsin (GIBCO) at 37° C. for 5 min, and the reaction was terminated with 2 ml culture medium (containing 10% FBS, GIBCO). The cells were scattered and collected, after counting, diluted to $1 \times 10^5$ cells/ml, and seeded into a 96-well plate at 50 µl/well, 5000 cells/well, excluding the peripheral circle of wells in which no cell was added, but PBS was added, 60 wells in total, and then incubated at 37° C. for 24 hours for adhering.

Addition of the compound and lapatinib: the test sample was diluted to a final concentration of 5 µM, and the culture medium with the corresponding compound solvent concentration was filled in the control well, the compound solvent concentration was kept consistent in each well, 5 parellel wells were set for each concentration, 25 µl each well, 25 µl culture medium (in combined group, 25 µl lapatinib was added till a final concentration of 1 µM) supplemented, followed by incubation at 37° C. for 72 hours.

Test after incubation at 37° C. for 72 hours: 50 µL of ATPlite kit substrate solution was added in each well, and vibrated for 3 min, followed by placing aside in darkness for 10 min, and then supernatant 100 µl/well was taken and placed on aluminescence test plate; the luminescence test plate that has been fully incubated was placed in a luminescence test instrument, to read luminescence value.

Data Processing

1. Cell survival rate (%)=Experimental group RLU/control group RLU×100%. The experimental data were subjected to data analysis and processing by utilizing GraphPad software.

2. The nature of interaction between two drugs was evaluated by using coefficient of drug interaction (CDI), CDI being calculated as follows: CDI=AB/(A×B)×100%. As calculated according to the number of viable cells (luminescence value), when CDI<1, the nature of interaction between two drugs is synergistic; when CDI<0.7, the synergism is very significant; when CDI=1, the nature of interaction between two drugs is additive; when CDI>1, the nature of interaction between two drugs is antagonistic.

The inhibitory rates of the resulting compounds of the present invention against six tumor cell strains were measured as follows:

TABLE 3

Inhibitory rates of compounds of Examples against six breast cancer cell strains

| Name of the compound | BT474 | BT/Lap$^R$ 1.0 | MDA-MB-361 | SK-BR3 | SKLap$^R$ 1.0 | MDA-MB-453 |
|---|---|---|---|---|---|---|
| lapatinib | 75.6 | 18 | 40.2 | 79 | 10.4 | 42.6 |
| Example 1 | 14.4 | 12.5 | 14.2 | 16.7 | 5.2 | 41.2 |
| Example 2 | 17.6 | 19.4 | 12.3 | 13.6 | 7.2 | 43.8 |
| Example 3 | 62.9 | 67.4 | 35.8 | 41.2 | 13.1 | 71.6 |
| Example 4 | 61.7 | 66.1 | 51.3 | 45.5 | 6.7 | 70.5 |
| Example 5 | 54.4 | 50.5 | 32.8 | 40.9 | 11.7 | 67.4 |
| Example 6 | 10.1 | 13.3 | 33.3 | 12.6 | 0.6 | 36.4 |
| Example 7 | 36.4 | 20.7 | 24.2 | 26 | 25.1 | 52.9 |
| Example 8 | 70.3 | 65.9 | 49.2 | 41.6 | 12 | 71.3 |
| Example 9 | 38.2 | 25.6 | 24.5 | 17.9 | 5.1 | 51.5 |
| Example 10 | 5.6 | 9.6 | 25.3 | 9.4 | 5.2 | 23.9 |
| Example 11 | 11 | 10.6 | 13.9 | 26.3 | 25.1 | 32.9 |
| Example 12 | 5.4 | 9.1 | 4.8 | 22.4 | 4.4 | 0.1 |
| Example 13 | 3.8 | 7.2 | 3.2 | 17.9 | 4.1 | 2.4 |
| Example 14 | −4.1 | 4 | −8.5 | 7.3 | 4.2 | 8.2 |
| Example 15 | 69.3 | 68.7 | 35.6 | 41.5 | 7.5 | 68.5 |
| Example 16 | 7.1 | 9 | −1.3 | 18.6 | −0.1 | 11 |
| Example 17 | 45.4 | 53.4 | 42.9 | 34.3 | 5.3 | 63.8 |
| Example 18 | 7.1 | 8.4 | 9.7 | 15.5 | 8.5 | 12.6 |
| Example 19 | 10.6 | 3.2 | 10.4 | 9.8 | 1.5 | 22.4 |
| Example 20 | 64.1 | 61.8 | 30.1 | 47.1 | 11.4 | 60.8 |
| Example 21 | 1.5 | 4 | 4.4 | 9.7 | 5.1 | 3.5 |
| Example 22 | 14.2 | 16 | 10.9 | 26.2 | 8.4 | 29.6 |
| Example 23 | 2.4 | 5.7 | 3.2 | 4.2 | 1.3 | 4.4 |
| Example 24 | 11.1 | 7.1 | 10.2 | 19 | 8.5 | 21.1 |
| Example 25 | 15.5 | 1.4 | 31.7 | 21.9 | 6.9 | 35.1 |
| Example 26 | 68.3 | 66.7 | 38.3 | 49.6 | 12.1 | 67.1 |
| Example 27 | 26.3 | 19.8 | 31.7 | 19.5 | 2.1 | 44.2 |
| Example 28 | 44.9 | 36.1 | 31.1 | 26.7 | 7.3 | 62.3 |
| Example 29 | 54.4 | 50.5 | 32.8 | 40.9 | 11.7 | 67.4 |
| Example 30 | 62.6 | 67.1 | 42.1 | 42.4 | 10.1 | 69.9 |
| Example 31 | 49.5 | 59.9 | 47.2 | 9.2 | 4.5 | 65.3 |
| Example 32 | 54.9 | 54.9 | 45.2 | 24.3 | 26.8 | 63.7 |
| Example 33 | 70 | 66.3 | 36.3 | 37.8 | 40.4 | 72.4 |
| Example 34 | 42.3 | 34.4 | 25.4 | 23.3 | 11.4 | 59.4 |
| Example 35 | 40.5 | 44.7 | 46 | 31.5 | 30.9 | 82.3 |
| Example 36 | 75.5 | 76.2 | 46.9 | 83.4 | 86.1 | 82.4 |
| Example 37 | 75.5 | 70.7 | 55.9 | 78.9 | 78.3 | 84.2 |
| Example 38 | 39.5 | 29.9 | 29.5 | 30.1 | 12.9 | 60 |
| Example 39 | 35.1 | 25.1 | 39.1 | 26.4 | 24.4 | 65.7 |
| Example 40 | 74.2 | 68.1 | 64.1 | 87.6 | 80.7 | 68.7 |
| Example 41 | 69.2 | 65.8 | 55.7 | 38.9 | 42 | 66.6 |
| Example 42 | 36.7 | 28.6 | 45.1 | 41.4 | 35.8 | 60.8 |
| Example 43 | 61 | 56.9 | 45.7 | 19.3 | 29.4 | 69.3 |
| Example 44 | 67.1 | 63.9 | 50.4 | 32.6 | 35.2 | 66.2 |
| Example 45 | 21.3 | 17.5 | 36.2 | 22.2 | 34.2 | 45.3 |
| Example 46 | 73.1 | 70 | 53.2 | 85.9 | 71 | 79.2 |
| Example 47 | 60.4 | 58.1 | 27.7 | 31.7 | 16.6 | 66.2 |
| Example 48 | 71.6 | 72.7 | 53.3 | 86.5 | 74.3 | 79.5 |
| Example 49 | 61.5 | 58.8 | 30.1 | 19.7 | 13.5 | 68.9 |
| Example 50 | 27.5 | 22.7 | 22 | 24.7 | 11.7 | 50.6 |
| Example 51 | 65.6 | 65.2 | 45.7 | 34.5 | 22.4 | 70.5 |
| Example 52 | 74.2 | 68.1 | 64.1 | 87.6 | 80.7 | 68.7 |
| Example 53 | 52.9 | 35.8 | 41.7 | 27.7 | 16.8 | 60.2 |
| Example 54 | 65.4 | 62.4 | 48.3 | 27.7 | 17.2 | 64.7 |
| Example 55 | 36.2 | 26.2 | 23.2 | 18.5 | 15.1 | 56.7 |
| Example 56 | 9.9 | 10.5 | 8.5 | 9.2 | 3.9 | 27.9 |
| Example 57 | 12.5 | 14.6 | 12.8 | 14.4 | 9 | 40.4 |
| Example 58 | 27.7 | 18.9 | 20.3 | 13.5 | 29 | 46.7 |
| Example 59 | 5 | 8 | 10.6 | 20.6 | 22 | 13.4 |
| Example 60 | 53.6 | 52.5 | 30.8 | 22.8 | 19.2 | 65.1 |
| Example 61 | 9.8 | 9.2 | 6.5 | 16.1 | 28 | 12.7 |
| Example 62 | 7.8 | 8.1 | 4.9 | 7.6 | 5.7 | 5 |
| Example 63 | 11.9 | 9.4 | 25.6 | 12.6 | 24.8 | 23.8 |
| Example 64 | 45.9 | 48.5 | 39.6 | 15.5 | 16.6 | 59.4 |
| Example 65 | 65.8 | 62.2 | 42.7 | 23.3 | 16.8 | 66.1 |
| Example 66 | 25.1 | 16.9 | 20.3 | 17.3 | 8.8 | 46.1 |
| Example 67 | 45.9 | 32.1 | 27.6 | 29.2 | 9.4 | 61.1 |
| Example 68 | 5.4 | 5.6 | 8.4 | 5.2 | 30.1 | 9.4 |

IC$_{50}$ values of the compounds of Examples 36/37/40/47/49 against breast cancer cell strains BT474 and BT/Lap$^R$1.0 were measured as follows:

TABLE 4

IC$_{50}$ values of the compounds of Examples against BT474 and BT/Lap$^R$1.0

| ID | BT474 (μM) | BT/Lap$^R$1.0 (μM) |
|---|---|---|
| Example 36 | 1.41 | 1.47 |
| Example 37 | 1.04 | 0.94 |
| Example 40 | 1.62 | 1.68 |
| Example 47 | 1.99 | 1.70 |
| Example 49 | 0.78 | 0.70 |

EXAMPLE 107

Mice pharmacokinetic evaluation of the compound of Example 36 according to the method described below Test Materials 1. Drugs and Reagents The compound of Example 36 (hereinafter referred to as Mol), provided by Laboratory of Pharmaceutical Chemistry, Institute of Pharmacology and Toxicology, Academy of Military Medical Sciences; loratadine (internal standard), provided by Peking University Health Science Center; acetonitrile (chromatographic pure), manufactured by Fisher Co., USA; ammonium acetate (analytical pure), purchased from Sinopharm Chemical Reagent Co., Ltd.; water: Wahaha deionized water.

2. Instrument

Liquid chromatography—mass spectrometry: API 3000 tandem mass spectrometer, provided by AB SciexCo., USA (equipped with Turbo Ionspray ionization source and Analyst 1.4 data processing system); Agilent 1100 quaternary gradient pump and autosampler, provided by Agilent Co., USA.

One over ten-thousand electronic analytical balance (Sartorius Co., Germany); QB-600 vortex mixer (Haimen Kylin-Bell Lab Instruments Co., Ltd.); Thermostatic heater (Beijing Tongda Technology Co., Ltd.); LG10-2.4A low-speed centrifuge (Beijing Medical Centrifuge Factory); WYK-45D air compressor (Tianjin Dyne Instrument Factory).

3. Experimental Animals

ICR mice, SPS grade, male, weighed 22±2 mg, license number SCXK (Beijing) 2012-0001, purchased from Beijing Vital River Laboratory Animal Technology Co. Ltd.

Experimental Conditions

1. LC-MS/MS Conditions

Chromatographic conditions: Analytical column: Capcell Pak MG, 5 μm particle size, 50×2.0 mm I.D. (Shiseido Co.), connected with $C_{18}$ guard column, 4×3.0 mm I.D. (PhenomenexCo., USA), column temperature 25° C., mobile phase: acetonitrile −2 mM ammonium acetate (65:35, v/v), flow rate 0.3 ml/min, internal standard: loratadine.

MS conditions: Electrospray ionization source (Turbo Ionspray source), positive ion mode detection; spray voltage 4500 V; source temperature 400° C.; nebulizer gas (NEB) 8; curtain gas (CUR) 10; collision gas (CAD) 4; scanning mode: multiple reaction monitoring (MRM), ion reactions for quantitative analysis: m/z 354.4→m/z 154.1 (Mol, CE 43 V) and m/z 383→m/z 337 (internal standard loratadine, CE 32 V), scanning time 150 msec.

2. Treatmnet of Sample
2.1 Treatmnet of Plasma Sample

To 50 μl of plasma, were added 10 μl of internal standard solution (125 ng/ml aqueous solution of loratadine), and 500 μl of n-hexane-dichloromethane-isopropanol (100:50:5, v/v/v); they were uniformly mixed, followed by vortexing for 3 min, and centrifuging for 10 min (3000 rpm); the supernatant was taken and blow dried with air streamat 40° C.; the residue was dissolved with 150 μl 170% acetonitrile, and subjected to LC-MS/MS analysis.

2.2 Treatment of In Vitro Experimental Sample

In ice bath, to 20 μl (200 ng/mL) of Mol standard solution, were added 20 μl of 20 mM NADPH, and 110 μl of PBS ($KH_2PO_4$—$K_2HPO_4$ buffer at pH 7.4), followed by incubation in water bath of 37° C. for 3 min; then, 50 μl of 2 mg/ml liver microsomes were added, and uniformly mixed, followed by incubation in water bath of 37° C. for different times (0 h, 0.5 h, 1 h); thereafter 200 μl of 6.2 ng/ml loratadine solution in acetonitrile was added to terminate the reaction, followed by vortexing for 1 min; the reaction mixture was transferred to a 1.5 ml centrifuge tube, placed in a 4° C. refrigerator for 30 min, and centrifuged for 10 min (10000 rpm); 50 μl of the supernatant and 50 μl of water were uniformly mixed, and 10 μl of the mixed solution was taken to carry out LC/MS/MS analysis.

3. Pharmacokinetics

30 ICR male mice were randomly divided into six groups, five mices each group, including Mol 10 mg/kg oral group and 1.0 mg/kg tail intravenous injection group. For oral group, before administration, the animals were fasted for 12 h, with free access to water; 0.08, 0.25, 0.5, 1, 2, 4, 6, 8, 12 and 24 h after intragastrical administration, 0.1 ml of orbital venous sinus blood was taken, placed in anticoagulation tube containing heparin sodium, and subjected to 3000 g centrifugation for 15 min; and then, the plasma was taken and stored in a −20° C. refrigerator. For intravenous injection group, the animals were free access to water and food; 0.03, 0.08, 0.33, 0.5, 1, 2, 4, 6, 8 and 12 h after administration, blood sample was taken, and treated in the same way as above described to obtain the plasma.

4. Data Processing and Analysis

Pharmacokinetic parameters were calculated using non-compartment model of Winnonlin® software (Version 5.2.1, USA). $C_{max}$ is the measured maximum plasma concentration, $T_{max}$ is time to peak plasma concentration after oral administration, $t_{1/2}$ is drug terminal elimination halflife, MRT is average residence time of drug in vivo, the area $AUC_{0-t}$ under plasma concentration—time curve is calculated by trapezoidal method.

Bioavailability is calculated as follows:

$$F(\%) = \frac{AUC_{(po)} \times D_{(iv)}}{AUC_{(iv)} \times D_{(po)}} \times 100\%$$

AUC: Area (h*ng/ml) under the curve; D: dose (mg/kg)

Results and Evaluation

1. Selectivity of Method

Blank plasma, standard addition plasma and plasma sample of mice after administration were treated according to Item "3.2.1", and subjected to LC-MS/MS analysis, to obtain MRM chromatograms. By comparing the chromatograms, it could be seen that endogenous substances in mice plasma did not interfere with the measurement of analyte and internal standard. The chromatographic retention times ($t_R$) of Mol and loratadine were 1.4 min and 1.8 min respectively.

2. Standard Curve and Lower Limit of Quantitation

Using analyte concentration as abscissa, and ratio of peak areas of the analyte and internal standard as ordinate, regression operation was performed using weighted (W=1/$X^2$) least square method, to obtain a linear regression equation of Mol. When Mol was 0.4-400 ng/ml ($r^2$>0.995), the concentration was in a good linear relationship with the peak area. The lower limits of quantification were all 0.4 ng/ml.

3. Intraday Precision and Accuracy of the Method

QC samples containing Mol at low, medium and high concentrations (1.00, 20.0 and 400 ng/ml) were formulated using mice blank plasma with standard addition, and 6 sample analyses were conducted to each concentration within one day, to obtain intraday precision and accuracy of the method (Table 5). The results showed that the precision and accuracy of the method both met the requirements of quantitative analysis of biological samples.

TABLE 5

Precision and Accuracy of Mol(n = 6)

| Concentration (ng/mL) | | RSD (%) | Relative deviation |
|---|---|---|---|
| Added amount | Measured amount | Intraday precision | (%) |
| 1.00 | 0.97 | 9.18 | −3.11 |
| 20.0 | 19.0 | 6.82 | −5.01 |
| 400 | 378 | 8.19 | −5.41 |

4. Recovery and Matrix Effect

Mice plasma QC samples having medium concentration were formulated, and subjected to 3 sample analyses; the peak area of the sample was compared with that of standard solution sample having the same concentration to obtain recovery. The data were shown in Table 2.

At medium concentration level, the matrix effect of Mol in mice plasma samples was studied using standard addition method after extraction of blank plasma. The experimental results showed that the matrix effect of Mol in mice plasma was between 85% and 115%, and plasma had no significant effect on the measurement of Mol. The data were shown in Table 6.

TABLE 6

Recovery and matrix effect of Mol

| | Drug | Mean ± SD (%) | RSD (%) | RE (%) |
|---|---|---|---|---|
| Recovery | Mol | 73.8 ± 8.8 | 12 | — |
| (n = 4) | Internal standard | 71.4 ± 6.1 | 8.6 | — |
| Matrix effect | Mol | 90.3 ± 3.7 | 4.1 | −9.7 |
| (n = 5) | Internal standard | 96.3 ± 5.6 | 5.8 | −3.7 |

5. Plasma Pharmacokinetics

Figure 4:
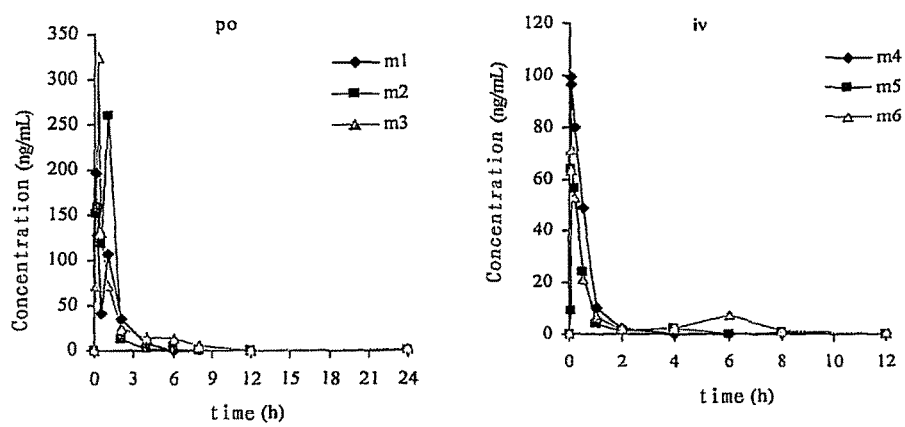
FIG. 4: Plasma concentration—time curve of the active compound after administration to mice of the compound of Example 36.
Figure 5:
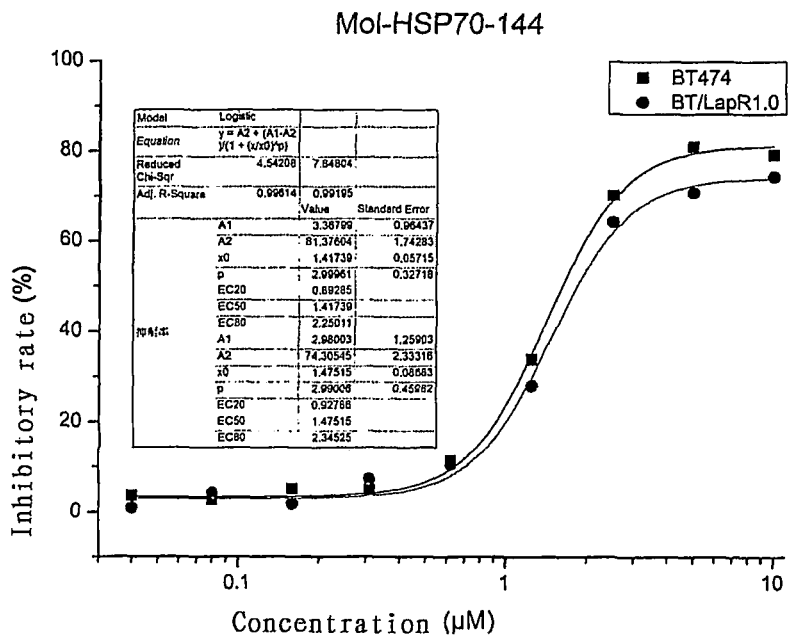
FIG. 5: IC$_{50}$ value of the compound of Example 36.
Figure 6:
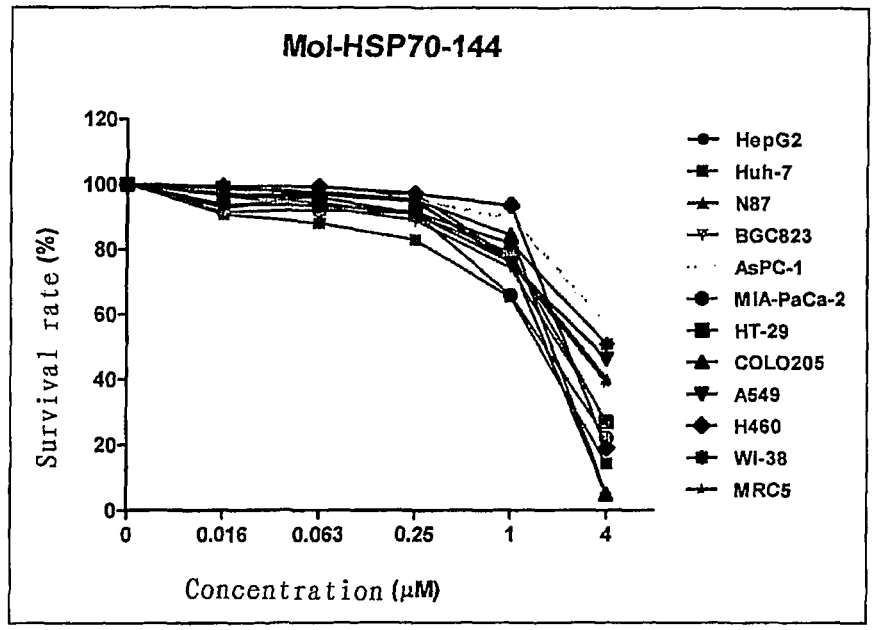
FIG. 6: Survival rate comparison chart of 12 types of cells after administration of the compound of Example 36.
Figure 7:
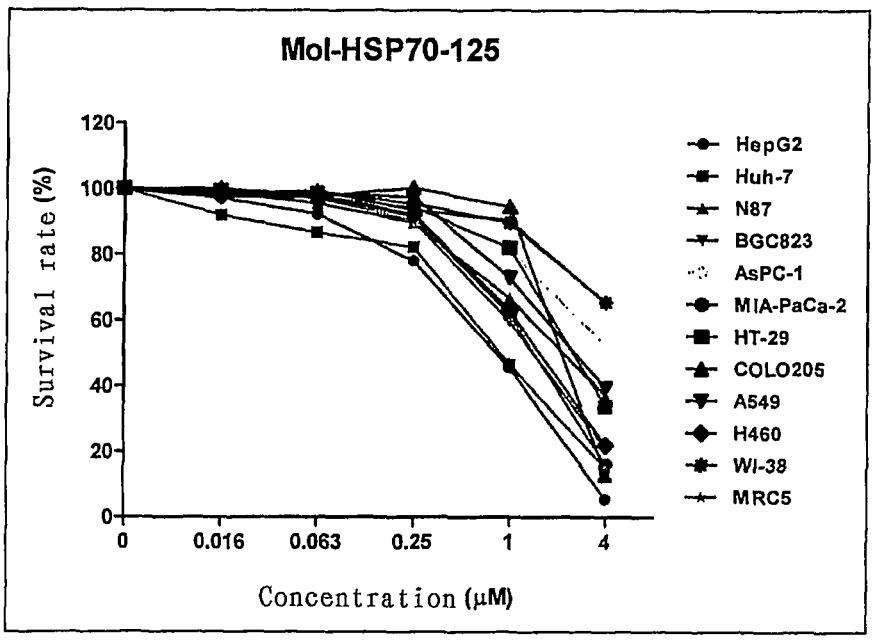
FIG. 7: Survival rate comparison chart of 12 types of cells after administration of the compound of Example 37.
Figure 8:
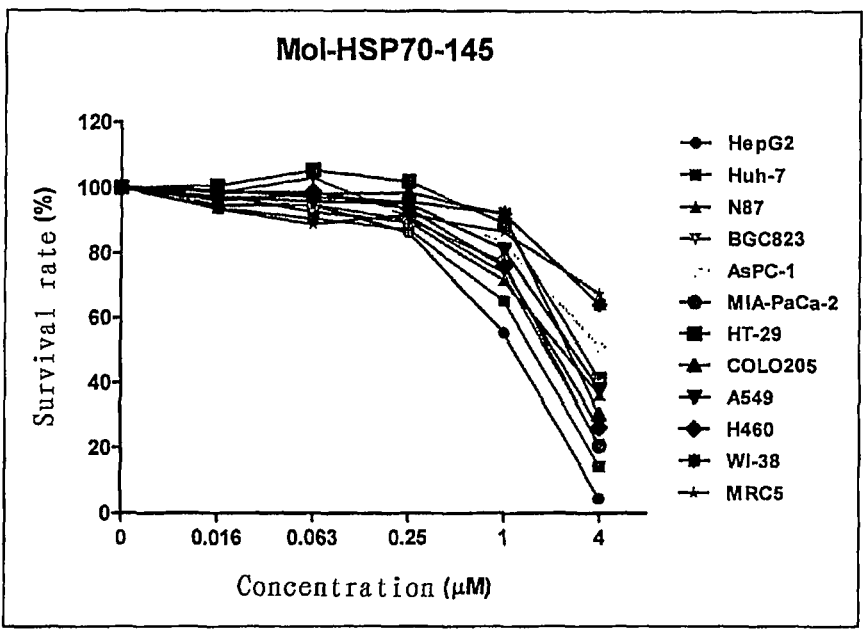
FIG. 8: Survival rate comparison chart of 12 types of cells after administration of the compound of Example 40.
Figure 9:
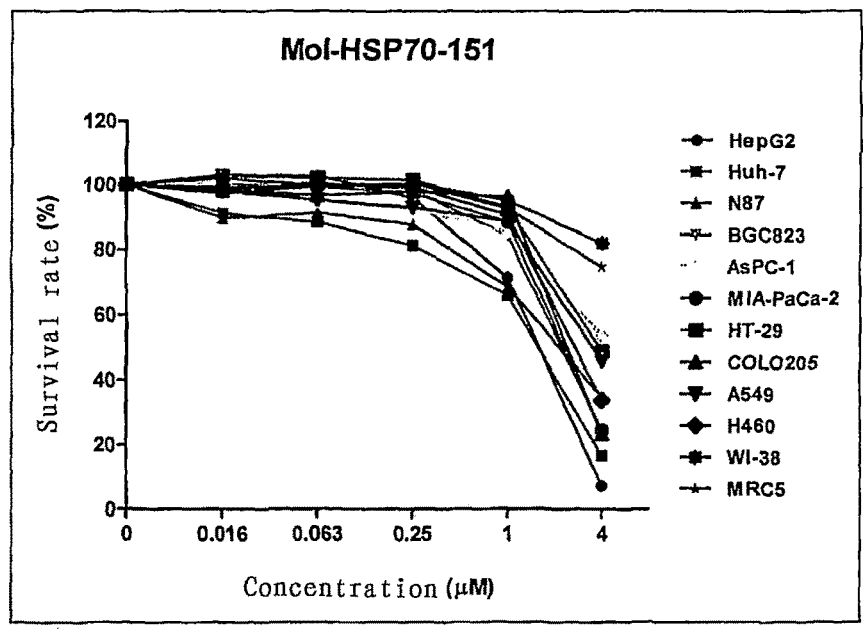
FIG. 9: Survival rate comparison chart of 12 types of cells after administration of the compound of Example 47.
Figure 10:
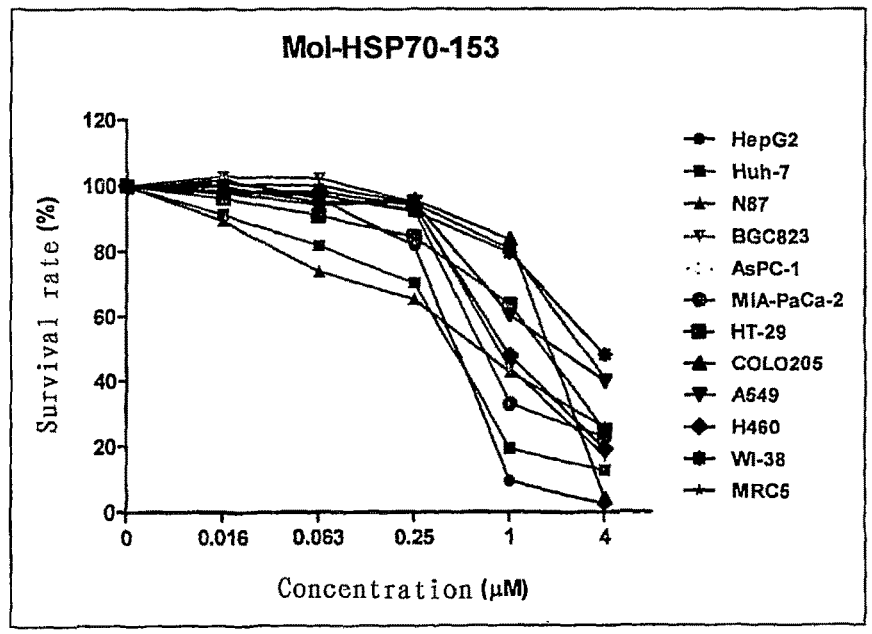
FIG. 10: Survival rate comparison chart of 12 types of cells after administration of the compound of Example 49.

In this test, intragastrical, intravenous administration of a certain dose of Mol to mice was studied. The plasma concentration results of active compound were shown in Table 7, and the plasma concentration—time curve was shown in FIG. 4. The measured data were analyzed using Winnonlin pharmacokinetic program, and the obtained main pharmacokinetic parameters were shown in Table 8.

TABLE 7

Plasma concentration of active compound after oral administration of 10 mg/kg Mol to mice

| Time (h) | Concentration(ng/mL) | | | | |
|---|---|---|---|---|---|
| | 1 | 2 | 3 | Mean | SD |
| 0.08 | 196.99 | 152.22 | 72.70 | 140.64 | 62.95 |
| 0.25 | 126.87 | 158.18 | 323.37 | 202.81 | 105.58 |
| 0.50 | 41.24 | 119.50 | 131.86 | 97.53 | 49.14 |
| 1.0 | 107.54 | 260.48 | 71.98 | 146.67 | 100.16 |
| 2.0 | 33.99 | 12.86 | 23.69 | 23.51 | 10.57 |
| 4.0 | 7.47 | 1.17 | 14.60 | 7.75 | 6.72 |
| 6.0 | ND | 1.28 | 13.43 | 7.36 | 8.59 |
| 8.0 | ND | 0.54 | 4.88 | 2.71 | 3.07 |
| 12.0 | 0.50 | ND | ND | 0.50 | —* |
| 24.0 | ND | ND | 1.32 | 1.32 | —* |

Plasma concentration of active compound after intravenous Administration of 1.0 mg/kg Mol to mice

| Time (h) | Concentration(ng/mL) | | | | |
|---|---|---|---|---|---|
| | 4 | 5 | 6 | Mean | SD |
| 0.03 | 99.34 | 9.23 | 71.35 | 59.97 | 46.12 |
| 0.08 | 96.58 | 63.90 | 63.03 | 74.50 | 19.12 |
| 0.17 | 79.59 | 56.30 | 52.58 | 62.82 | 14.64 |
| 0.5 | 48.72 | 24.29 | 21.45 | 31.48 | 14.99 |
| 1.0 | 10.10 | 3.94 | 7.02 | 7.02 | 3.08 |
| 2.0 | 2.35 | 0.95 | 1.99 | 1.77 | 0.73 |
| 4.0 | ND | 2.30 | 2.23 | 2.26 | 0.05 |
| 6.0 | ND | ND | 7.53 | 7.53 | —* |
| 8.0 | ND | 0.70 | 0.98 | 0.84 | 0.20 |
| 12.0 | ND | ND | ND | — | —* |

ND: lower than limit of quantitation;
*a group of measured values, no SD value

TABLE 8

Main pharmacokinetic parameters after oral or intravenous administration of Mol to mice (Mean ± SD, n = 3)

| Parameter | Unit | Parameter values | | | | | | | |
|---|---|---|---|---|---|---|---|---|---|
| | | Po | | | | IV | | | |
| | | 1 | 2 | 3 | Mean ± SD | 4 | 5 | 6 | Mean ± SD |
| $T_{max}$ | h | 0.08 | 1.00 | 0.25 | 0.44 ± 0.49 | 0.03 | 0.08 | 0.03 | 0.05 ± 0.03 |
| $C_{max}$ | ng/mL | 196.99 | 260.48 | 323.37 | 260.2 ± 63.19 | 99.34 | 63.90 | 71.35 | 78.1 ± 18.68 |
| Ke | 1/h | 0.40 | 0.77 | 0.13 | 0.43 ± 0.33 | 1.98 | 0.51 | 0.43 | 0.97 ± 0.88 |
| $t_{1/2}$ | h | 1.74 | 0.90 | 5.53 | 2.72 ± 2.47 | 0.35 | 1.37 | 1.62 | 1.11 ± 0.67 |
| $AUC_{0-t}$ | h*ng/L | 214.30 | 317.16 | 294.60 | 275.3 ± 54.06 | 56.42 | 36.43 | 55.97 | 49.60 ± 11.41 |
| $AUC0_{-\infty}$ | h*ng/mL | 215.55 | 317.86 | 305.15 | 279.5 ± 55.76 | 57.60 | 37.81 | 58.27 | 51.23 ± 11.62 |
| $MRT_{0-t}$ | h | 1.26 | 0.93 | 2.56 | 1.58 ± 0.86 | 0.42 | 1.02 | 2.40 | 1.28 ± 1.01 |
| $MRT_{0-\infty}$ | h | 1.34 | 0.95 | 3.57 | 1.95 ± 1.42 | 0.46 | 1.35 | 2.71 | 1.51 ± 1.13 |
| F | % | 43.20 | 63.94 | 59.39 | 55.51 ± 10.90 | — | — | — | — |

As could be seen from the data in Table 8, $C_{max}$ was 260.28±63.19 ng/ml after intragastrical administration of 10 mg/kg Mol to mice, the vivo absorption and elimination after intragastrical administration to mice both were quite fast, the peak time $T_{max}$ was 0.44±0.49 h, the half-life $T_{1/2}$ was 2.72±2.47 h. The absolute bioavailability was 55.51±10.90%.

EXAMPLE 108

Acute toxicity experiment with single intragastric administration to mice of the compound of Example 36 according to the following method Materials and Method 1. Animals Species: mouse Strain: KM Gender and quantity of animals for intended purchase: female: 40; male: 40.

Gender and quantity of animals for intended use: female: 35; male: 35.

Week age of animals: at the beginning of administration, about 5 weeks old.

Animal weight: at the beginning of administration, about 22 grams.

Animal source: Sibeifu (Beijing) Laboratory Animal Technology Co. Ltd.

Laboratory animal production license number: SCXK (Beijing) 2011-0004

Animals Level: SPF

2. Preparation of Analyte (1) Preparation of 0.5% carboxymethylcellulose sodium (0.5% CMC-Na): 0.5 g of carboxymethylcellulose sodium was weighed, and put into a conical flask, to which was added 100 ml distilled water. The resulting solution was made uniform by a magnetic stirrer, and stored in a brown reagent bottle at room temperature.

(2) Preparation of test sample: a suitable amount of sample was weighed, and suspended in 0.5% CMC-Na, followed by vortex vibration till uniform. The resulting suspension was fully vibrated before administration. The concrete formulation was shown in Table 9.

TABLE 9

Formulation of the compound of Example 36

| Dose (mg/kg) | Weighed amount of test sample (mg) | 0.5% CMC-Na (ml) | Concentration of test sample (mg/ml) |
|---|---|---|---|
| 1555 | 466.5 | 3 | 155.5 |
| 1296 | 388.8 | 3 | 129.6 |
| 1080 | 324.0 | 3 | 108.0 |
| 900 | 270.0 | 3 | 90.0 |
| 750 | 225.0 | 3 | 75.0 |
| 625 | 187.5 | 3 | 62.5 |
| 520 | 156.0 | 3 | 52.0 |

3. Administration Volume 0.1 ml/10 g

4. Administration Route

Intragastrical Administration

5. Grouping of Animals

According to the results of pre-experiment, experiment was conducted using Fixed-dose procedure. 70 mice were randomly divided into 7 groups, 10 mice each group, male and female in half. The administration doses were respectively: 1555, 1296, 1080, 900, 750, 625 and 520 mg/kg, and observation of the animals after administration continued for 14 days. The concrete grouping was shown in Table 10.

TABLE 10

Grouping of animals involved in acute toxicity experiment with the compound of Example 36

| Group | Administration dose (mg/kg) | Quantity of animals Male | Female |
|---|---|---|---|
| 1 | 1555 | 5 | 5 |
| 2 | 1296 | 5 | 5 |
| 3 | 1080 | 5 | 5 |
| 4 | 900 | 5 | 5 |
| 5 | 750 | 5 | 5 |
| 6 | 625 | 5 | 5 |
| 7 | 520 | 5 | 5 |

6. Clinical Observation

Observation was conducted once 5 min, 10 min, 20 min, 30 min, 1 h, 2 h, 4 h, 6 h, 8 h, 12 h, 18 h, 1 d, 2 d, 3 d, 7 d and 14 d respectively after administration, to record the animal death and toxic response.

7. Statistical Analysis $LD_{50}$ was calculated by statistical analysis using SAS software.

Results

1. Clinical Observation

First animal death appeared in the 1555 mg/kg dose group, which appeared 5 min after administration, subsequently, animal death gradually appeared in other dose groups, but no animal death was observed after 1 d, till the end of 14 d experiment. The animals in the 520 mg/kg dose group all survived. The animal death was shown in Table 3.

Clinical manifestations of animal poisoning included muscle tremors, convulsions, eye closed, curled up into a ball, erected hair, reduced activity, loss of appetite.

TABLE 11

Record of animal death

| Group | Administration dose (mg/kg) | Quantity of animals Male (survival/death) | Female (survival/death) |
|---|---|---|---|
| 1 | 1555 | 0/5 | 0/5 |
| 2 | 1296 | 1/4 | 0/5 |
| 3 | 1080 | 0/5 | 2/3 |
| 4 | 900 | 3/2 | 2/3 |
| 5 | 750 | 4/1 | 2/3 |
| 6 | 625 | 4/1 | 5/0 |
| 7 | 520 | 5/0 | 5/0 |

2. Calculation of $LD_{50}$ Using Bliss Method

As calculated using SAS software package, the $LD_{50}$ and 95% confidence limit were 869.0 (776.5-969.4) mg/kg.

3. Pathological Examination Results

No obvious abnormality was found when making gross anatomical examination to the animals that were dead during the experiment and were killed at the end of the experiment. Thus, no further histopathological examination was conducted.

Conclusion

The half-lethal dose and 95% confidence limit of intragastrical administration of the compound of Example 36 to mice were 869.0 (776.5-969.4) mg/kg.

EXAMPLE 109

Extended Test of the Compounds of Examples 36/37/40/47/49 Against Tumor Cell Lines 1. Test Materials The compounds of Examples 36/37/40/47/49 were used to carry out extended test against tumor cell lines, wherein 12 kinds of cells were selected, including liver cancer cells, gastric cancer cells, pancreatic cancer cells, colorectal cancer cells, lung cancer cells and normal cells, which were shown in Table 12:

TABLE 12

Cells selected for extended test against tumor cell lines

| Liver cancer | HepG2, Huh-7 |
| Gastric cancer | N87, BGC823 |
| Pancreatic cancer | AsPC-1, MIA-PaCa-2 |
| Colorectal cancer | COLO205, HT-29 |
| Lung cancer | A549, H460 |
| Normal cells | WI-38 (human embryonic lung fibroblast), MRC5 (lung epithelial fibroblast) |

ATPlite kit: CellTiter-Glo Substrate, Promega, Part: G755B, Lot: 32513501, EXP: 2014-05

2. Experimental Procedures

1) Cells plating

A 100 mm culture dish with overgrown adherent cells was digested with 1 ml 0.25% trypsin (GIBCO) at 37° C. for 5 min, and the reaction was terminated with 2 ml culture medium (containing 10% FBS, GIBCO). The cells were scattered and collected, after counting, diluted to $1 \times 10^5$ cells/ml, and seeded into a 96-well plate at 50 μl/well, 5000 cells/well, excluding the peripheral circle of wells in which no cell was added, but PBS was added, 54 wells in total, and then incubated at 37° C. for 24 hours for adhering.

2) Addition of compound

The test sample was diluted to final concentration of 4, 1, 0.25, 0.063, 0.016 μM, culture medium was filled in control well, 3 parellel wells were set for each concentration, 50 μl each well, followed by incubation at 37° C. for 72 hours.

3) Test after incubation at 37° C. for 72 hours: 50 μL of ATPlite kitsubstrate solution was added in each well, and vibrated for 3 min, followed by placing aside in darkness for 10 min, and then supernatant 100 μl/well was taken and placed on a luminescence test plate; the luminescence test plate that has been fully incubated was placed in a luminescence test instrument, to read luminescence value.

3. Data Processing

Cell survival rate (%)=Experimental group RLU/control group RLU×100%. The experimental data were subjected to data analysis and processing by utilizing GraphPad software.

4. Experimental Results

The compound of Example 36 exhibited certain inhibition and cytotoxicity to either tumor cells or normal cells, without significant difference. The results were shown in Table 13:

TABLE 13

Survival rates of various kinds of cells under the action of different concentrations of the compound of Example 36

| | cells | 4 | 1 | 0.25 | 0.063 | 0.016 | 0 |
|---|---|---|---|---|---|---|---|
| | | Concentration(μM) | | | | | |
| Liver cancer | HepG2 | 4.5 | 77.1 | 94.7 | 97 | 98.8 | 100 |
| | Huh-7 | 14.3 | 65.4 | 83.0 | 88.2 | 90.9 | 100 |
| Gastric cancer | N87 | 40.3 | 77.1 | 97.2 | 96.7 | 92.9 | 100 |
| | BGC823 | 27.7 | 74.3 | 89.1 | 93.2 | 96.6 | 100 |
| Pancreatic cancer | AsPC-1 | 57.2 | 90.0 | 94.9 | 99.4 | 96.8 | 100 |
| | MIA-PaCa-2 | 22.2 | 66.0 | 91.2 | 92.2 | 91.6 | 100 |
| Colorectal cancer | HT-29 | 27.1 | 79.0 | 90.9 | 94.3 | 97.5 | 100 |
| | COLO205 | 4.9 | 84.5 | 95.3 | 96.9 | 96.7 | 100 |
| Lung cancer | A549 | 46.5 | 75.8 | 95.3 | 97.6 | 98.9 | 100 |
| | H460 | 19.1 | 93.6 | 97.3 | 99.3 | 99.4 | 100 |
| Normal cells | WI-38 | 51.1 | 82.0 | 91.5 | 93.7 | 93.9 | 100 |
| | MRC5 | 39.1 | 76.1 | 91.0 | 96.1 | 96.8 | 100 |

The compound of Example 37 exhibited slightly stronger inhibition to liver cancer than that to other tumor cells, and exhibited cytotoxicity to normal cells lower than inhibition to tumor cells. The results were shown in Table 14:

TABLE 14

Survival rates of various kinds of cells under the action of different concentrations of the compound of Example 37

| | cells | 4 | 1 | 0.25 | 0.063 | 0.016 | 0 |
|---|---|---|---|---|---|---|---|
| | | Concentration (μM) | | | | | |
| Liver cancer | HepG2 | 5.6 | 45.7 | 78.1 | 92.3 | 97.1 | 100 |
| | Huh-7 | 14.9 | 46.7 | 82.3 | 86.7 | 91.9 | 100 |
| Gastric cancer | N87 | 37.1 | 66.8 | 89.7 | 95.6 | 98.9 | 100 |
| | BGC823 | 21 | 59.7 | 90.2 | 97.2 | 97.6 | 100 |
| Pancreatic cancer | AsPC-1 | 52.3 | 81.7 | 94.1 | 99.5 | 98.8 | 100 |
| | MIA-PaCa-2 | 16 | 61.9 | 91.5 | 97.5 | 97.6 | 100 |
| Colorectal cancer | HT-29 | 33.8 | 82.1 | 94.4 | 97.4 | 99.3 | 100 |
| | COLO205 | 12.9 | 94.5 | 100.4 | 97.5 | 100.1 | 100 |
| Lung cancer | A549 | 39.5 | 73 | 97.6 | 98.5 | 99.5 | 100 |
| | H460 | 22 | 63.1 | 92.3 | 97.9 | 97.7 | 100 |
| Normal cells | WI-38 | 65.6 | 89.7 | 95.5 | 99.2 | 98.6 | 100 |
| | MRC5 | 65.3 | 90.4 | 93.5 | 99.5 | 97.3 | 100 |

The compound of Example 40 exhibited slightly stronger inhibition to liver cancer than that to other tumor cells, and exhibited cytotoxicity to normal cells lower than inhibition to tumor cells. The results were shown in Table 15:

TABLE 15

Survival rates of various kinds of cells under the action of different concentrations of the compound of Example 40

| | cells | 4 | 1 | 0.25 | 0.063 | 0.016 | 0 |
|---|---|---|---|---|---|---|---|
| | | Concentration (μM) | | | | | |
| Liver cancer | HepG2 | 4.5 | 55.3 | 86.4 | 94.8 | 94.7 | 100 |
| | Huh-7 | 14.3 | 65.2 | 87.3 | 90.7 | 93.8 | 100 |
| Gastric cancer | N87 | 36.3 | 71.5 | 89.7 | 92.7 | 97.9 | 100 |
| | BGC823 | 21.1 | 73.7 | 91.3 | 103.1 | 98.3 | 100 |
| Pancreatic cancer | AsPC-1 | 51.2 | 83.3 | 93.1 | 96.1 | 97.8 | 100 |
| | MIA-PaCa-2 | 20.6 | 77.3 | 90.2 | 94.8 | 94.6 | 100 |
| Colorectal cancer | HT-29 | 41.2 | 89.2 | 102 | 105.4 | 100.6 | 100 |
| | COLO205 | 30.3 | 91.9 | 98.6 | 98.2 | 96.2 | 100 |
| Lung cancer | A549 | 38 | 81.2 | 95.3 | 95.9 | 97.1 | 100 |
| | H460 | 26.3 | 75.9 | 93.7 | 98.7 | 98.7 | 100 |
| Normal cells | WI-38 | 64.2 | 92.3 | 95.8 | 97.3 | 99.3 | 100 |
| | MRC5 | 67.6 | 86.5 | 91.9 | 88.9 | 93.6 | 100 |

The compound of Example 47 exhibited slightly stronger inhibition to liver cancer than that to other tumor cells, and exhibited cytotoxicity to normal cells lower than inhibition to tumor cells. The results were shown in Table 16:

TABLE 16

Survival rates of various kinds of cells under the action of different concentrations of the compound of Example 47

| | cells | 4 | 1 | 0.25 | 0.063 | 0.016 | 0 |
|---|---|---|---|---|---|---|---|
| | | Concentration(μM) | | | | | |
| Liver cancer | HepG2 | 7.3 | 71.4 | 96 | 102.7 | 103.1 | 100 |
| | Huh-7 | 16.7 | 65.9 | 81.4 | 88.3 | 91.1 | 100 |
| Gastric cancer | N87 | 34.8 | 68.6 | 87.8 | 91.3 | 89.6 | 100 |
| | BGC823 | 24.5 | 84.3 | 98.4 | 100.6 | 99.8 | 100 |
| Pancreatic cancer | AsPC-1 | 53.6 | 85.3 | 92.8 | 94.7 | 100.2 | 100 |
| | MIA-PaCa-2 | 24.5 | 88.5 | 97.4 | 99.3 | 98.5 | 100 |
| Colorectal cancer | HT-29 | 48.8 | 93.1 | 101.6 | 102.1 | 102.8 | 100 |
| | COLO205 | 23.3 | 96.1 | 97.9 | 96.7 | 98.2 | 100 |
| Lung cancer | A549 | 45.9 | 88.7 | 93 | 95.3 | 98.1 | 100 |
| | H460 | 33.8 | 90.6 | 99.3 | 99.8 | 99 | 100 |
| Normal cells | WI-38 | 82.1 | 95.1 | 100.4 | 99.7 | 102.1 | 100 |
| | MRC5 | 74.8 | 92.6 | 100.3 | 99.5 | 97.3 | 100 |

The compound of Example 49 exhibited certain inhibition and cytotoxicity to either tumor cells or normal cells, without significant difference. The results were shown in Table 17:

TABLE 17

Survival rates of various kinds of cells under the action of different concentrations of the compound of Example 49

| | cells | 4 | 1 | 0.25 | 0.063 | 0.016 | 0 |
|---|---|---|---|---|---|---|---|
| | | Concentration(μM) | | | | | |
| Liver cancer | HepG2 | 2.4 | 9.5 | 82.1 | 96.2 | 101.8 | 100 |
| | Huh-7 | 12.8 | 19.4 | 70.5 | 82 | 91.3 | 100 |
| Gastric cancer | N87 | 26 | 42.8 | 65.6 | 74.1 | 89.5 | 100 |
| | BGC823 | 17.3 | 44 | 95.1 | 102.4 | 102.8 | 100 |
| Pancreatic cancer | AsPC-1 | 44.3 | 64.4 | 93.8 | 97.5 | 99.1 | 100 |
| | MIA-PaCa-2 | 22.9 | 33.1 | 92.8 | 97.4 | 97.6 | 100 |
| Colorectal cancer | HT-29 | 25.1 | 63.9 | 84.7 | 91 | 96.3 | 100 |
| | COLO205 | 4.1 | 83.9 | 95.8 | 94.2 | 98.1 | 100 |
| Lung cancer | A549 | 40.1 | 60.5 | 95.2 | 95.1 | 99.9 | 100 |
| | H460 | 19.3 | 47.9 | 94.2 | 98.3 | 98.4 | 100 |
| Normal cells | WI-38 | 48.4 | 79.8 | 92.4 | 97.3 | 98.5 | 100 |
| | MRC5 | 41.1 | 80.8 | 94.8 | 100.1 | 100.6 | 100 |

5. Experimental Conclusion

The compounds of Examples 36/49 exhibited certain inhibition and cytotoxicity to either tumor cells or normal cells, without significant difference. The compounds of Examples 37/40/47 exhibited slightly stronger inhibition to liver cancer than that to other tumor cells, and exhibited cytotoxicity to normal cells lower than inhibition to tumor cells. Among them, the compound of Example 47 had effect superior to that of the compounds of other Examples.

What is claimed is:

1. A compound, or a stereoisomer, pharmaceutically acceptable salt, solvate or N-oxide thereof, wherein the compound is selected from the following:

N-methyl-N-m-chlorobenzyl-N-{1-[(2-ethoxythiazol-5-yl)methyl]piperidin-4-yl}amine,
N-methyl-N-o-cyanobenzyl-N-{1-[(2-ethoxythiazol-5-yl)methyl]piperidin-4-yl}amine,
N-methyl-N-(3,4-dichlorobenzyl)-N-{1-[(2-ethoxythiazol-5-yl)methyl]piperidin-4-yl}amine,
N-methyl-N-(4-cyanobenzyl)-N-{1-[(2-ethoxythiazol-5-yl)methyl]piperidin-4-yl}amine,
N-methyl-N-(2-fluoro-6-chlorobenzyl)-N-{1-[(2-ethoxythiazol-5-yl)methyl]piperidin-4-yl}amine,
N-methyl-N-(2-chlorobenzyl)-N-{1-[(2-ethoxythiazol-5-yl)methyl]piperidin-4-yl}amine,
N-methyl-N-(4-fluorobenzyl)-N-{[1-(2-ethoxythiazol-5-yl)methyl]piperidin-4-yl}amine,
N-methyl-N-(2,4-dichlorobenzyl)-N-{[1-(2-ethoxythiazol-5-yl)methyl]piperidin-4-yl}amine,
N-methyl-N-(2,6-dichlorobenzyl)-N-{[1-(2-ethoxythiazol-5-yl)methyl]piperidin-4-yl}amine,
N-methyl-N-(2,5-dichlorobenzyl)-N-{[1-(2-ethoxythiazol-5-yl)methyl]piperidin-4-yl}amine,
N-(3,4-dichlorobenzyl)-N-{1-[(2-chlorothiazol-5-yl)methyl]piperidin-4-yl}amine,
N-(4-fluorobenzyl)-N-{1-[(2-chlorothiazol-5-yl)methyl]piperidin-4-yl}amine,
N-(3-chlorobenzyl)-N-{1-[(2-chlorothiazol-5-yl)methyl]piperidin-4-yl}amine,
N-methyl-N-(2-cyanobenzyl)-N-{1-[(2-chlorothiazol-5-yl)methyl]piperidin-4-yl}amine,
N-methyl-N-(4-cyanobenzyl)-N-{1-[(2-chlorothiazol-5-yl)methyl]piperidin-4-yl}amine,
N-methyl-N-(4-fluorobenzyl)-N-{1-[(2-chlorothiazol-5-yl)methyl]piperidin-4-yl}amine,
N-methyl-N-(3,4-dichlorobenzyl)-N-{1-[(2-chlorothiazol-5-yl)methyl]piperidin-4-yl}amine,
N-methyl-N-(3-chlorobenzyl)-N-{1-[(2-chlorothiazol-5-yl)methyl]piperidin-4-yl}amine,
N-methyl-N-(2-fluoro-6-chlorobenzyl)-N-{[1-(2-chlorothiazol-5-yl)methyl]piperidin-4-yl}amine,
N-methyl-N-(2,4-dichlorobenzyl)-N-{[1-(2-chlorothiazol-5-yl)methyl]piperidin-4-yl}amine,
N-methyl-N-(2-methylbenzyl)-N-{[1-(2-chlorothiazol-5-yl)methyl]piperidin-4-yl}amine,
N-methyl-N-(4-methylbenzyl)-N-{[1-(2-chlorothiazol-5-yl)methyl]piperidin-4-yl}amine,
N-methyl-N-(3-fluorobenzyl)-N-{[1-(2-chlorothiazol-5-yl)methyl]piperidin-4-yl}amine,
N-methyl-N-(2,5-dichlorobenzyl)-N-{[1-(2-chlorothiazol-5-yl)methyl]piperidin-4-yl}amine,
N-methyl-N-(2-methylbenzyl)-N-{[1-(2-methylthiothiazol-5-yl)methyl]piperidin-4-yl}amine,
N-methyl-N-(4-methylbenzyl)-N-{[1-(2-methylthiothiazol-5-yl)methyl]piperidin-4-yl}amine,
N-methyl-N-(3-fluorobenzyl)-N-{[1-(2-methylthiothiazol-5-yl)methyl]piperidin-4-yl}amine,
N-methyl-N-(3-chlorobenzyl)-N-{1-[(2-methylthiothiazol-5-yl)methyl]piperidin-4-yl}amine,
N-methyl-N-(4-fluorobenzyl)-N-{1-[(2-methylthiothiazol-5-yl)methyl]piperidin-4-yl}amine,
N-methyl-N-(3,4-dichlorobenzyl)-N-{1-[(2-methylthiothiazol-5-yl)methyl]piperidin-4-yl}amine,
N-methyl-N-(2-fluoro-6-chlorobenzyl)-N-{1-[(2-methylthiothiazol-5-yl)methyl]piperidin-4-yl}amine,
N-methyl-N-(2,5-dichlorobenzyl)-N-{1-[(2-methylthiothiazol-5-yl)methyl]piperidin-4-yl}amine,
N-methyl-N-(2,4-dichlorobenzyl)-N-{1-[(2-methylthiothiazol-5-yl)methyl]piperidin-4-yl}amine,
N-methyl-N-(2,5-dichlorobenzyl)-N-{1-[(2-methylthiothiazol-5-yl)methyl]piperidin-4-yl}amine,
N-methyl-N-(4-fluorobenzyl)-N-[1-(2-methylthiopyrimidin-4-yl)piperidin-4-yl]amine,
N-methyl-N-(4-cyanobenzyl)-N-[1-(2-methylthiopyrimidin-4-yl)piperidin-4-yl]amine,
N-methyl-N-(2-fluoro-6-chlorobenzyl)-N-[1-(2-methylthiopyrimidin-4-yl)piperidin-4-yl]amine,
N-methyl-N-(3,4-dichlorobenzyl)-N-[1-(2-methylthiopyrimidin-4-yl)piperidin-4-yl]amine,
N-methyl-N-(3-chlorobenzyl)-N-[1-(2-methylthiopyrimidin-4-yl)piperidin-4-yl]amine,
N-methyl-N-(2,4-dichlorobenzyl)-N-[1-(2-methylthiopyrimidin-4-yl)piperidin-4-yl]amine,
N-methyl-N-(2-cyanobenzyl)-N-[1-(2-methylthiopyrimidin-4-yl)piperidin-4-yl]amine,
N-methyl-N-(4-methylbenzyl)-N-[1-(2-methylthiopyrimidin-4-yl)piperidin-4-yl]amine,
N-methyl-N-(2-chlorobenzyl)-N-[1-(2-methoxypyrimidin-4-yl)piperidin-4-yl]amine,
N-methyl-N-(2,4-dichlorobenzyl)-N-[1-(2-methylthiopyrimidin-4-yl)piperidin-4-yl]amine,
N-methyl-N-(3-fluorobenzyl)-N-[1-(2-methylthiopyrimidin-4-yl)piperidin-4-yl]amine,
N-methyl-N-(2-chlorobenzyl)-N-[1-(2-methylthiopyrimidin-4-yl)piperidin-4-yl]amine,
N-methyl-N-(4-cyanobenzyl)-N-[1-(2-methoxypyrimidin-4-yl)piperidin-4-yl]amine,
N-methyl-N-(2,6-dichlorobenzyl)-N-[1-(2-methylthiopyrimidin-4-yl)piperidin-4-yl]amine,
N-methyl-N-(2-cyanobenzyl)-N-[1-(2-methoxypyrimidin-4-yl)piperidin-4-yl]amine,
N-methyl-N-(4-methylbenzyl)-N-[1-(2-methoxypyrimidin-4-yl)piperidin-4-yl]amine,
N-methyl-N-(2,5-dichlorobenzyl)-N-[1-(2-methoxypyrimidin-4-yl)piperidin-4-yl]amine,
N-methyl-N-(3,4-dichlorobenzyl)-N-[1-(2-methoxypyrimidin-4-yl)piperidin-4-yl]amine,
N-methyl-N-(2-fluoro-6-chlorobenzyl)-N-[1-(2-methoxypyrimidin-4-yl)piperidin-4-yl]amine,
N-methyl-N-(3-chlorobenzyl)-N-[1-(2-methoxypyrimidin-4-yl)piperidin-4-yl]amine,
N-methyl-N-(3-fluorobenzyl)-N-[1-(2-methoxypyrimidin-4-yl)piperidin-4-yl]amine,
N-methyl-N-(4-fluorobenzyl)-N-[1-(2-methoxypyrimidin-4-yl)piperidin-4-yl]amine,
N-methyl-N-(2-chlorobenzyl)-N-[1-(6-methoxypyrimidin-4-yl)piperidin-4-yl]amine,
N-methyl-N-(4-methylbenzyl)-N-[1-(6-methoxypyrimidin-4-yl)piperidin-4-yl]amine,
N-methyl-N-(2,6-dichlorobenzyl)-N-[1-(6-methoxypyrimidin-4-yl)piperidin-4-yl]amine,
N-methyl-N-(3,4-dichlorobenzyl)-N-[1-(6-methoxypyrimidin-4-yl)piperidin-4-yl]amine,
N-methyl-N-(4-fluorobenzyl)-N-[1-(6-methoxypyrimidin-4-yl)piperidin-4-yl]amine,
N-methyl-N-(3-chlorobenzyl)-N-[1-(6-methoxypyrimidin-4-yl)piperidin-4-yl]amine,
N-methyl-N-(2-fluoro-6-chlorobenzyl)-N-[1-(6-methoxypyrimidin-4-yl)piperidin-4-yl]amine, N-methyl-N-(2-cyanobenzyl)-N-[1-(6-methoxypyrimidin-4-yl)piperidin-4-yl]amine,
N-methyl-N-(p-cyanobenzyl)-N-[1-(6-methoxypyrimidin-4-yl)piperidin-4-yl]amine,
N-methyl-N-(2,5-dichlorobenzyl)-N-[1-(6-methoxypyrimidin-4-yl)piperidin-4-yl]amine,
N-methyl-N-(3-fluorobenzyl)-N-[1-(6-methoxypyrimidin-4-yl)piperidin-4-yl]amine,
N-methyl-N-(4-cyanobenzyl)-N-[1-(2-methylthiopyrimidin-4-yl)piperidin-4-yl]amine hydrochloride,
N-methyl-N-(4-cyanobenzyl)-N-[1-(2-methylthiopyrimidin-4-yl)piperidin-4-yl]amine methanesulfonate,
N-methyl-N-(3-cyanobenzyl)-N-[1-(4-methoxypyrimidin-2-yl)piperidin-4-yl]amine,
N-methyl-N-(3-cyanobenzyl)-N-[1-(2-methylthiopyrimidin-4-yl)piperidin-4-yl]amine,
N-methyl-N-(3-cyanobenzyl)-N-[1-(2-chloropyrimidin-4-yl)piperidin-4-yl]amine,
N-methyl-N-(3-cyanobenzyl)-N-[1-(4-methylthiopyrimidin-2-yl)piperidin-4-yl]amine,
N-methyl-N-(3-cyanobenzyl)-N-[1-(4-chloropyrimidin-2-yl)piperidin-4-yl]amine,
N-methyl-N-(4-cyanobenzyl)-N-[1-(4-chloropyrimidin-2-yl)piperidin-4-yl]amine,
N-(4-cyanobenzyl)-N-[1-(2-methoxypyrimidin-4-yl)piperidin-4-yl]amine,
N-methyl-N-(4-cyanobenzyl)-N-[1-(2-ethoxypyrimidin-4-yl)piperidin-4-yl]amine,
N-methyl-N-(3-cyanobenzyl)-N-[1-(2-ethoxypyrimidin-4-yl)piperidin-4-yl]amine,
N-methyl-N-(2-fluorobenzyl)-N-[1-(2-ethoxypyrimidin-4-yl)piperidin-4-yl]amine,
N-methyl-N-(2,6-difluorobenzyl)-N-[1-(2-methoxypyrimidin-4-yl)piperidin-4-yl]amine,
N-methyl-N-(2-fluorobenzyl)-N-[1-(2-methoxypyrimidin-4-yl)piperidin-4-yl]amine,
N-methyl-N-(4-chlorobenzyl)-N-[1-(2-methoxypyrimidin-4-yl)piperidin-4-yl]amine,
N-methyl-N-(4-chlorobenzyl)-N-[1-(2-methylthiopyrimidin-4-yl)piperidin-4-yl]amine,
N-methyl-N-(2-fluorobenzyl)-N-[1-(2-methylthiopyrimidin-4-yl)piperidin-4-yl]amine,
N-methyl-N-(2,6-difluorobenzyl)-N-[1-(2-methylthiopyrimidin-4-yl)piperidin-4-yl]amine,
N-methyl-N-(3,5-dimethoxybenzyl)-N-[1-(2-ethoxypyrimidin-4-yl)piperidin-4-yl]amine,
N-methyl-N-(2-nitrobenzyl)-N-[1-(2-ethoxypyrimidin-4-yl)piperidin-4-yl]amine,
N-methyl-N-(2-nitrobenzyl)-N-[1-(2-methylthiopyrimidin-4-yl)piperidin-4-yl]amine,
N-methyl-N-(2-nitrobenzyl)-N-[1-(2-methoxypyrimidin-4-yl)piperidin-4-yl]amine,
N-methyl-N-(3,5-dimethoxybenzyl)-N-[1-(2-methoxypyrimidin-4-yl)piperidin-4-yl]amine,
N-(2,6-dichlorobenzyl)-N-[1-(2-methoxypyrimidin-4-yl)piperidin-4-yl]amine,
N-(3,5-dimethoxybenzyl)-N-[1-(2-methoxypyrimidin-4-yl)piperidin-4-yl]amine,
N-(2-cyanobenzyl)-N-[1-(2-methoxypyrimidin-4-yl)piperidin-4-yl]amine,
N-(2-nitrobenzyl)-N-[1-(2-methoxypyrimidin-4-yl)piperidin-4-yl]amine,
N-(4-cyanobenzyl)-N-[1-(2-ethoxypyrimidin-4-yl)piperidin-4-yl]amine,
N-(2,6-dichlorobenzyl)-N-[1-(2-ethoxypyrimidin-4-yl)piperidin-4-yl]amine,
N-methyl-N-(4-nitrobenzyl)-N-[1-(2-ethoxypyrimidin-4-yl)piperidin-4-yl]amine,
N-(2,6-difluorobenzyl)-N-[1-(2-ethoxypyrimidin-4-yl)piperidin-4-yl]amine,
N-methyl-N-(4-nitrobenzyl)-N-[1-(2-methoxypyrimidin-4-yl)piperidin-4-yl]amine,
N-methyl-N-(4-nitrobenzyl)-N-[1-(2-methylthiopyrimidin-4-yl)piperidin-4-yl]amine,
N-methyl-N-(naphth-1-ylmethyl)-N-[1-(2-methoxypyrimidin-4-yl)piperidin-4-yl]amine,
N-methyl-N-(naphth-1-ylmethyl)-N-[1-(2-ethoxypyrimidin-4-yl)piperidin-4-yl]amine, and
N-methyl-N-(2,6-dichlorobenzyl)-N-[1-(2-methoxypyrimidin-4-yl)piperidin-4-yl]amine.

2. A method for preparing the compound or a pharmaceutically acceptable salt thereof according to claim 1, wherein the compound according to claim 1 is represented by formula (I)

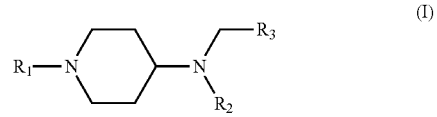

wherein the method comprises the following steps:

(1) reacting a compound of ($I_A$) with a compound of formula $R_1$-X in a solvent, in the presence of a base,

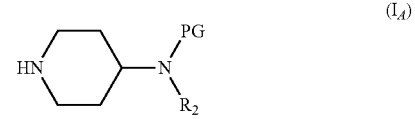

wherein $R_1$ is selected from the group consisting of 1-[(2-ethoxythiazol-5-yl)methyl], 1-[(2-chlorothiazol-5-yl)methyl], 1-[(2-methylthiothiazol-5-yl)methyl], 1-(2-methylthiopyrimidin-4-yl), 1-(2-methoxypyrimidin-4-yl), 1-(4-methoxypyrimidin-2-yl), 1-(6-methoxypyrimidin-4-yl), 1-(2-chloropyrimidin-4-yl), 1-(4-methylthiopyrimidin-2-yl), 1-(4-chloropyrimidin-2-yl) and 1-(2-ethoxypyrimidin-4-yl)

and $R_2$ is selected from the group consisting of hydrogen and methyl, X is a halogen, and PG is a conventional amino protecting group, to obtain a compound of ($I_B$);

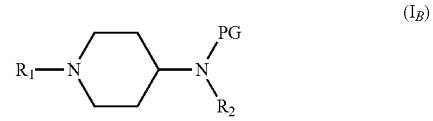

(2) deprotecting the compound of ($I_B$), to obtain a compound of formula ($I_C$);

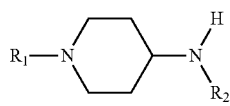 (I_C)

(3) reacting the compound of formula (I_C) with a compound of formula $R_3$—$CH_2$—Y in a solvent, in the presence of a base, wherein $R_3$ is selected from the group consisting of 2-cyanobenzyl, 4-cyanobenzyl, 3-cyanobenzyl, 2-fluoro-6-chlorobenzyl, 2-chlorobenzyl, 3-chlorobenzyl, 4-chlorobenzyl, 2,4-dichlorobenzyl, 3,4-dichlorobenzyl, 2,6-dichlorobenzyl, 2,5-dichlorobenzyl, 2-methylbenzyl, 4-methylbenzyl, 2-fluorobenzyl, 3-fluorobenzyl, 4-fluorobenzyl, 2,6-difluorobenzyl, 3,5-dimethoxybenzyl, 2-nitrobenzyl, 4-nitrobenzyl and naphth-1-ylmethyl, and Y is a halogen, to obtain the compound of formula (I); and (4) optionally converting the compound of formula (I) into the pharmaceutically acceptable salt thereof.

3. A pharmaceutical composition, comprising the compound, stereoisomer, pharmaceutically acceptable salt, solvate or N-oxide thereof according to claim 1, and at least one pharmaceutically acceptable carrier.

4. The pharmaceutical composition according to claim 3, further comprising one or more other antitumor drugs.

5. A method for treating a disease, comprising administering to a subject in need a therapeutically effective amount of the compound, stereoisomer, pharmaceutically acceptable salt, solvate or N-oxide thereof according to claim 1, wherein the disease is a tumor.

* * * * *